US011492399B2

(12) United States Patent
Tsukada et al.

(10) Patent No.: US 11,492,399 B2
(45) Date of Patent: Nov. 8, 2022

(54) ANTI-IGM/B CELL SURFACE ANTIGEN BISPECIFIC ANTIBODY

(71) Applicant: ZENYAKU KOGYO CO., LTD., Tokyo (JP)

(72) Inventors: Yasukatsu Tsukada, Tokyo (JP); Takahiro Ohashi, Tokyo (JP); Hitoshi Miyashita, Tokyo (JP); Satoko Tatebe, Tokyo (JP); Jumpei Enami, Tokyo (JP)

(73) Assignee: ZENYAKU KOGYO CO., LTD., Tokyo (JP)

( * ) Notice: Subject to any disclaimer, the term of this patent is extended or adjusted under 35 U.S.C. 154(b) by 178 days.

(21) Appl. No.: 16/494,951

(22) PCT Filed: Mar. 23, 2018

(86) PCT No.: PCT/JP2018/011877
§ 371 (c)(1),
(2) Date: Sep. 17, 2019

(87) PCT Pub. No.: WO2018/174274
PCT Pub. Date: Sep. 27, 2018

(65) Prior Publication Data
US 2020/0123248 A1 Apr. 23, 2020

(30) Foreign Application Priority Data

Mar. 24, 2017 (JP) .............................. JP2017-060131

(51) Int. Cl.
C07K 16/28 (2006.01)
A61P 35/00 (2006.01)
C07K 16/46 (2006.01)
C07K 16/42 (2006.01)

(52) U.S. Cl.
CPC .............. *C07K 16/28* (2013.01); *A61P 35/00* (2018.01); *C07K 16/42* (2013.01); *C07K 16/46* (2013.01); *C07K 2317/24* (2013.01); *C07K 2317/31* (2013.01); *C07K 2317/565* (2013.01)

(58) Field of Classification Search
None
See application file for complete search history.

(56) References Cited

U.S. PATENT DOCUMENTS

| 5,994,524 | A | 11/1999 | Matsushima et al. |
| 6,024,956 | A | 2/2000 | Matsushima et al. |
| 6,048,972 | A | 4/2000 | Matsushima et al. |
| 6,068,840 | A | 5/2000 | Matsushima et al. |
| 6,245,894 | B1 | 6/2001 | Matsushima et al. |
| 2002/0082396 | A1 | 6/2002 | Matsushima et al. |
| 2012/0258108 | A1* | 10/2012 | Ghayur ............ A61P 25/04 424/136.1 |
| 2014/0212425 | A1* | 7/2014 | Chang ............ C07K 14/56 424/136.1 |

FOREIGN PATENT DOCUMENTS

WO 96/02576 A1 2/1996

OTHER PUBLICATIONS

Careyetai. (Cell Research, 17:942-955, 2007).*
Carey et al. (Cell Research, 17:942-955, 2007).*
Mariuzza (Annu. Rev. Biophys. Biophys. Chem., 16: 139-159, 1987).*
Cohen et al., "Anti-idiotype x Anti-LFA-1 Bispecific Antibodies Inhibit Metastasis of B Cell Lymphoma", The Journal of Immunology, vol. 170, No. 5, pp. 2695-2701 (2003).
Avin et al., "Anti-idiotype x Anti-CD44 Bispecific Antibodies Inhibit Invasion of Lymphoid Organs by B Cell Lymphoma", The Journal of Immunology, vol. 173, No. 7, pp. 4736-4743 (2004).
Donahue et al., "Proliferation and Survival of Activated B Cells Requires Sustained Antigen Receptor Engagement and Phosphoinositide 3-Kinase Activation", The Journal of Immunology, vol. 170, No. 12, pp. 5851-5860 (2003).
Mongini et al., "Innate Immunity and Human B Cell Clonal Expansion: Effects on the Recirculating B2 Subpopulation", The Journal of Immunology, vol. 175, No. 9, pp. 6143-6154 (2005).
Ohashi et al., "A Novel Anti-IgM/HLA-DR Bispecific Antibody for Treatment of Refractory B Cell Malignancies", Blood, vol. 132, issue supplement 1, 6 pages (2018).
Extended European Search Report issued in EP Patent Application No. 18770221.2, dated Dec. 8, 2020.
Besnault et al., "B Cell Receptor Cross-Linking Triggers a Caspase-8-Dependent Apoptotic Pathway That is Independent of the Death Effector Domain of Fas-Associated Death Domain Protein", The Journal of Immunology, vol. 167, No. 2, pp. 733-740 (2001).
Carey et al., "IL-4 Protects the B-cell Lymphoma Cell Line CH31 from anti-IgM-Induced Growth Arrest and Apoptosis: Contribution of the PI-3 Kinase/AKT Pathway", Cell Research, vol. 17, No. 11, pp. 942-955 (2007).
Cutrona et al., "ABSSUB-4465: Chronic Lymphocytic Leukemia Cell Capacity of Expressing and Responding to Surface IGM (S-IgM) or S-IgD Predicts Disease Progression and is Associated With Specific MIRNA/MRNA Signatures", 19th Congress of the European Hematology Association, 7 pages (2014).
Mongini et al., "Evidence for an Upper Affinity Threshold for Anti-IgM-Induced Apoptosis in a Human B-Cell Lymphoma", Blood, vol. 92, No. 10, pp. 3756-3771 (1998).
Miyazaki et al., "Gene Expression Profiling of Diffuse Large B-cell Lymphoma Supervised by CD21 Expression", British Journal of Haematology, vol. 142, No. 4, pp. 562-570 (2008).
International Search Report issued in PCT/JP2018/011877, dated Jun. 19, 2018, along with an English-language translation.
First Examination Report issued in IN Patent Application No. 201917039602, dated Feb. 24, 2022.

* cited by examiner

*Primary Examiner* — Nelson B Moseley II
(74) *Attorney, Agent, or Firm* — Greenblum & Bernstein, P.L.C.

(57) ABSTRACT

Provided is an antibody that has a high binding activity to membrane-bound IgM on the surface of B cells and exhibits a growth inhibition effect on the B cells, even in the presence of soluble IgM in blood.
A bispecific antibody, which binds to IgM and a B cell surface antigen.

15 Claims, 16 Drawing Sheets
Specification includes a Sequence Listing.

[Figure 1]
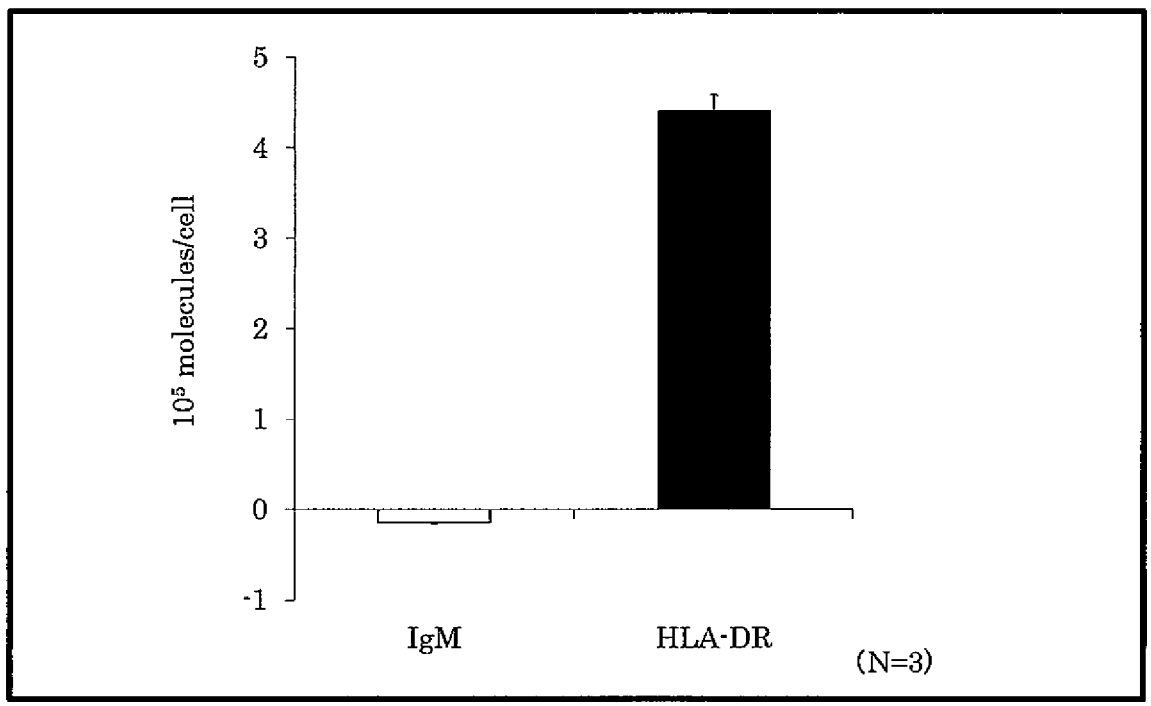
[Figure 2]
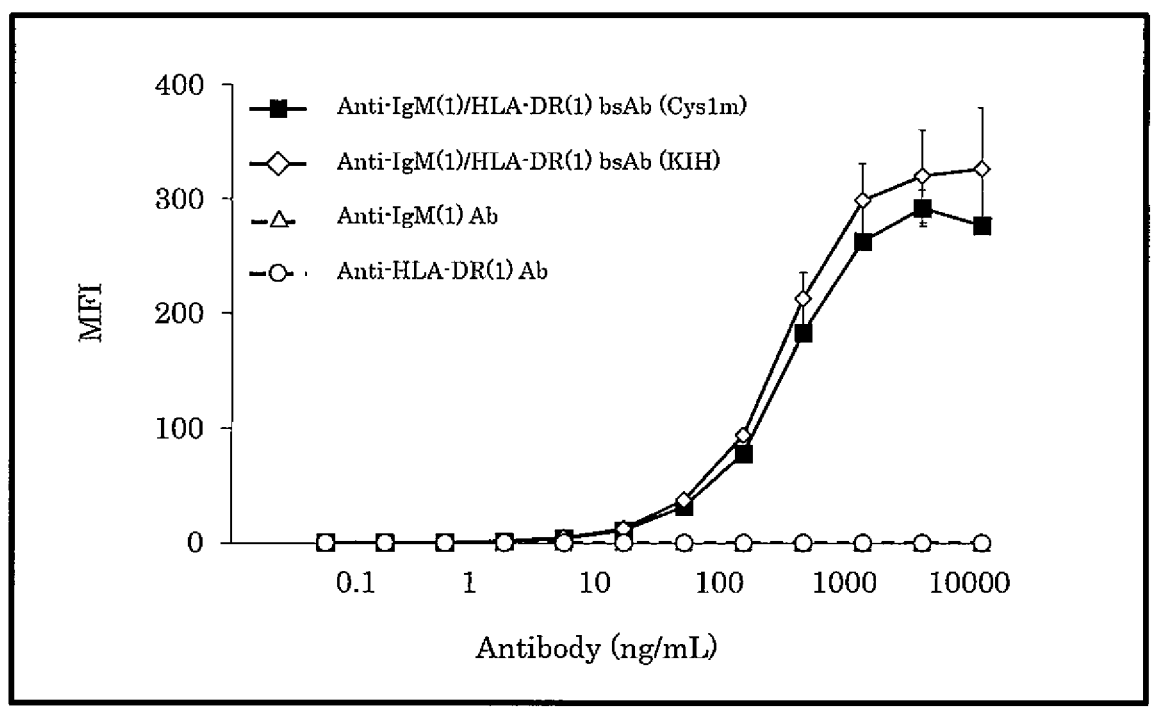

[Figure 3]
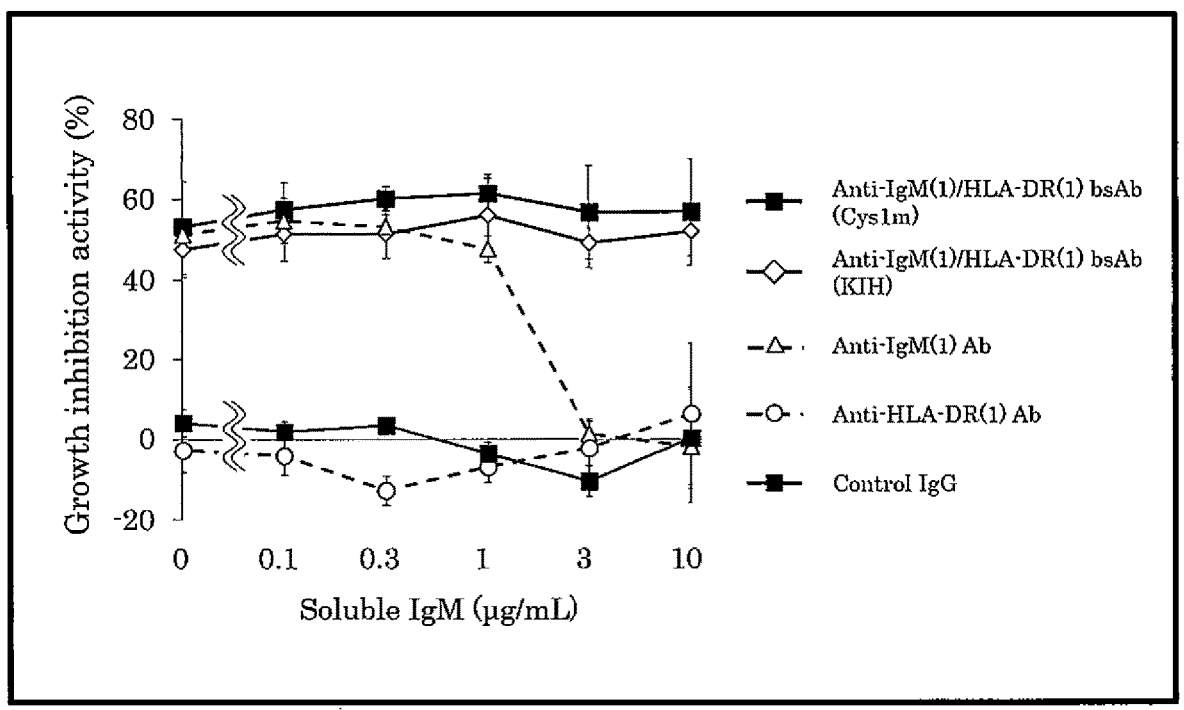
[Figure 4]
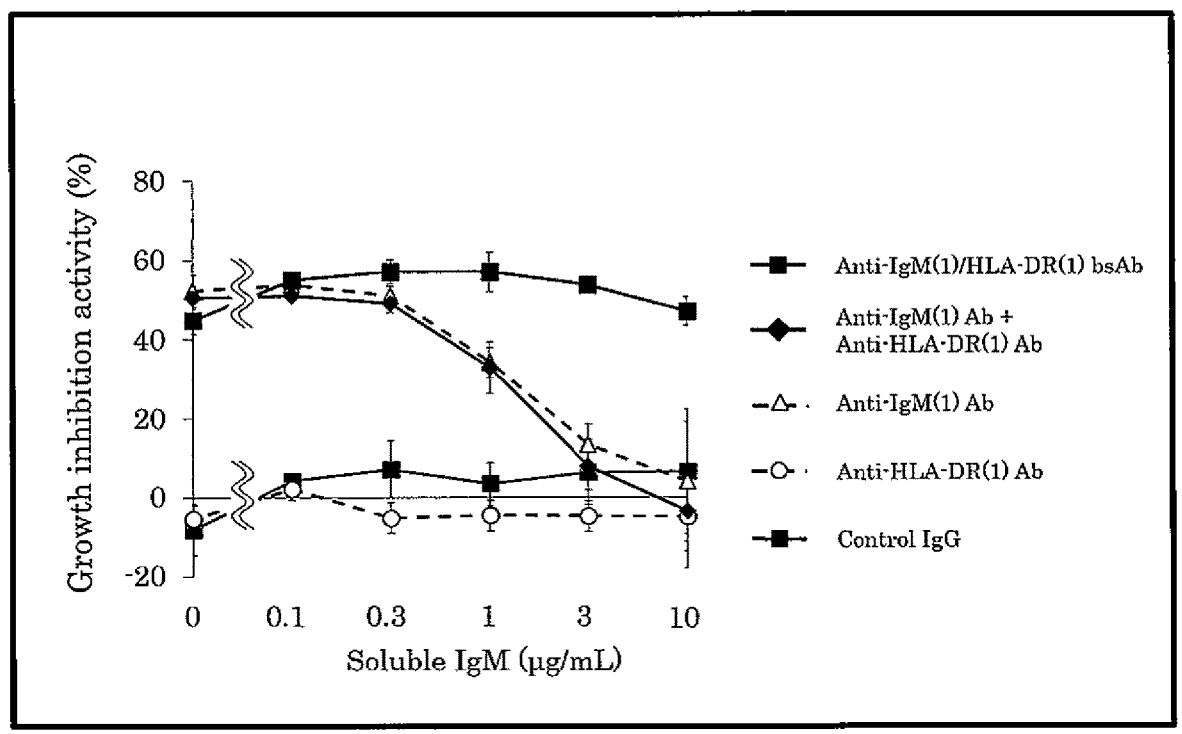

[Figure 5]
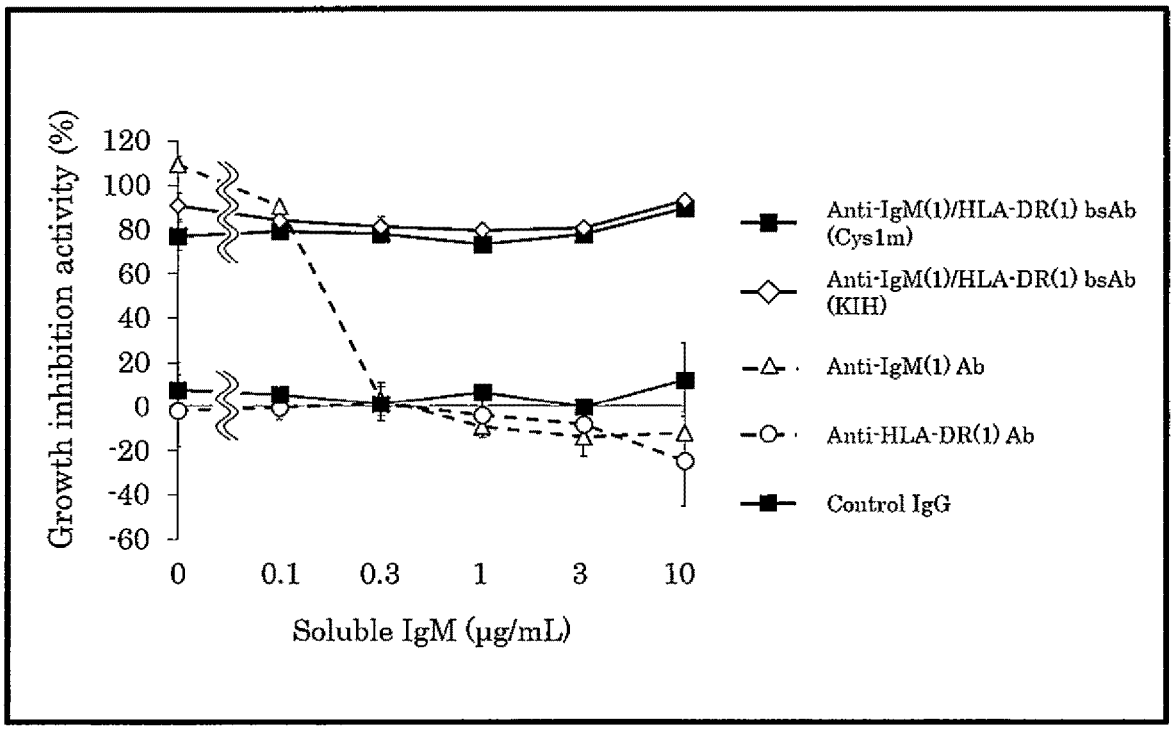
[Figure 6]
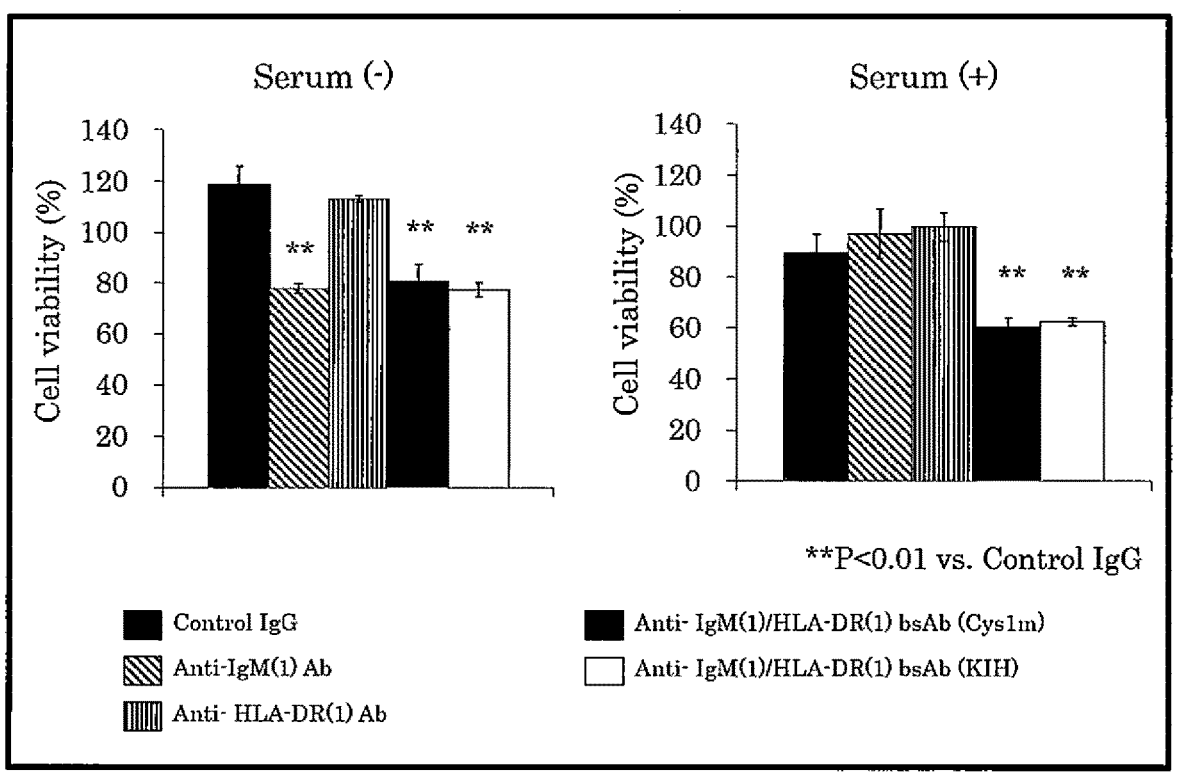

[Figure 7]
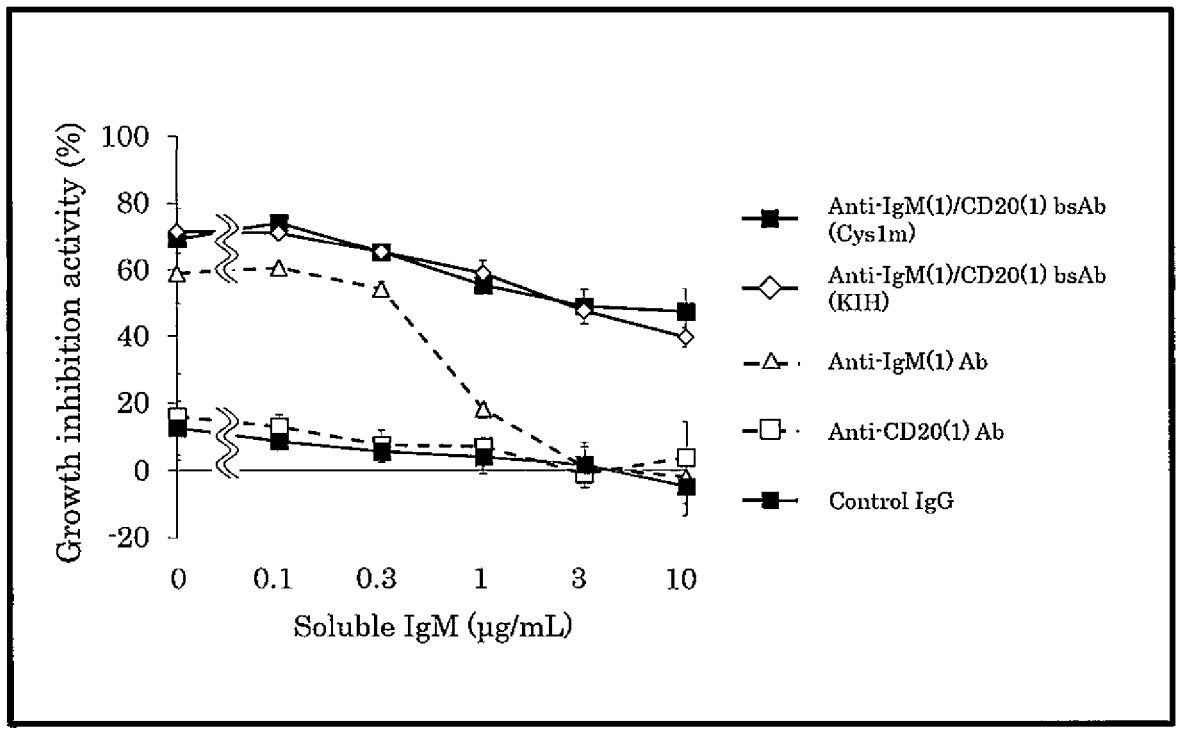
[Figure 8]
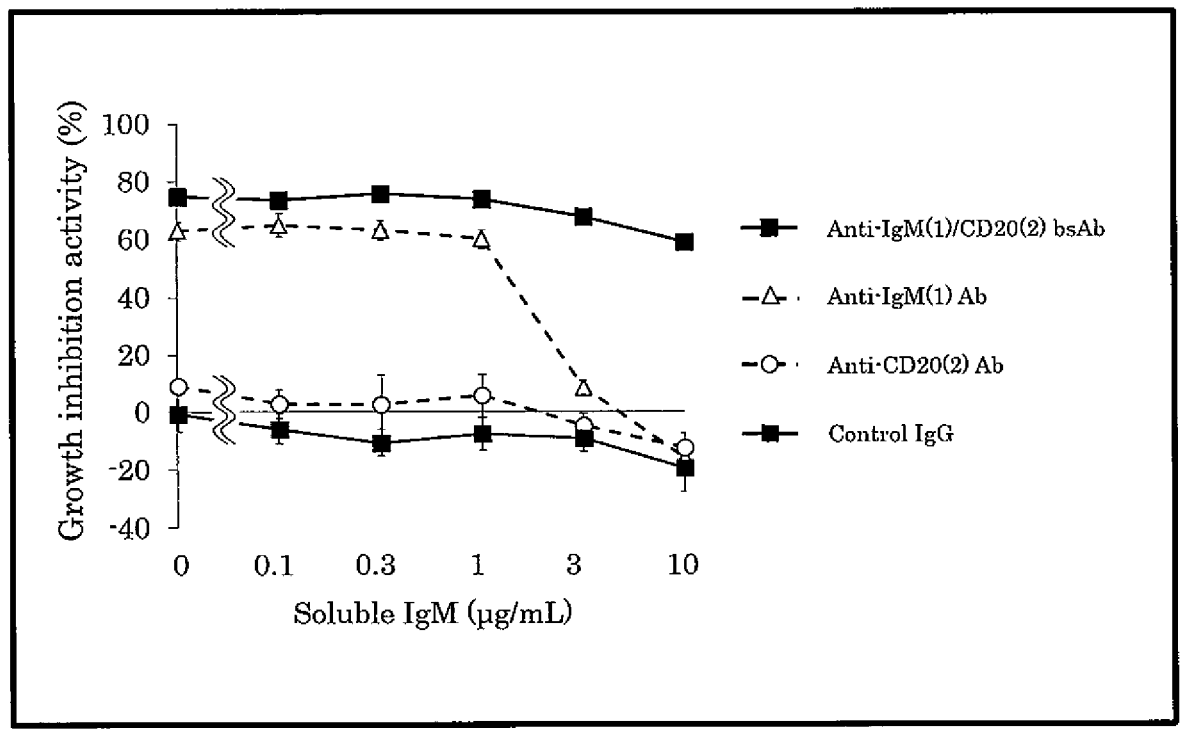

[Figure 9]
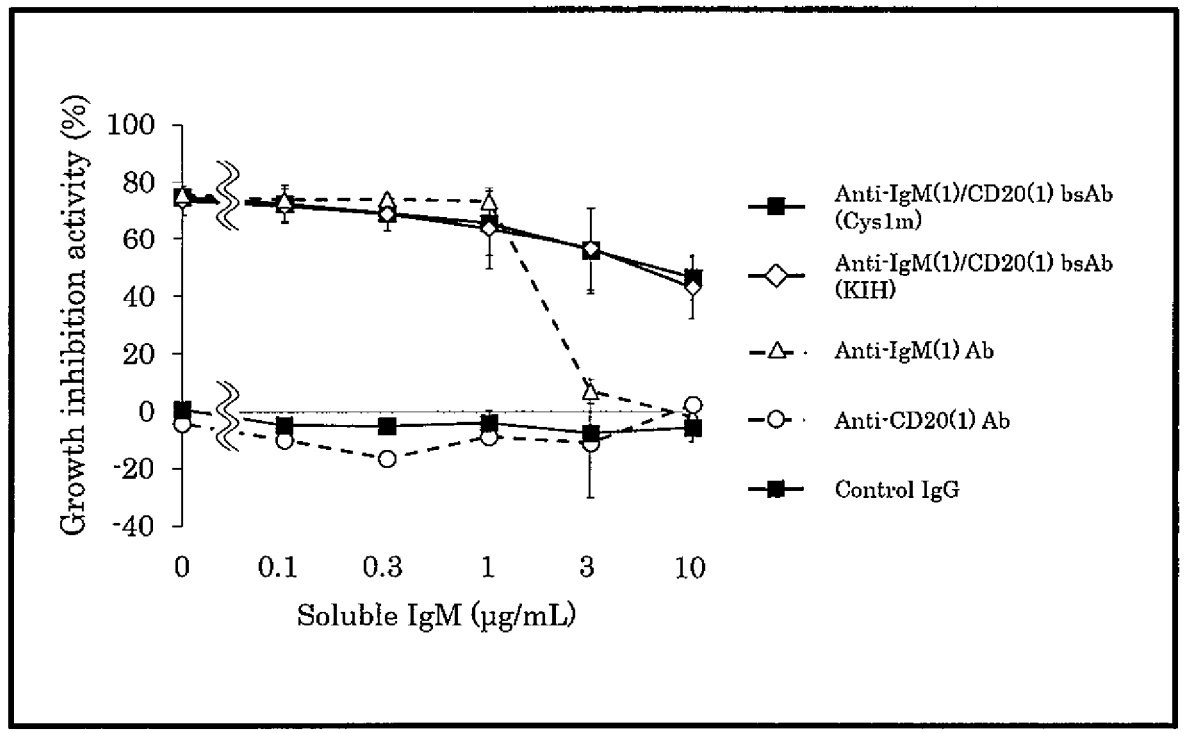
[Figure 10]
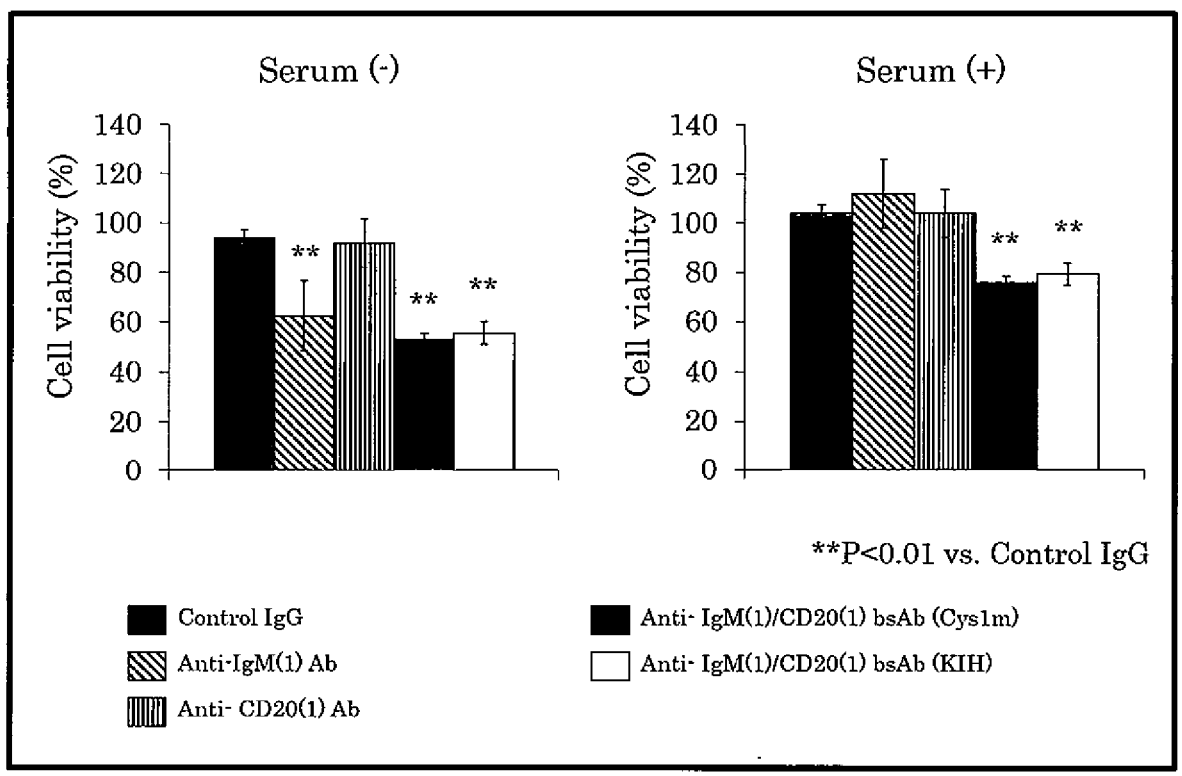

[Figure 11]
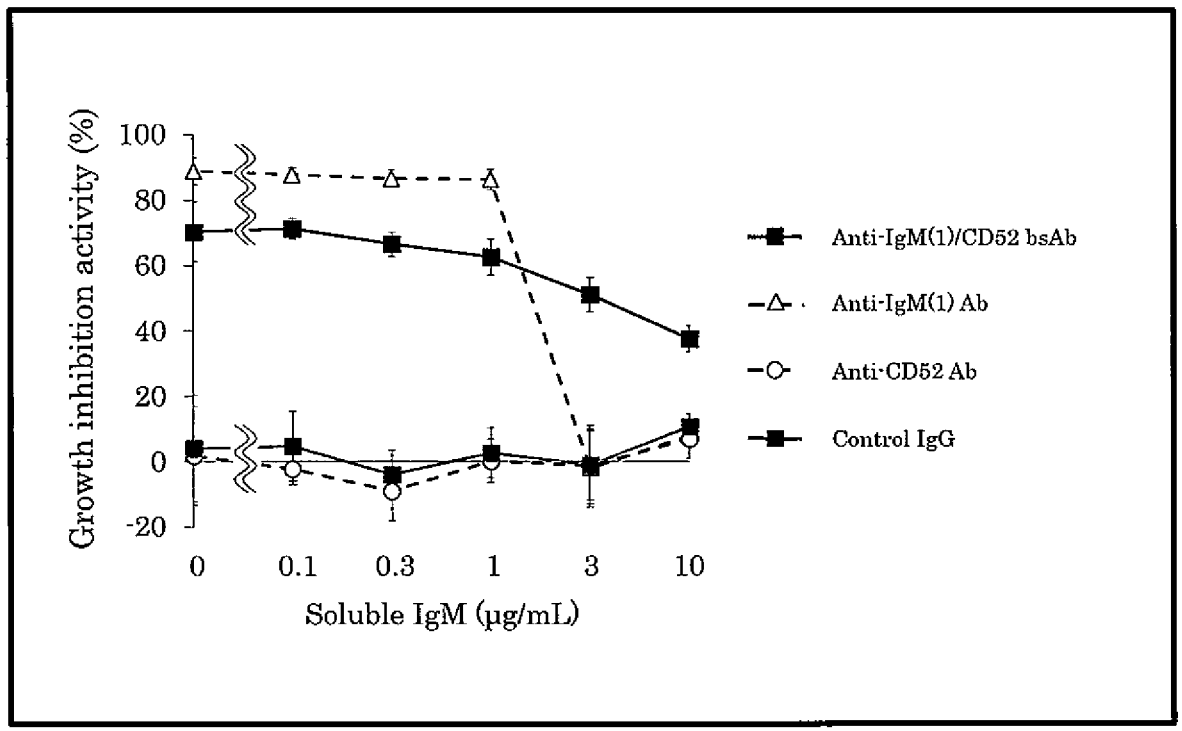
[Figure 12]
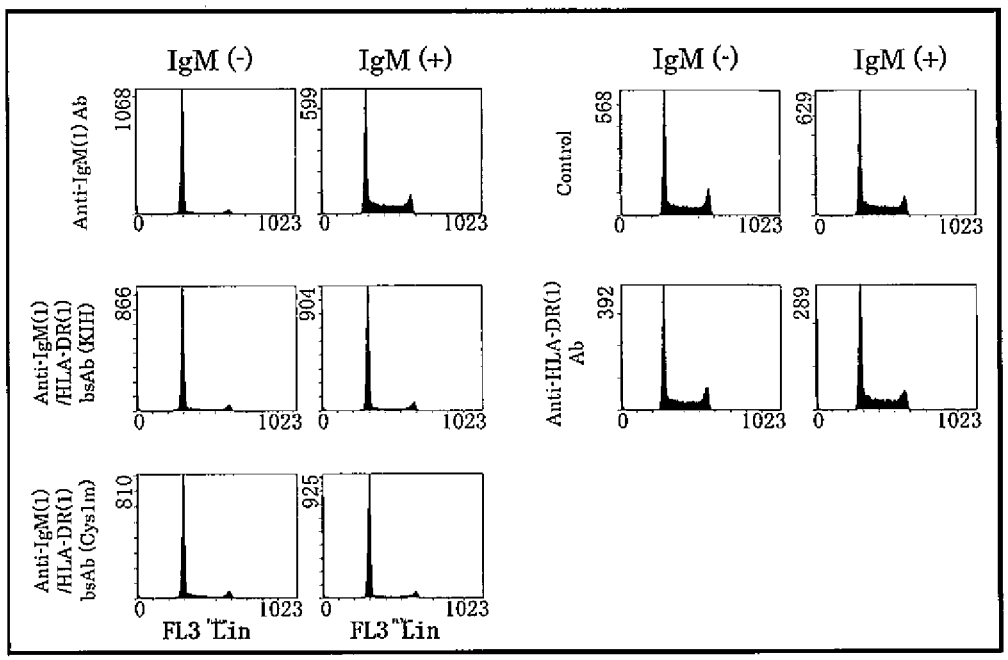

[Figure 13]
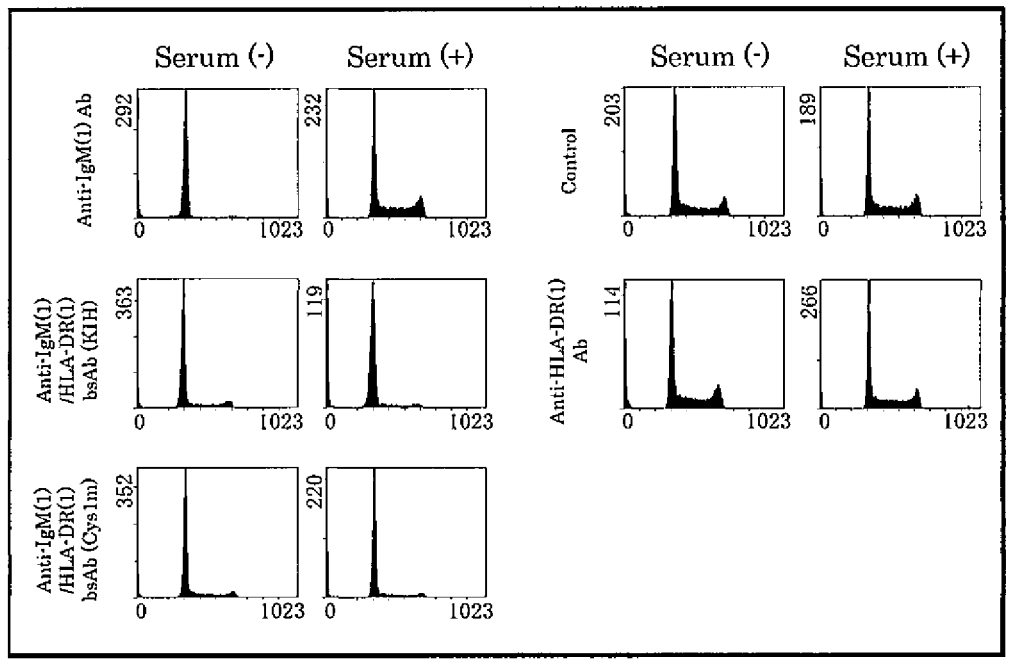

[Figure 14]
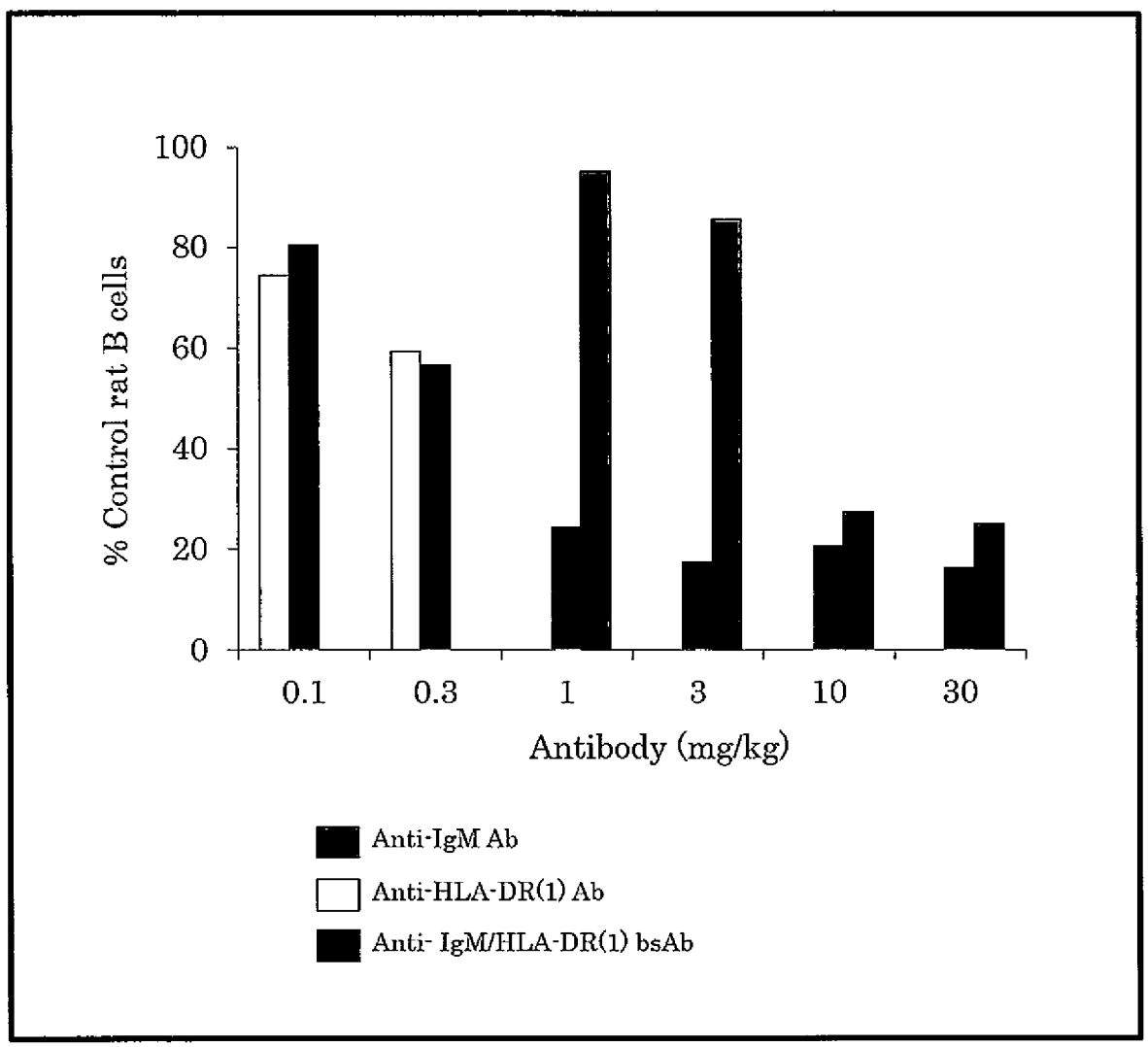

[Figure 15]
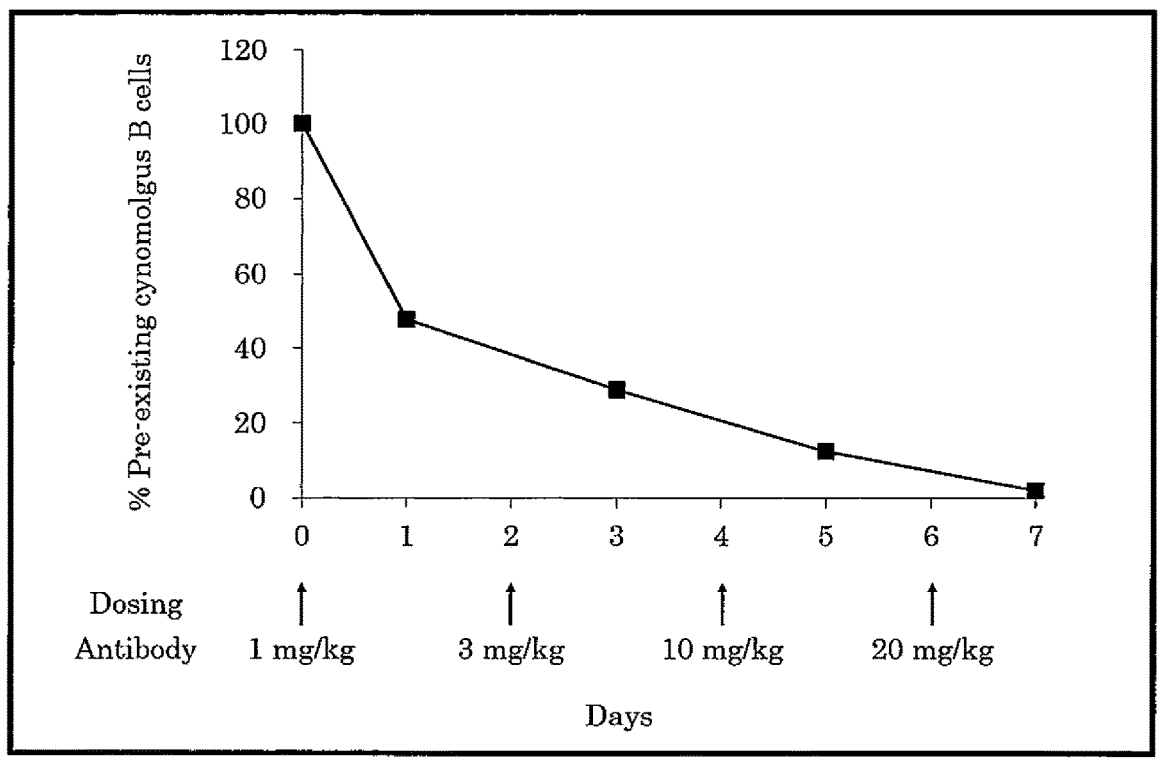
[Figure 16]
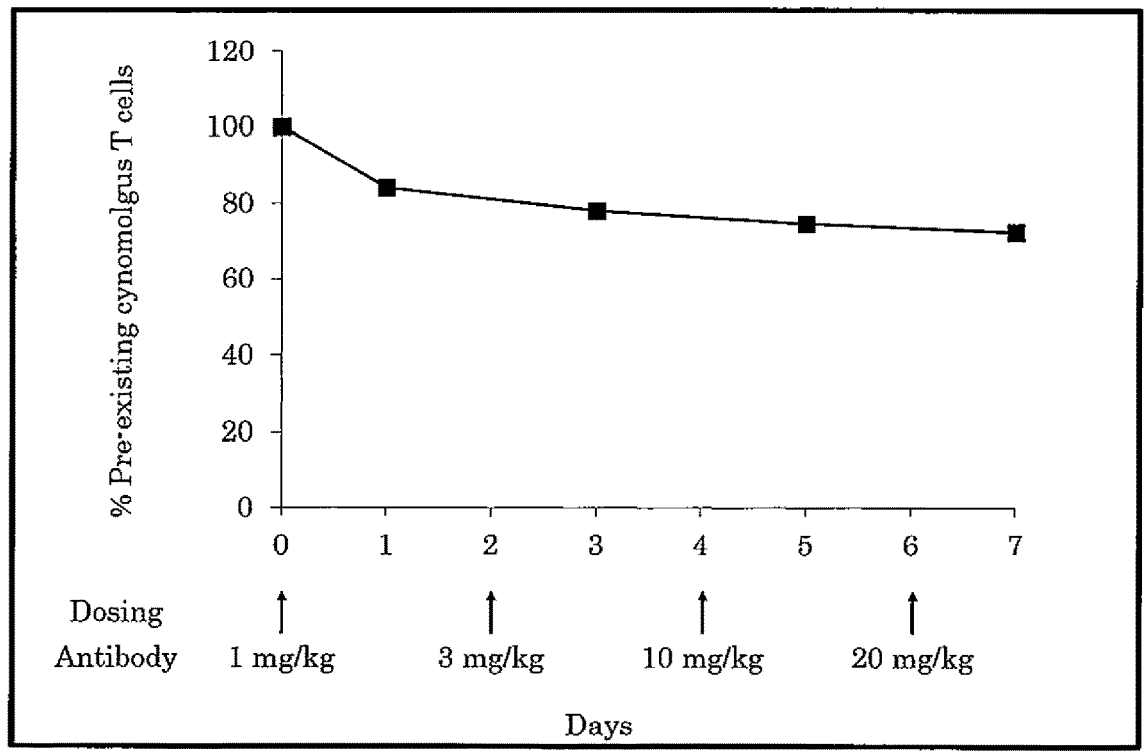

[Figure 17]
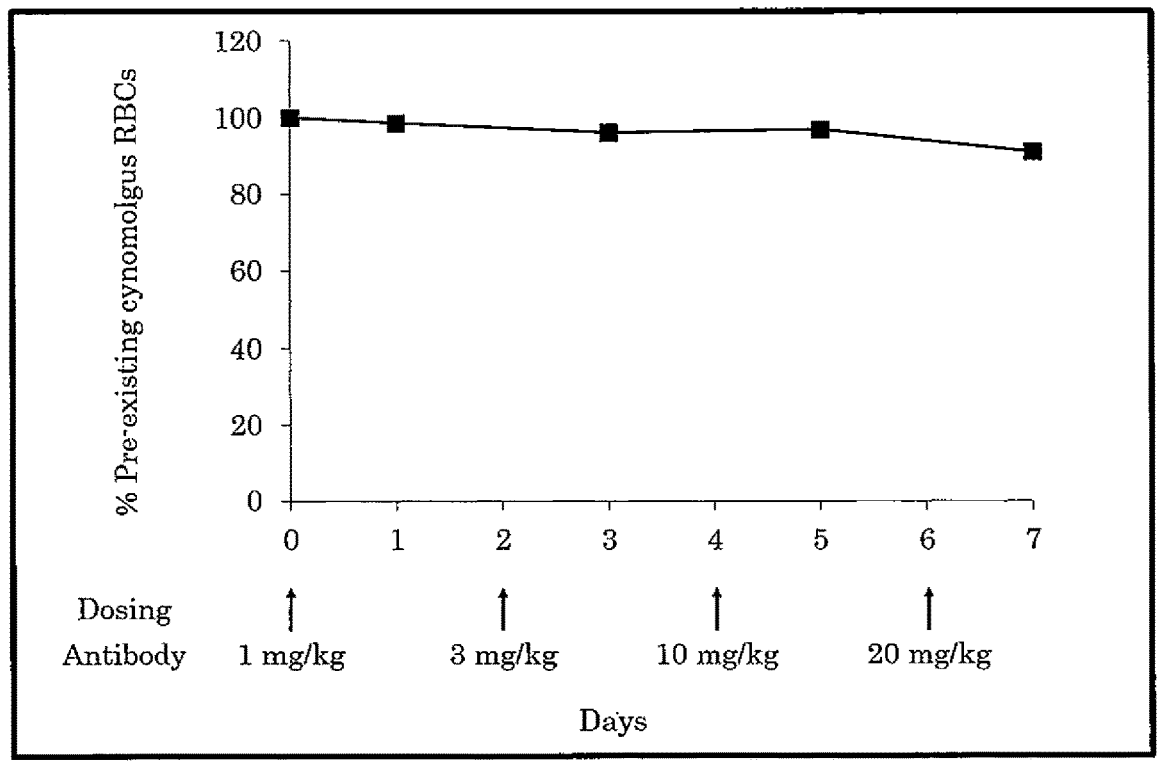
[Figure 18]
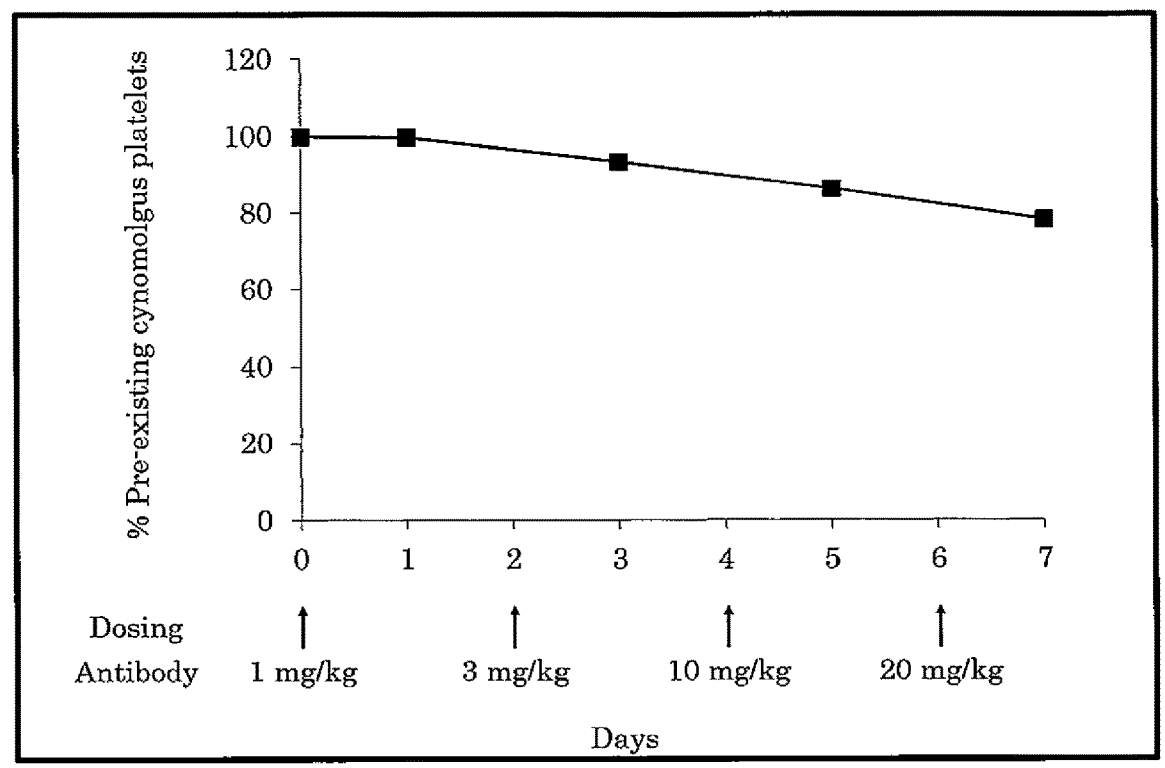

[Figure 19]
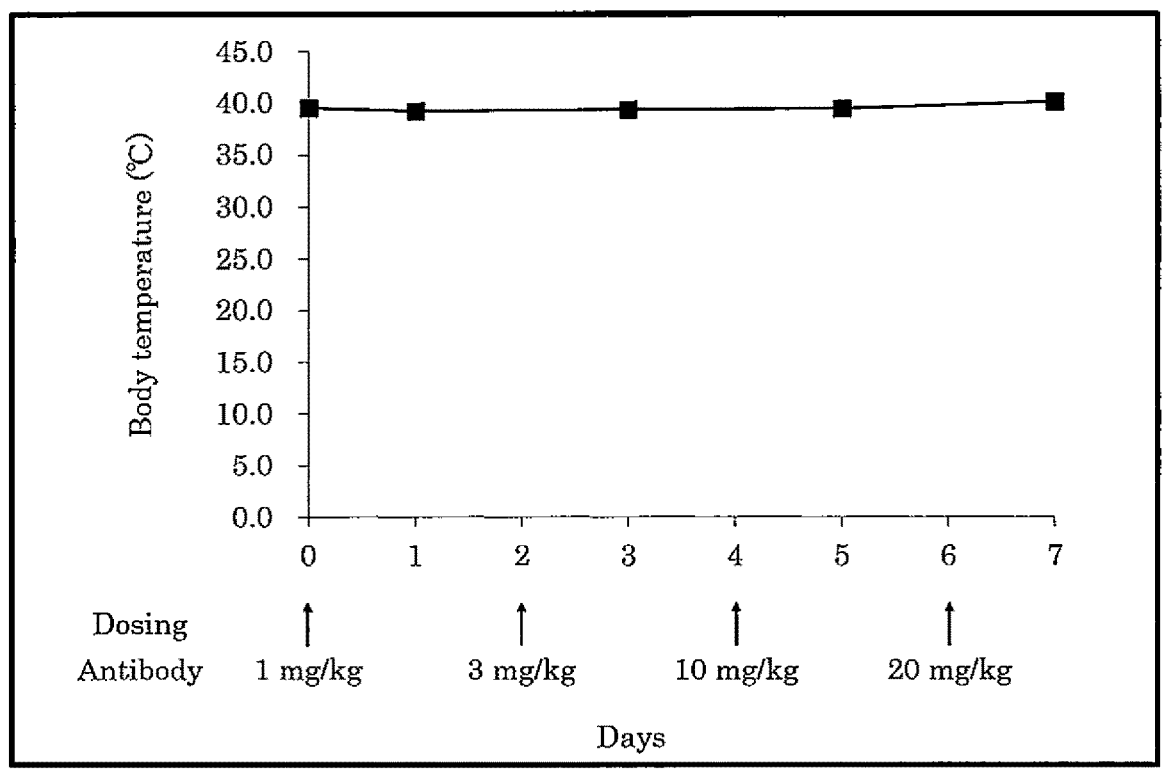
[Figure 20]
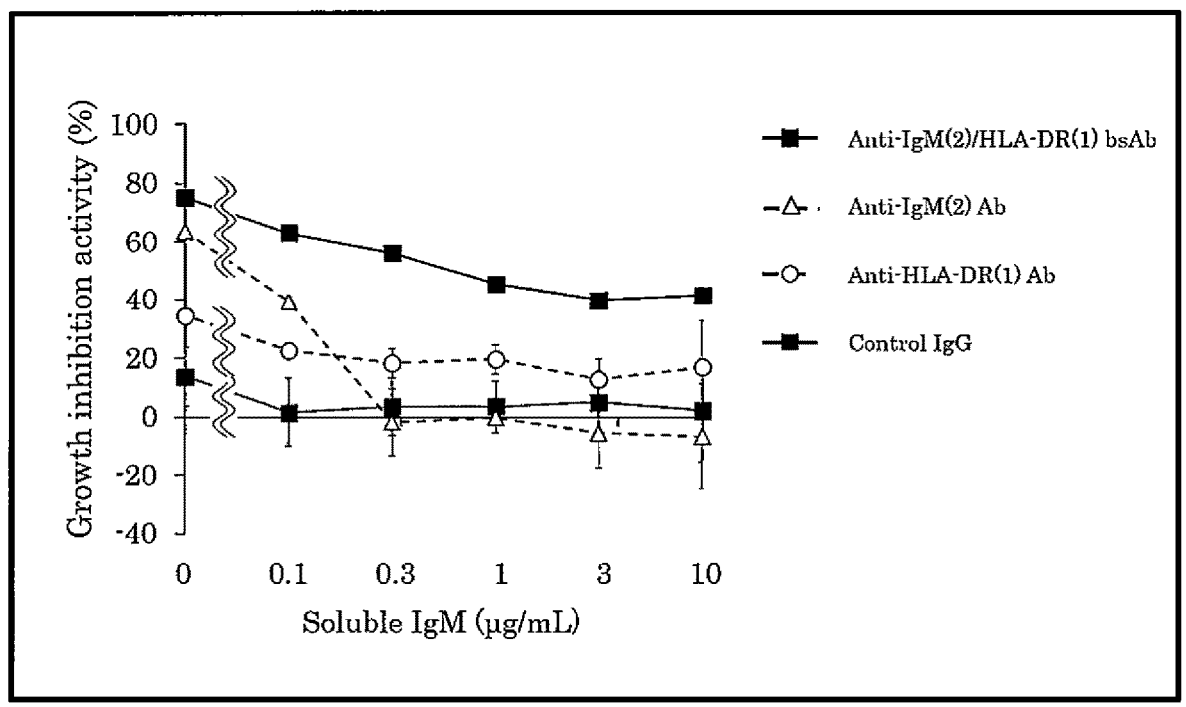

[Figure 21]
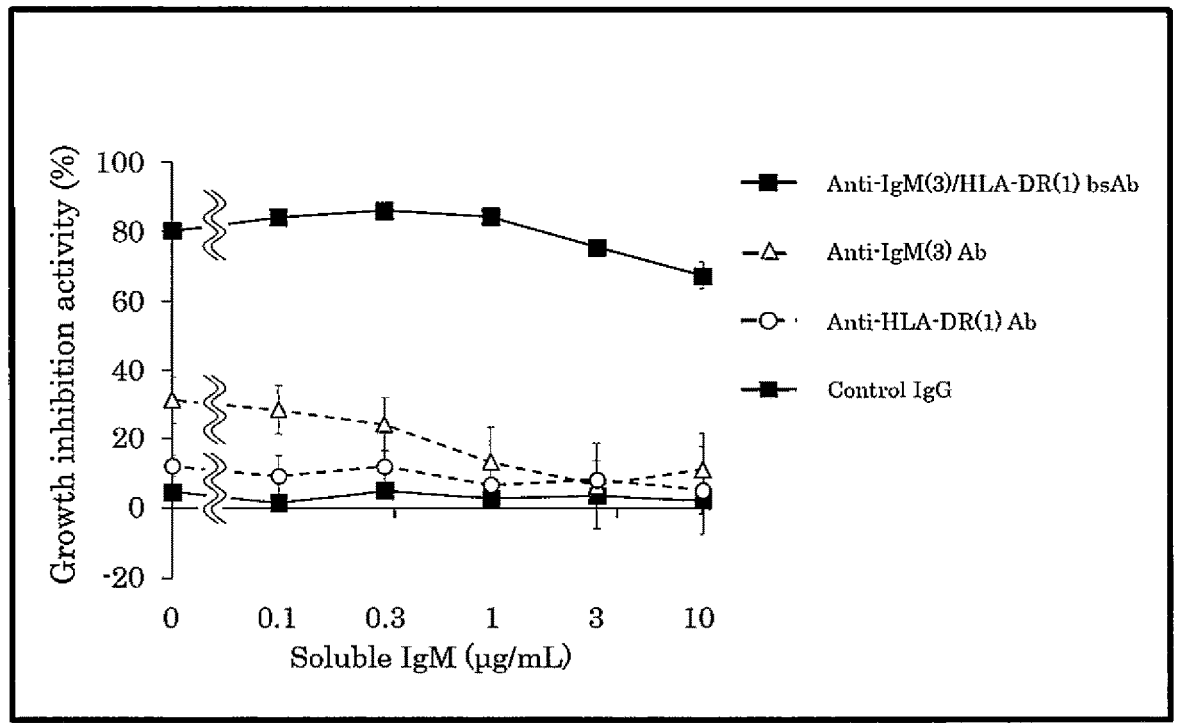
[Figure 22]
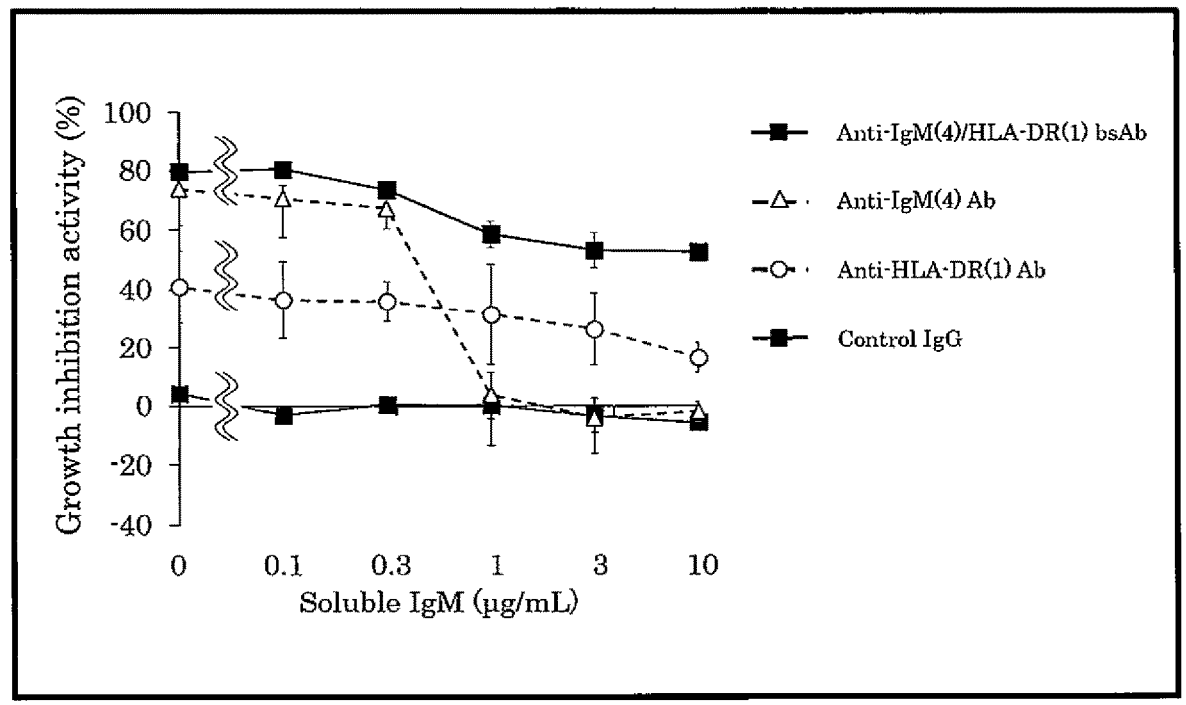

[Figure 23]
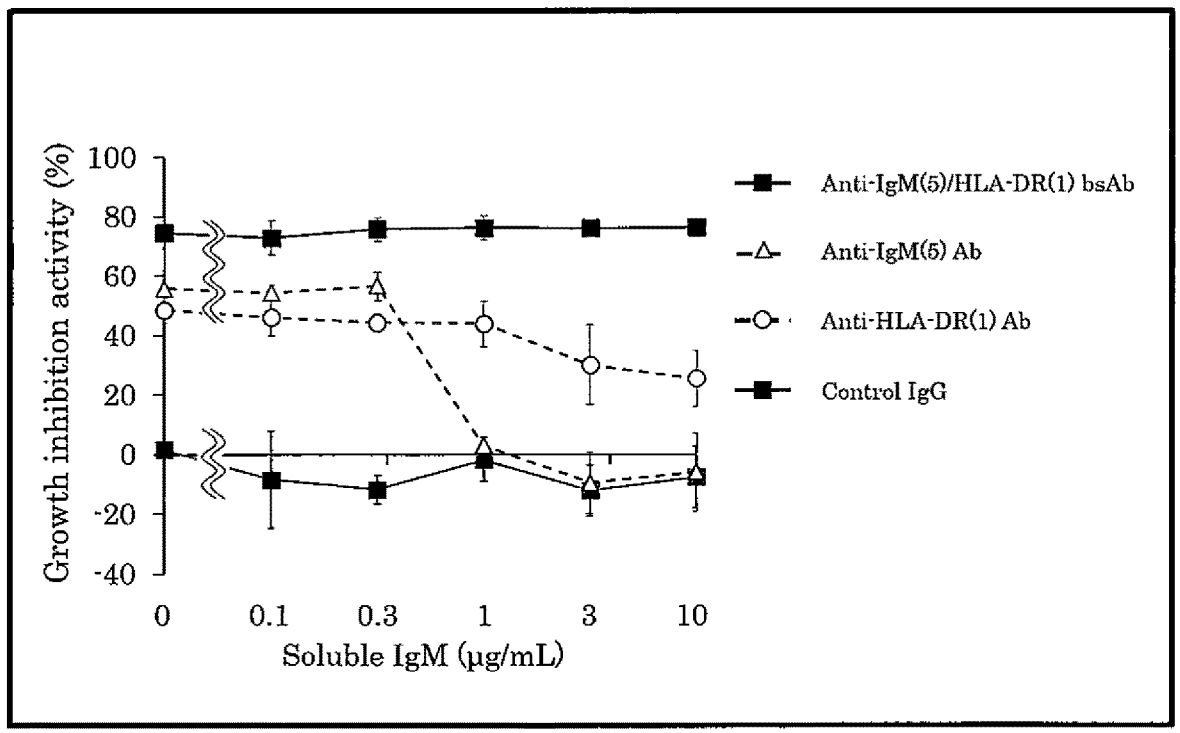
[Figure 24]
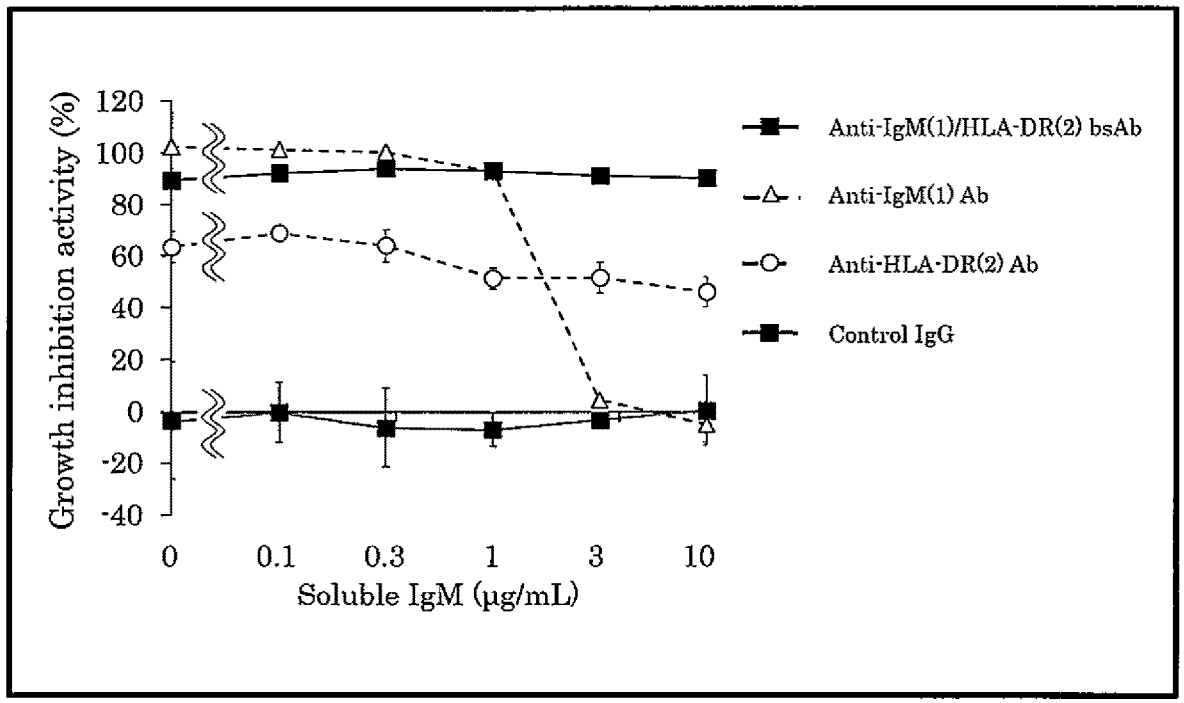

[Figure 25]
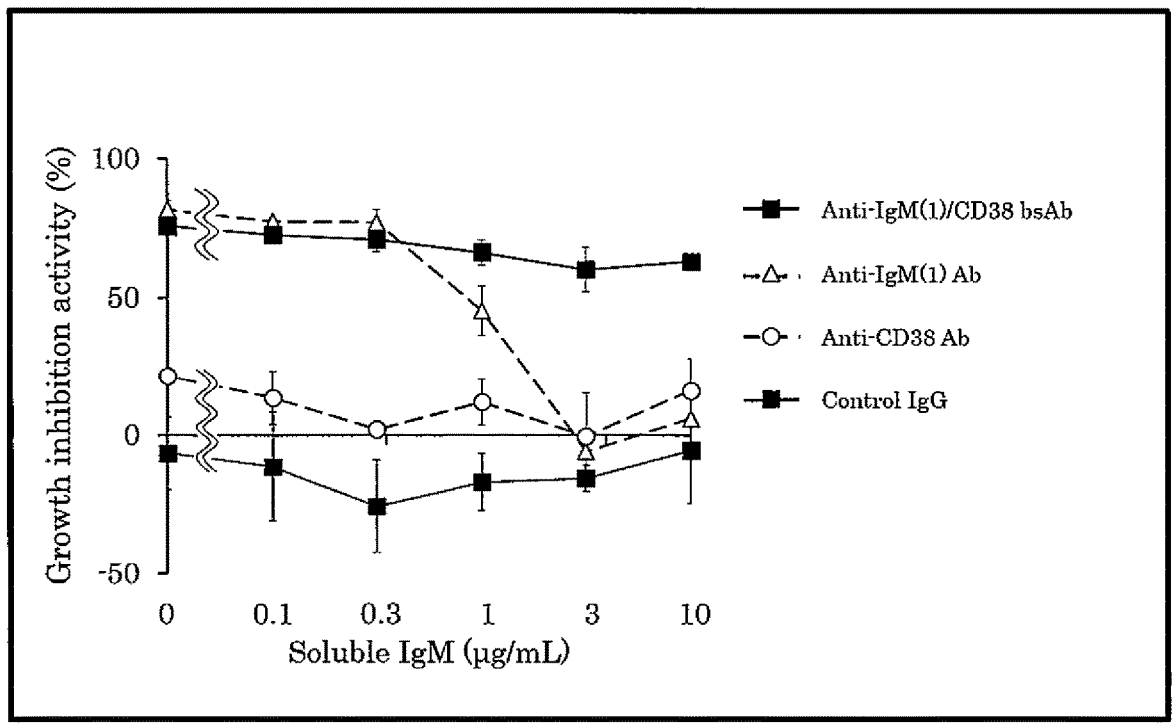
[Figure 26]
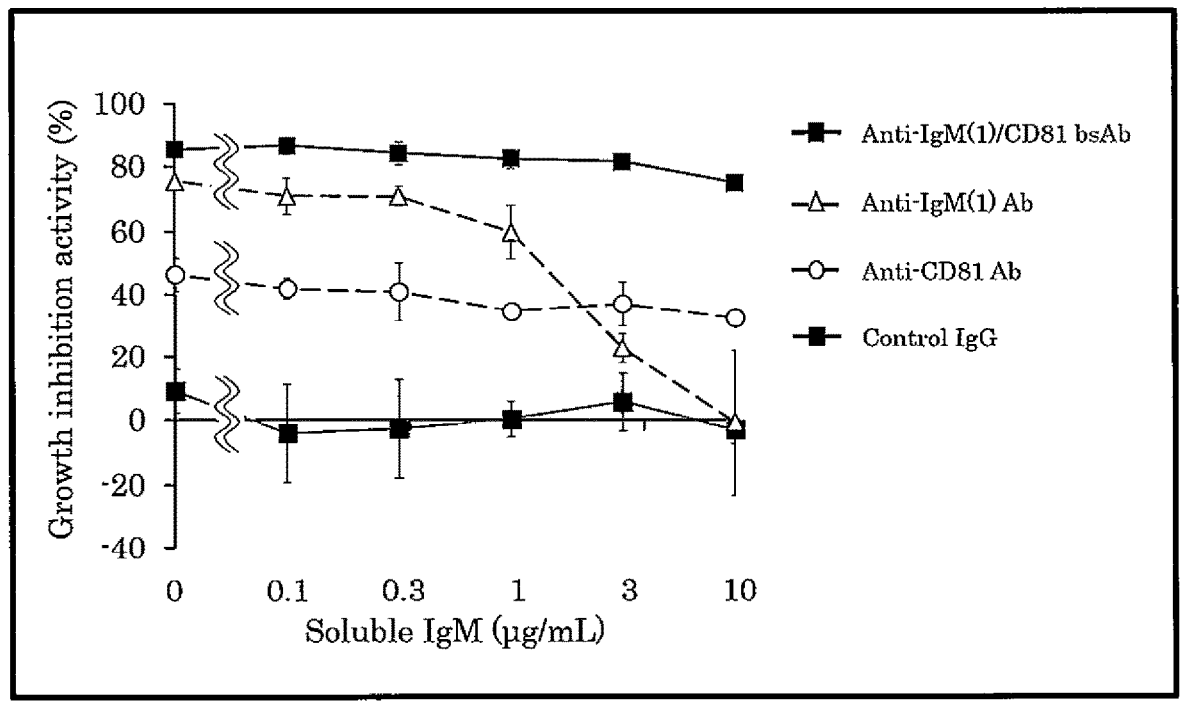

[Figure 27]
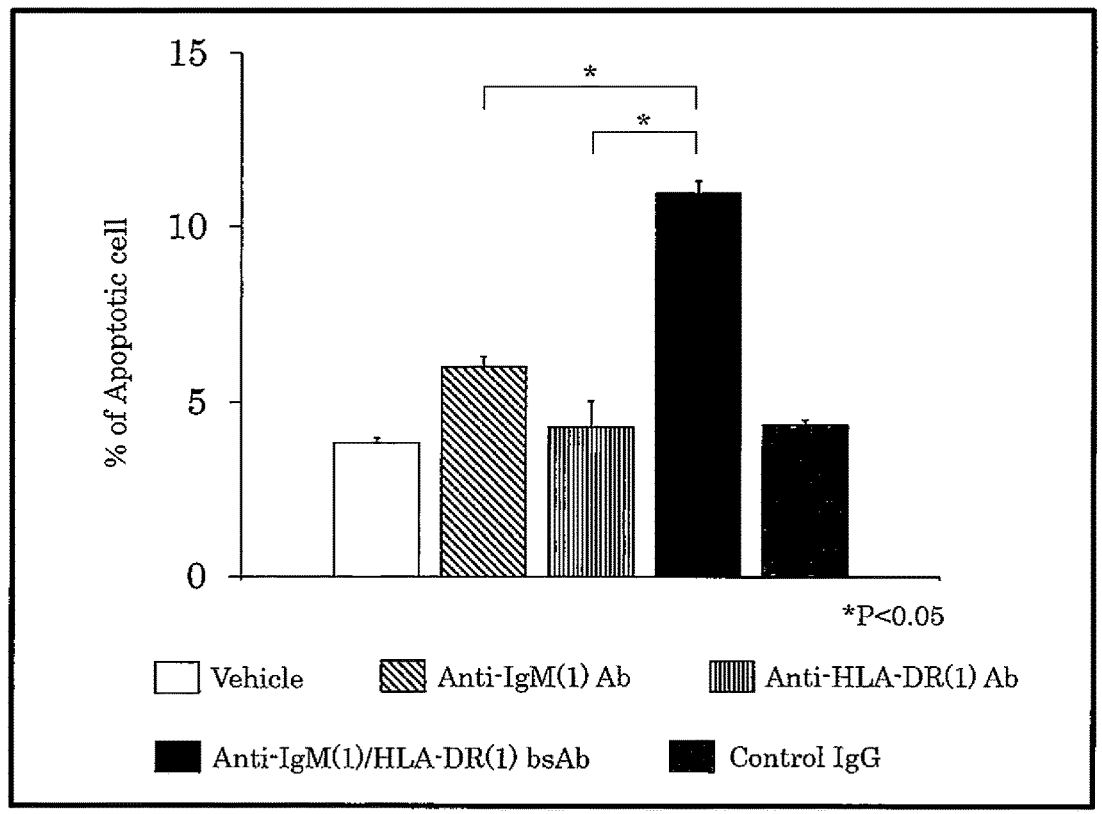
[Figure 28]
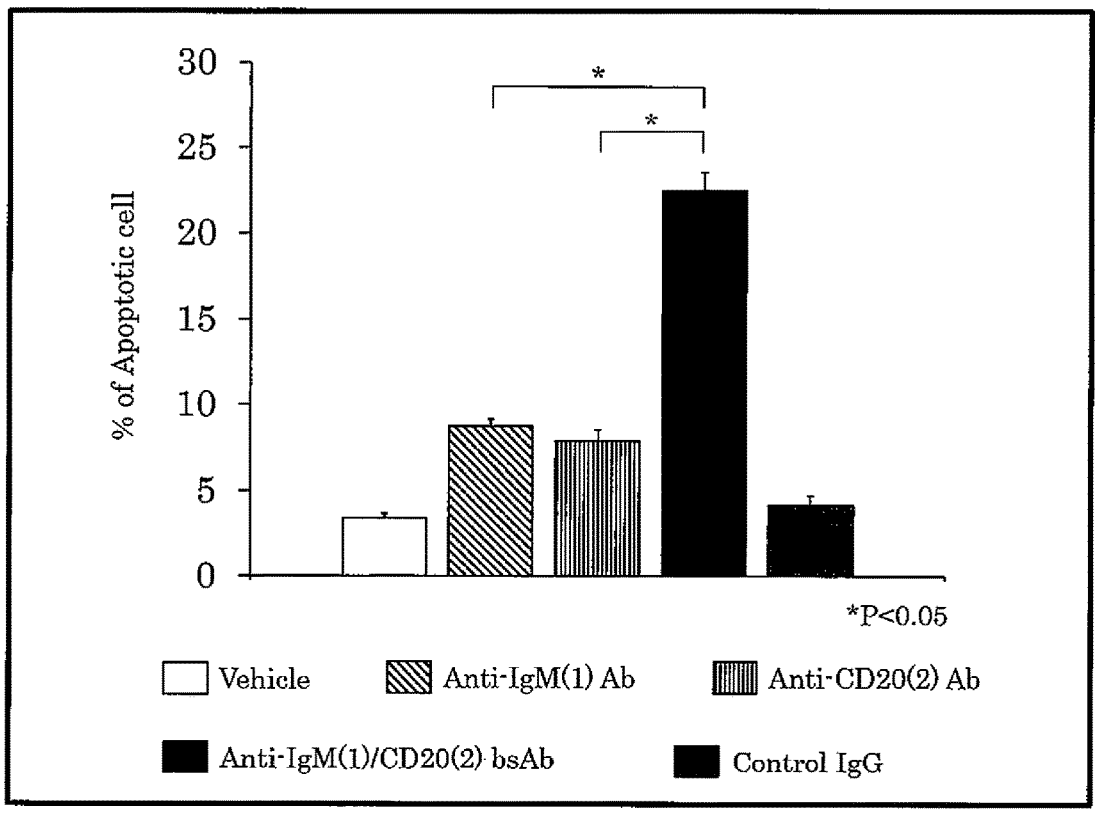

[Figure 29]
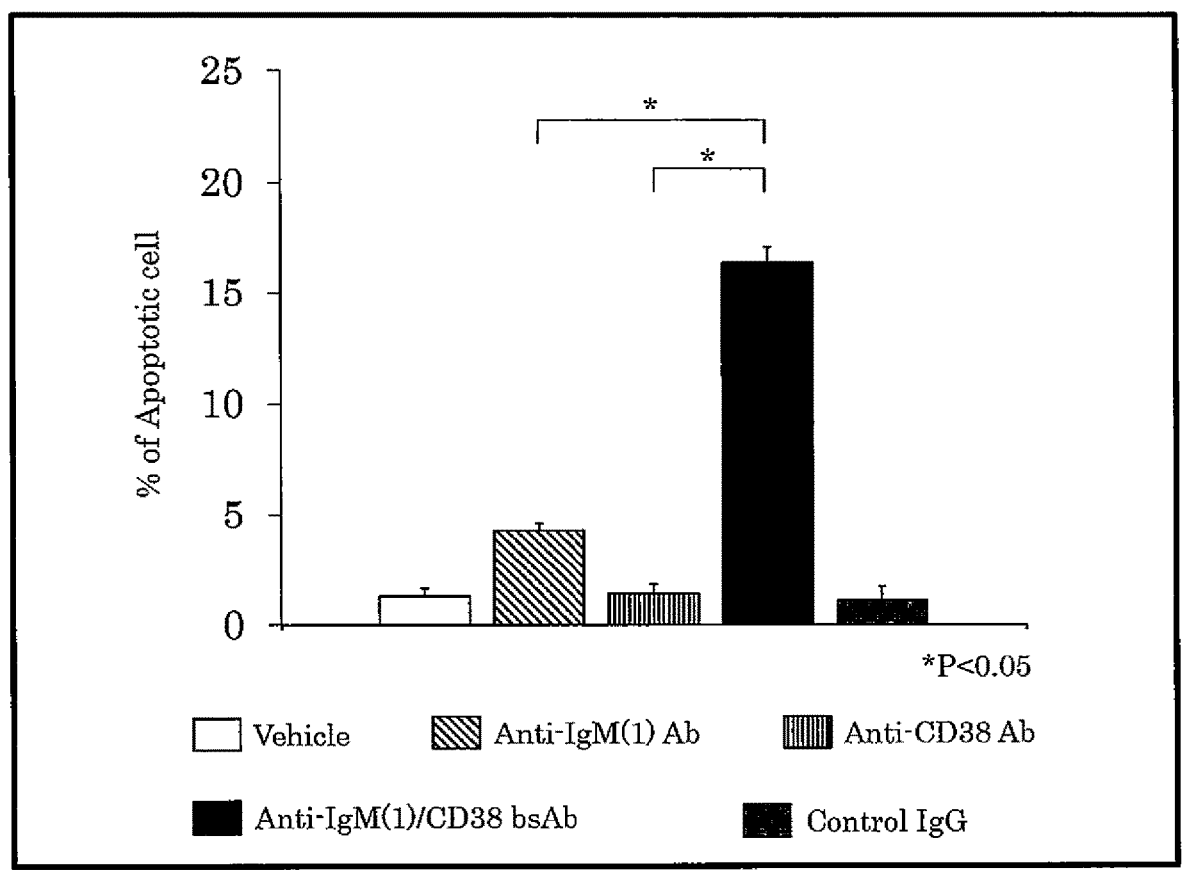

ANTI-IgM/B CELL SURFACE ANTIGEN BISPECIFIC ANTIBODY

TECHNICAL FIELD

The present invention relates to an anti-IgM/B cell surface antigen bispecific antibody which binds to IgM and a B cell surface antigen, and use thereof.

BACKGROUND ART

Immunoglobulin M (IgM) is a class of immunoglobulin which is composed of antibodies and proteins structurally and functionally associated with the antibodies and includes membrane-bound IgM and soluble IgM. The membrane-bound IgM is specifically expressed on B cells, which are one of the major types of lymphocytes involved in adaptive immunity, as a B cell receptor and involved in the life or death of the B cells. Binding of an antigen to a B cell receptor leads to B cell growth, where some of B cells differentiate into plasma cells. The plasma cells secrete a large amount of soluble IgM. The soluble IgM forms a pentamer or hexamer, is present in blood in a large amount (0.4 to 2.8 mg/ml), and contributes to initial immune response.

It is known that an anti-IgM monoclonal antibody against IgM inhibits cell growth of B cell tumor cell lines and induces apoptosis of the cell lines in vitro (Non Patent Literatures 1, 2 and 3).

In the 21st century, cancer treatment with antibodies, together with progress in technology such as humanized or engineered antibody by genetic engineering has come to be accepted as an effective treatment method. Many antibody drugs have recently been placed on the market, and new antibody drugs are being developed. Of these, antibody drugs directly targeting cancer recognize a wide variety of antigens as target antigens, and are useful as molecular target drugs which exhibit anti-tumor effects by action mechanisms such as antibody dependent cell-mediated cytotoxicity (ADCC), complement dependent cytotoxicity (CDC), growth signal transduction inhibition, and cytotoxic activity brought by the drug of an antibody-drug conjugate.

On the other hand, there are reports that B cell tumor expressing membrane-bound IgM is poor in prognosis (Non Patent Literatures 4 and 5). Thus, it is assumed that membrane-bound IgM can become a target for the treatment. However, so far, no anti-IgM monoclonal antibody has been put into practical use as an agent for treating B cell tumors.

CITATION LIST

Non Patent Literature

Non Patent Literature 1: Carey, G. B., et al., Cell Res., 17(11): 942-955, 2007.
Non Patent Literature 2: Besnault, L., et al., J. Immunol., 167(2): 733-740, 2001.
Non Patent Literature 3: Mongini, P. A., et al., Blood, 92(10): 3756-3771, 1998.
Non Patent Literature 4: Miyazaki, K., et al., B r. J. Haematol., 142(4): 562-570, 2008.
Non Patent Literature 5: Cutrona, G., et al., ABSSUB-4465, 19th Congress of the European Hematology Association, 2014.

SUMMARY OF INVENTION

Technical Problem

Conventional anti-IgM monoclonal antibodies, when administered to a living body, are mostly bound by soluble IgM existing in blood in a large amount, and thus neutralized. Accordingly, the binding of the conventional anti-IgM antibodies to B cells expressing membrane-bound IgM is hardly said to be enough. Thus, the conventional anti-IgM antibodies are required to be administered in a large amount in order to bind to the B cells expressing membrane-bound IgM and exert a growth inhibition effect in the presence of soluble IgM.

In view of the foregoing, an object of the present invention is to provide an antibody which binds to membrane-bound IgM on the surface of B cells even in the presence of soluble IgM in blood, has a high binding activity to the B cells, and exerts a growth inhibition effect on the B cells.

Solution to Problem

The present inventors have conducted various studies to produce an antibody having a high binding activity to the membrane-bound IgM on the surface of B cells. As a result, the inventors have found that a bispecific antibody against IgM and a B cell surface antigen binds to membrane-bound IgM on the surface of B cells, even in the presence of a large amount of soluble IgM, and has a high binding activity to the B cells, and further exhibits excellent cell growth inhibition effect on the B cells, and consequently have completed the invention.

That is, the present invention provides the following [1] to [15].

[1] A bispecific antibody, which binds to IgM and a B cell surface antigen.
[2] The bispecific antibody according to [1], wherein the bispecific antibody comprises a first antigen-binding site which binds to the IgM, and a second antigen-binding site which binds to the B cell surface antigen.
[3] The bispecific antibody according to [1] or [2], wherein the B cell surface antigen is selected from the group consisting of HLA-DR, CD20, CD32b, CD37, CD38, CD52, CD81, a BAFF receptor, BCMA, and TACI.
[4] The bispecific antibody according to any of [1] to [3], wherein the bispecific antibody is a chimeric antibody, a humanized antibody or a human antibody.
[5] The bispecific antibody according to any of [1] to [4], wherein a variable region of the bispecific antibody comprises heavy chain CDR1 to CDR3 and light chain CDR1 to CDR3 of the following (a) to (f), and heavy chain CDR1 to CDR3 and light chain CDR1 to CDR3 of the following (g) to (1):

(a) the heavy chain CDR1 consisting of an amino acid sequence selected from the group consisting of SEQ ID NOs: 1, 48, 60, 66, 72, and 78; an amino acid sequence having an identity of 85% or more with the amino acid sequence selected from the group consisting of SEQ ID NOs: 1, 48, 60, 66, 72, and 78; or an amino acid sequence having deletion, substitution or addition of one to several amino acids in the amino acid sequence selected from the group consisting of SEQ ID NOs: 1, 48, 60, 66, 72, and 78, (b) the heavy chain CDR2 consisting of an amino acid sequence selected from the group consisting of SEQ ID NOs: 2, 49, 61, 67, 73, and 79; an amino acid sequence having an identity of 85% or more with the amino acid sequence selected from the group consisting of SEQ ID NOs: 2, 49, 61, 67, 73, and 79; or an amino acid sequence having deletion, substitution or addition of one to several amino acids in the amino acid sequence selected from the group consisting of SEQ ID NOs: 2, 49, 61, 67, 73, and 79, (c) the heavy chain CDR3 consisting of an amino acid sequence selected from the group consisting of SEQ ID NOs: 3, 50, 62, 68, 74, and 80; an amino acid sequence having an identity of 85% or more with the amino acid sequence selected from the group consisting of SEQ ID NOs: 3, 50, 62, 68, 74, and 80; or an amino acid sequence having deletion, substitution or addition of one to several amino acids in the amino acid sequence selected from the group consisting of SEQ ID NOs: 3, 50, 62, 68, 74, and 80, (d) the light chain CDR1 consisting of an amino acid sequence selected from the group consisting of SEQ ID NOs: 4, 51, 63, 69, 75, and 81; an amino acid sequence having an identity of 85% or more with the amino acid sequence selected from the group consisting of SEQ ID NOs: 4, 51, 63, 69, 75, and 81; or an amino acid sequence having deletion, substitution or addition of one to several amino acids in the amino acid sequence selected from the group consisting of SEQ ID NOs: 4, 51, 63, 69, 75, and 81, (e) the light chain CDR2 consisting of an amino acid sequence selected from the group consisting of SEQ ID NOs: 5, 52, 64, 70, 76, and 82; an amino acid sequence having an identity of 85% or more with the amino acid sequence selected from the group consisting of SEQ ID NOs: 5, 52, 64, 70, 76, and 82; or an amino acid sequence having deletion, substitution or addition of one to several amino acids in the amino acid sequence selected from the group consisting of SEQ ID NOs: 5, 52, 64, 70, 76, and 82, (f) the light chain CDR3 consisting of an amino acid sequence selected from the group consisting of SEQ ID NOs: 6, 53, 65, 71, 77, and 83; an amino acid sequence having an identity of 85% or more with the amino acid sequence selected from the group consisting of SEQ ID NOs: 6, 53, 65, 71, 77, and 83; or an amino acid sequence having deletion, substitution or addition of one to several amino acids in the amino acid sequence selected from the group consisting of SEQ ID NOs: 6, 53, 65, 71, 77, and 83, (g) the heavy chain CDR1 consisting of an amino acid sequence selected from the group consisting of SEQ ID NOs: 7, 13, 19, 25, 30, 36, 42, 84, 90, and 96; an amino acid sequence having an identity of 85% or more with the amino acid sequence selected from the group consisting of SEQ ID NOs: 7, 13, 19, 25, 30, 36, 42, 84, 90, and 96; or an amino acid sequence having deletion, substitution or addition of one to several amino acids in the amino acid sequence selected from the group consisting of SEQ ID NOs: 7, 13, 19, 25, 30, 36, 42, 84, 90, and 96, (h) the heavy chain CDR2 consisting of an amino acid sequence selected from the group consisting of SEQ ID NOs: 8, 14, 20, 26, 31, 37, 43, 85, 91, and 97; an amino acid sequence having an identity of 85% or more with the amino acid sequence selected from the group consisting of SEQ ID NOs: 8, 14, 20, 26, 31, 37, 43, 85, 91, and 97; or an amino acid sequence having deletion, substitution or addition of one to several amino acids in the amino acid sequence selected from the group consisting of SEQ ID NOs: 8, 14, 20, 26, 31, 37, 43, 85, 91, and 97, (i) the heavy chain CDR3 consisting of an amino acid sequence selected from the group consisting of SEQ ID NOs: 9, 15, and 21, FDY, and SEQ ID NOs: 32, 38, 44, 86, 92, and 98; an amino acid sequence having an identity of 85% or more with the amino acid sequence selected from the group consisting of SEQ ID NOs: 9, 15, and 21, FDY, and SEQ ID NOs: 32, 38, 44, 86, 92, and 98; or an amino acid sequence having deletion, substitution or addition of one to several amino acids in the amino acid sequence selected from the group consisting of SEQ ID NOs: 9, 15, and 21, FDY, and SEQ ID NOs: 32, 38, 44, 86, 92, and 98, (j) the light chain CDR1 consisting of an amino acid sequence selected from the group consisting of SEQ ID NOs: 10, 16, 22, 27, 33, 39, 45, 87, 93, and 99; an amino acid sequence having an identity of 85% or more with the amino acid sequence selected from the group consisting of SEQ ID NOs: 10, 16, 22, 27, 33, 39, 45, 87, 93, and 99; or an amino acid sequence having deletion, substitution or addition of one to several amino acids in the amino acid sequence selected from the group consisting of SEQ ID NOs: 10, 16, 22, 27, 33, 39, 45, 87, 93, and 99, (k) the light chain CDR2 consisting of an amino acid sequence selected from the group consisting of SEQ ID NOs: 11, 17, 23, 28, 34, 40, 46, 88, 94, and 100; an amino acid sequence having an identity of 85% or more with the amino acid sequence selected from the group consisting of SEQ ID NOs: 11, 17, 23, 28, 34, 40, 46, 88, 94, and 100; or an amino acid sequence having deletion, substitution or addition of one to several amino acids in the amino acid sequence selected from the group consisting of SEQ ID NOs: 11, 17, 23, 28, 34, 40, 46, 88, 94, and 100, and (l) the light chain CDR3 consisting of an amino acid sequence selected from the group consisting of SEQ ID NOs: 12, 18, 24, 29, 35, 41, 47, 89, 95, and 101; an amino acid sequence having an identity of 85% or more with the amino acid sequence selected from the group consisting of SEQ ID NOs: 12, 18, 24, 29, 35, 41, 47, 89, 95, and 101; or an amino acid sequence having deletion, substitution or addition of one to several amino acids in the amino acid sequence selected from the group consisting of SEQ ID NOs: 12, 18, 24, 29, 35, 41, 47, 89, 95, and 101.

[6] The bispecific antibody according to any of [1] to [5], wherein the bispecific antibody inhibits B cell growth.

[7] A pharmaceutical composition, comprising the bispecific antibody according to any of [1] to [6].

[8] An agent for treating a B cell-related disease, comprising the bispecific antibody according to any of [1] to [6] as an active ingredient.

[9] The agent for treating a B cell-related disease according to [8], wherein the B cell-related disease is a B cell tumor.

[10] Use of the bispecific antibody according to any of [1] to [6], for producing an agent for treating a B cell-related disease.

[11] The use according to [10], wherein the B cell-related disease is a B cell tumor.

[12] The bispecific antibody according to any of [1] to [6], for use in treating a B cell-related disease.

[13] The bispecific antibody according to [12], wherein the B cell-related disease is a B cell tumor.

[14] A method for treating a B cell-related disease, comprising administering an effective amount of the bispecific antibody according to any of [1] to [6].

[15] The method for treating a B cell-related disease according to [14], wherein the B cell-related disease is a B cell tumor.

Advantageous Effects of Invention

The anti-IgM/B cell surface antigen bispecific antibody of the present invention is characterized that it binds to membrane-bound IgM on the surface of the B cells even in the presence of a large amount of soluble IgM, and has a high binding activity to the B cells. In addition, the bispecific antibody of the present invention has reduced adverse effects. Thus, the bispecific antibody of the present invention, when administered to a patient suffering from a B cell-related disease, particularly, to a patient suffering from a B cell tumor, is not neutralized by soluble IgM in blood, and binds to membrane-bound IgM on the surface of B cells of interest, allowing to exert a cell growth inhibition activity against the B cells. In other words, it is possible to exert a growth inhibition activity against a B cell tumor. It is also possible to avoid the problems in association with massive doses of antibodies, such as burden of patients and increase of medical costs.

BRIEF DESCRIPTION OF DRAWINGS

FIG. 1 is a graph showing the numbers of IgM molecules and HLA-DR molecules present on HH cell membrane surface.

FIG. 2 is a graph showing the binding abilities of an anti-IgM antibody (1), an anti-HLA-DR antibody (1), and an anti-IgM (1)/HLA-DR (1) bispecific antibody to IgM and HLA-DR. The vertical axis shows the mean fluorescence intensity (MFI), and the horizontal axis shows the antibody concentration.

FIG. 3 is a graph showing the growth inhibition activities of the anti-IgM antibody (1), the anti-HLA-DR antibody (1), the anti-IgM (1)/HLA-DR (1) bispecific antibody and a negative control antibody against JeKo-1 cells. The vertical axis shows the growth inhibition activity, and the horizontal axis shows the concentration of soluble IgM added to the medium.

FIG. 4 is a graph showing the growth inhibition activities of the anti-IgM antibody (1), the anti-HLA-DR antibody (1), a combination of the anti-IgM antibody (1) and the anti-HLA-DR antibody (1), the anti-IgM (1)/HLA-DR (1) bispecific antibody and a negative control antibody against JeKo-1 cells. The vertical axis shows the growth inhibition activity, and the horizontal axis shows the concentration of soluble IgM added to the medium.

FIG. 5 is a graph showing the growth inhibition activities of the anti-IgM antibody (1), the anti-HLA-DR antibody (1), the anti-IgM (1)/HLA-DR (1) bispecific antibody and a negative control antibody against B104 cells. The vertical axis shows the growth inhibition activity, and the horizontal axis shows the concentration of soluble IgM added to the medium.

FIG. 6 is graphs showing the growth inhibition activities of the anti-IgM antibody (1), the anti-HLA-DR antibody (1), the anti-IgM (1)/HLA-DR (1) bispecific antibody and a negative control antibody against JeKo-1 cells, in the absence (left graph) or presence (right graph) of human serum. The vertical axis shows the cell viability.

FIG. 7 is a graph showing the growth inhibition activities of the anti-IgM antibody (1), an anti-CD20 antibody (1), an anti-IgM (1)/CD20 (1) bispecific antibody and a negative control antibody against JeKo-1 cells. The vertical axis shows the growth inhibition activity, and the horizontal axis shows the concentration of soluble IgM added to the medium.

FIG. 8 is a graph showing the growth inhibition activities of the anti-IgM antibody (1), an anti-CD20 antibody (2), an anti-IgM (1)/CD20 (2) bispecific antibody and a negative control antibody against JeKo-1 cells. The vertical axis shows the growth inhibition activity, and the horizontal axis shows the concentration of soluble IgM added to the medium.

FIG. 9 is a graph showing the growth inhibition activities of the anti-IgM antibody (1), the anti-CD20 antibody (1), the anti-IgM (1)/CD20 (1) bispecific antibody and a negative control antibody against B104 cells. The vertical axis shows the growth inhibition activity, and the horizontal axis shows the concentration of soluble IgM added to the medium.

FIG. 10 is graphs showing the growth inhibition activities of the anti-IgM antibody (1), the anti-CD20 antibody (1), the anti-IgM (1)/CD20 (1) bispecific antibody and a negative control antibody against JeKo-1 cells, in the absence (left graph) or presence (right graph) of human serum. The vertical axis shows the cell viability.

FIG. 11 is a graph showing the growth inhibition activities of the anti-IgM antibody (1), an anti-CD52 antibody, an anti-IgM (1)/CD52 bispecific antibody and a negative control antibody against B104 cells. The vertical axis shows the growth inhibition activity, and the horizontal axis shows the concentration of soluble IgM added to the medium.

FIG. 12 is charts showing the effects of the anti-IgM antibody (1), the anti-HLA-DR antibody (1), the anti-IgM (1)/HLA-DR (1) bispecific antibody and a negative control on the cell cycle of JeKo-1 cells, in the absence (each left chart) or presence (each right chart) of soluble IgM.

FIG. 13 is charts showing the effects of the anti-IgM antibody (1), the anti-HLA-DR antibody (1), the anti-IgM (1)/HLA-DR (1) bispecific antibody and a negative control on the cell cycle of JeKo-1 cells, in the absence (each left chart) or presence (each right chart) of human serum.

FIG. 14 is a graph showing the effects of an anti-IgM antibody, the anti-HLA-DR antibody (1), and an anti-IgM/HLA-DR (1) bispecific antibody on the number of rat B cells.

FIG. 15 is a graph showing the effect of the anti-IgM (1)/HLA-DR (1) bispecific antibody on the number of cynomolgus B cells in blood.

FIG. 16 is a graph showing the effect of the anti-IgM (1)/HLA-DR (1) bispecific antibody on the number of cynomolgus T cells in blood.

FIG. 17 is a graph showing the effect of the anti-IgM (1)/HLA-DR (1) bispecific antibody on the number of cynomolgus red blood cells in blood.

FIG. 18 is a graph showing the effect of the anti-IgM (1)/HLA-DR (1) bispecific antibody on the number of cynomolgus platelets in blood.

FIG. 19 is a graph showing the effect of the anti-IgM (1)/HLA-DR (1) bispecific antibody on cynomolgus body temperature.

FIG. 20 is a graph showing the growth inhibition activities of an anti-IgM antibody (2), the anti-HLA-DR antibody (1), an anti-IgM (2)/HLA-DR (1) bispecific antibody and a negative control antibody against B104 cells. The vertical axis shows the growth inhibition activity, and the horizontal axis shows the concentration of soluble IgM added to the medium.

FIG. 21 is a graph showing the growth inhibition activities of an anti-IgM antibody (3), the anti-HLA-DR antibody (1), an anti-IgM (3)/HLA-DR (1) bispecific antibody and a negative control antibody against JeKo-1 cells. The vertical axis shows the growth inhibition activity, and the horizontal axis shows the concentration of soluble IgM added to the medium.

FIG. 22 is a graph showing the growth inhibition activities of an anti-IgM antibody (4), the anti-HLA-DR antibody (1), an anti-IgM (4)/HLA-DR (1) bispecific antibody and a negative control antibody against B104 cells. The vertical axis shows the growth inhibition activity, and the horizontal axis shows the concentration of soluble IgM added to the medium.

FIG. 23 is a graph showing the growth inhibition activities of an anti-IgM antibody (5), the anti-HLA-DR antibody (1), an anti-IgM (5)/HLA-DR (1) bispecific antibody and a negative control antibody against B104 cells. The vertical axis shows the growth inhibition activity, and the horizontal axis shows the concentration of soluble IgM added to the medium.

FIG. 24 is a graph showing the growth inhibition activities of the anti-IgM antibody (1), an anti-HLA-DR antibody (2), an anti-IgM (1)/HLA-DR (2) bispecific antibody and a negative control antibody against B104 cells. The vertical axis shows the growth inhibition activity, and the horizontal axis shows the concentration of soluble IgM added to the medium.

FIG. 25 is a graph showing the growth inhibition activities of the anti-IgM antibody (1), an anti-CD38 antibody, an anti-IgM (1)/CD38 bispecific antibody and a negative control antibody against B104 cells. The vertical axis shows the growth inhibition activity, and the horizontal axis shows the concentration of soluble IgM added to the medium.

FIG. 26 is a graph showing the growth inhibition activities of the anti-IgM antibody (1), an anti-CD81 antibody, an anti-IgM (1)/CD81 bispecific antibody and a negative control antibody against JeKo-1 cells. The vertical axis shows the growth inhibition activity, and the horizontal axis shows the concentration of soluble IgM added to the medium.

FIG. 27 is a graph showing the apoptosis inducing effects of the anti-IgM antibody (1), the anti-HLA-DR antibody (1), the anti-IgM (1)/HLA-DR (1) bispecific antibody and a negative control antibody on Ramos cells. The vertical axis shows the percentage of apoptotic cells.

FIG. 28 is a graph showing the apoptosis inducing effects of the anti-IgM antibody (1), the anti-CD20 antibody (2), the anti-IgM (1)/CD20 (2) bispecific antibody and a negative control antibody on Ramos cells. The vertical axis shows the percentage of apoptotic cells.

FIG. 29 is a graph showing the apoptosis inducing effects of the anti-IgM antibody (1), the anti-CD38 antibody, the anti-IgM (1)/CD38 bispecific antibody and a negative control antibody on Ramos cells. The vertical axis shows the percentage of apoptotic cells.

DESCRIPTION OF EMBODIMENTS

As used herein, the "bispecific antibody" refers to a monoclonal antibody having at least two antigen-binding sites capable of binding to different antigens. Specifically, the "bispecific antibody" means, for example, a protein having two different antigen-recognition abilities, the protein comprising at least one first antigen-binding site formed of a heavy chain variable region of a first antibody and a light chain variable region of the first antibody; and at least one second antigen-binding site formed of a heavy chain variable region of a second antibody and a light chain variable region of the second antibody.

The form of the bispecific antibody is not particularly limited, and may be any form known in the art or may be other form as long as the form retains the specificity to two different antigens. The form of the bispecific antibody is roughly classified into two types, i.e., an IgG-like antibody and a low molecular antibody. The IgG-like antibody is a form retaining a Fc region. Examples of the IgG-like antibody include, but are not limited to, CrossMab, DAF (two-in-one), DAF (four-in-one), DutaMab, DT-IgG, knobs-into-holes, knobs-into-holes common LC, SEEDbody, Triomab, xk-body, DVD-Ig, IgG-scFv, and DuoBody. Since it retains the Fc region, the IgG-like antibody is expected to have an effector function such as ADCC or CDC, an easiness in purification, an improvement in stability, and a prolonged blood half-life. The low molecular antibody is a form typically having, as a basic structure, a Fv region consisting of a heavy chain variable region and a light chain variable region. Examples of the low molecular antibody include, but are not limited to, Diabody (Db), BiTE, DART, TandAb, scDb, triple body, miniantibody, minibody, scFv, tandem scFv, F(ab')2, and leucine zipper. The low molecular antigen is expected from its size to have an improvement in tissue penetration and a high productivity. Other examples of the form of the bispecific antibody include altered antibodies such as one in which the amino acid sequence has deletion, substitution or addition while retaining the ability to bind to an antigen, one in which a part or all of a sugar chain is deleted or added, one to which a linker or the like is added, one with which another protein is fused, and an antibody-drug conjugate (ADC) in which an antibody and a low molecular drug are linked via a linker. The form of the anti-IgM/B cell surface antigen bispecific antibody of the present invention (hereinafter, simply referred to as the bispecific antibody of the present invention) may be appropriately selected considering the intended use, easiness of production, or the like. However, in terms of the cytotoxic activity against B cells, the form retaining a Fc region is preferred.

The bispecific antibody of the present invention is characterized in that it comprises a first antigen-binding site which binds to IgM and a second antigen-binding site which binds to a B cell surface antigen.

Herein, IgM refers to immunoglobulin M. The animal species from which IgM is derived are not particularly limited, and examples thereof include human and non-human animals such as monkey, ape, mouse, rat, rabbit and goat. Of these, human is preferred. A first specificity for IgM is exhibited preferably by a site derived from an antibody against IgM, more preferably by a site derived from heavy chain and light chain variable regions of an antibody against IgM, and even more preferably by an antigen-binding site formed of heavy chain and light chain variable regions of an antibody against IgM.

The B cell surface antigen may be any antigen expressed on B cell surface except membrane-bound IgM, and is not particularly limited, but is preferably an antigen expressed on B cells of a living body suffering from a B cell-related disease, more preferably an antigen expressed on B cells of a living body suffering from a B cell tumor. The animal species from which the B cell surface antigen is derived are not particularly limited, and examples thereof include human and non-human animals such as monkey, ape, mouse, rat, rabbit and goat. Of these, human is preferred. Examples of the B cell surface antigen include, specifically, HLA-DR, HLA-DQ, HLA-DP, CD5, CD10, CD19, CD20, CD22, CD23, CD24, CD28, CD32b, CD37, CD38, CD40, CD43, CD45RA, CD45RO, CD52, CD53, CD54, CD72, CD73, CD74, CDw75, CDw76, CD77, CDw78, CD79a, CD79b, CD80, CD81, CD82, CD83, CDw84, CD85, CD86, CD138, CD272, a BAFF receptor, BCMA, TACI, and PD-1. Of these, HLA-DR, CD20, CD32b, CD37, CD38, CD52, CD81, a BAFF receptor, BCMA and TACI are preferred, HLA-DR, CD20, CD32b, CD37, CD38, CD52 and CD81 are more preferred, and HLA-DR, CD20, CD38, CD52 and CD81 are even more preferred. A second specificity for the B cell surface antigen is exhibited preferably by a site derived from an antibody against the B cell surface antigen, more preferably by a site derived from heavy chain and light chain variable regions of an antibody against the B cell surface antigen, and even more preferably by an antigen-binding site formed of heavy chain and light chain variable regions of an antibody against the B cell surface antigen.

Specifically, the bispecific antibody of the present invention comprises a polypeptide comprising a heavy chain variable region of an anti-IgM antibody having the first specificity, a polypeptide comprising a light chain variable region of the anti-IgM antibody having the first specificity, a polypeptide comprising a heavy chain variable region of an anti-B cell surface antigen antibody having the second specificity, and a polypeptide comprising a light chain variable region of the anti-B cell surface antigen antibody having the second specificity. More specifically, the bispecific antibody of the present invention comprises a polypeptide comprising a complementarity determining region (CDR) of a heavy chain variable region of an anti-IgM antibody having the first specificity, a polypeptide comprising a CDR of a light chain variable region of the anti-IgM antibody having the first specificity, a polypeptide comprising a CDR of a heavy chain variable region of an anti-B cell surface antigen antibody having the second specificity, and a polypeptide comprising a CDR of a light chain variable region of the anti-B cell surface antigen antibody having the second specificity.

The CDR refers to a sequence within a variable region which is very different between antibodies. Each of the heavy chain variable region and the light chain variable region has three CDRs, and the combination of these CDRs forms an antigen-binding site which determines the antigen specificity. The CDR is defined by sequence comparison in accordance with Kabat (see, Kabat, E. A., et al., Sequences of Proteins of Immunological Interest, 5th edition, Public Health Service, National Institutes of Health, Bethesda, Md., 1991). As defined by Kabat, heavy chain CDR1 is positioned around 31-35 residues, heavy chain CDR2 is positioned around 50-65 residues, and heavy chain CDR3 is positioned around 95-102 residues of the heavy chain variable region; and light chain CDR1 is positioned around 24-34 residues, light chain CDR2 is positioned around 50-56 residues, and light chain CDR3 is positioned around 89-97 residues of the light chain variable region.

In the bispecific antibody of the present invention, examples of the CDR which contributes to the first specificity for IgM include heavy chain CDR1 to CDR3 and light chain CDR1 to CDR3 shown in the following (a) to (f):

(a) the heavy chain CDR1 consisting of an amino acid sequence selected from the group consisting of SEQ ID NOs: 1, 48, 60, 66, 72, and 78; an amino acid sequence having an identity of 85% or more with the amino acid sequence selected from the group consisting of SEQ ID NOs: 1, 48, 60, 66, 72, and 78; or an amino acid sequence having deletion, substitution or addition of one to several amino acids in the amino acid sequence selected from the group consisting of SEQ ID NOs: 1, 48, 60, 66, 72, and 78, (b) the heavy chain CDR2 consisting of an amino acid sequence selected from the group consisting of SEQ ID NOs: 2, 49, 61, 67, 73, and 79; an amino acid sequence having an identity of 85% or more with the amino acid sequence selected from the group consisting of SEQ ID NOs: 2, 49, 61, 67, 73, and 79; or an amino acid sequence having deletion, substitution or addition of one to several amino acids in the amino acid sequence selected from the group consisting of SEQ ID NOs: 2, 49, 61, 67, 73, and 79, (c) the heavy chain CDR3 consisting of an amino acid sequence selected from the group consisting of SEQ ID NOs: 3, 50, 62, 68, 74, and 80; an amino acid sequence having an identity of 85% or more with the amino acid sequence selected from the group consisting of SEQ ID NOs: 3, 50, 62, 68, 74, and 80; or an amino acid sequence having deletion, substitution or addition of one to several amino acids in the amino acid sequence selected from the group consisting of SEQ ID NOs: 3, 50, 62, 68, 74, and 80, (d) the light chain CDR1 consisting of an amino acid sequence selected from the group consisting of SEQ ID NOs: 4, 51, 63, 69, 75, and 81; an amino acid sequence having an identity of 85% or more with the amino acid sequence selected from the group consisting of SEQ ID NOs: 4, 51, 63, 69, 75, and 81; or an amino acid sequence having deletion, substitution or addition of one to several amino acids in the amino acid sequence selected from the group consisting of SEQ ID NOs: 4, 51, 63, 69, 75, and 81, (e) the light chain CDR2 consisting of an amino acid sequence selected from the group consisting of SEQ ID NOs: 5, 52, 64, 70, 76, and 82; an amino acid sequence having an identity of 85% or more with the amino acid sequence selected from the group consisting of SEQ ID NOs: 5, 52, 64, 70, 76, and 82; or an amino acid sequence having deletion, substitution or addition of one to several amino acids in the amino acid sequence selected from the group consisting of SEQ ID NOs: 5, 52, 64, 70, 76, and 82, and (f) the light chain CDR3 consisting of an amino acid sequence selected from the group consisting of SEQ ID NOs: 6, 53, 65, 71, 77, and 83; an amino acid sequence having an identity of 85% or more with the amino acid sequence selected from the group consisting of SEQ ID NOs: 6, 53, 65, 71, 77, and 83; or an amino acid sequence having deletion, substitution or addition of one to several amino acids in the amino acid sequence selected from the group consisting of SEQ ID NOs: 6, 53, 65, 71, 77, and 83.

Furthermore, in the bispecific antibody of the present invention, examples of the CDR which contributes to the second specificity for B cell surface antigen include heavy chain CDR1 to CDR3 and light chain CDR1 to CDR3 shown in the following (g) to (1):

(g) the heavy chain CDR1 consisting of an amino acid sequence selected from the group consisting of SEQ ID NOs: 7, 13, 19, 25, 30, 36, 42, 84, 90, and 96; an amino acid sequence having an identity of 85% or more with the amino acid sequence selected from the group consisting of SEQ ID NOs: 7, 13, 19, 25, 30, 36, 42, 84, 90, and 96; or an amino acid sequence having deletion, substitution or addition of one to several amino acids in the amino acid sequence selected from the group consisting of SEQ ID NOs: 7, 13, 19, 25, 30, 36, 42, 84, 90, and 96, (h) the heavy chain CDR2 consisting of an amino acid sequence selected from the group consisting of SEQ ID NOs: 8, 14, 20, 26, 31, 37, 43, 85, 91, and 97; an amino acid sequence having an identity of 85% or more with the amino acid sequence selected from the group consisting of SEQ ID NOs: 8, 14, 20, 26, 31, 37, 43, 85, 91, and 97; or an amino acid sequence having deletion, substitution or addition of one to several amino acids in the amino acid sequence selected from the group consisting of SEQ ID NOs: 8, 14, 20, 26, 31, 37, 43, 85, 91, and 97, (i) the heavy chain CDR3 consisting of an amino acid sequence selected from the group consisting of SEQ ID NOs: 9, 15, and 21, FDY, and SEQ ID NOs: 32, 38, 44, 86, 92, and 98; an amino acid sequence having an identity of 85% or more with the amino acid sequence selected from the group consisting of SEQ ID NOs: 9, 15, and 21, FDY, and SEQ ID NOs: 32, 38, 44, 86, 92, and 98; or an amino acid sequence having deletion, substitution or addition of one to several amino acids in the amino acid sequence selected from the group consisting of SEQ ID NOs: 9, 15, and 21, FDY, and SEQ ID NOs: 32, 38, 44, 86, 92, and 98, (j) the light chain CDR1 consisting of an amino acid sequence selected from the group consisting of SEQ ID NOs: 10, 16, 22, 27, 33, 39, 45, 87, 93, and 99; an amino acid sequence having an identity of 85% or more with the amino acid sequence selected from the group consisting of SEQ ID NOs: 10, 16, 22, 27, 33, 39, 45, 87, 93, and 99; or an amino acid sequence having deletion, substitution or addition of one to several amino acids in the amino acid sequence selected from the group consisting of SEQ ID NOs: 10, 16, 22, 27, 33, 39, 45, 87, 93, and 99, (k) the light chain CDR2 consisting of an amino acid sequence selected from the group consisting of SEQ ID NOs: 11, 17, 23, 28, 34, 40, 46, 88, 94, and 100; an amino sequence selected from the group consisting of SEQ ID NOs: 12, 18, 24, 29, 35, 41, 47, 89, 95, and 101.

Preferred specific examples of the bispecific antibody having CDRs of (a) to (1) described above include, but are not limited to, an anti-IgM/HLA-DR bispecific antibody, an anti-IgM/CD20 bispecific antibody, an anti-IgM/CD32b bispecific antibody, an anti-IgM/CD37 bispecific antibody, an anti-IgM/CD38 bispecific antibody, an anti-IgM/CD52 bispecific antibody, an anti-IgM/CD81 bispecific antibody, an anti-IgM/BCMA bispecific antibody, an anti-IgM/BAFF receptor bispecific antibody and an anti-IgM/TACI bispecific antibody each having a CDR consisting of the amino acid sequence of SEQ ID NO described in Table 1, as shown in Examples described later.

TABLE 1

|  | Anti-IgM (1)/HLA-DR (1) bispecific antibody | | Anti-IgM (1)/CD20 (1) bispecific antibody | | Anti-IgM (1)/CD20 (2) bispecific antibody | | Anti-IgM (1)/CD32b bispecific antibody | |
|---|---|---|---|---|---|---|---|---|
| Heavy chain CDR1 | 1 | 7 | 1 | 13 | 1 | 19 | 1 | 25 |
| Heavy chain CDR2 | 2 | 8 | 2 | 14 | 2 | 20 | 2 | 26 |
| Heavy chain CDR3 | 3 | 9 | 3 | 15 | 3 | 21 | 3 | FDY |
| Light chain CDR1 | 4 | 10 | 4 | 16 | 4 | 22 | 4 | 27 |
| Light chain CDR2 | 5 | 11 | 5 | 17 | 5 | 23 | 5 | 28 |
| Light chain CDR3 | 6 | 12 | 6 | 18 | 6 | 24 | 6 | 29 |

|  | Anti-IgM (1)/CD37 bispecific antibody | | Anti-IgM (1)/CD52 bispecific antibody | | Anti-IgM (1)/BCMA bispecific antibody | | Anti-IgM/HLA-DR (1) bispecific antibody | |
|---|---|---|---|---|---|---|---|---|
| Heavy chain CDR1 | 1 | 30 | 1 | 36 | 1 | 42 | 48 | 7 |
| Heavy chain CDR2 | 2 | 31 | 2 | 37 | 2 | 43 | 49 | 8 |
| Heavy chain CDR3 | 3 | 32 | 3 | 38 | 3 | 44 | 50 | 9 |
| Light chain CDR1 | 4 | 33 | 4 | 39 | 4 | 45 | 51 | 10 |
| Light chain CDR2 | 5 | 34 | 5 | 40 | 5 | 46 | 52 | 11 |
| Light chain CDR3 | 6 | 35 | 6 | 41 | 6 | 47 | 53 | 12 |

|  | Anti-IgM (2)/HLA-DR (1) bispecific antibody | | Anti-IgM (3)/HLA-DR (1) bispecific antibody | | Anti-IgM (4)/HLA-DR (1) bispecific antibody | | Anti-IgM (5)/HLA-DR (1) bispecific antibody | |
|---|---|---|---|---|---|---|---|---|
| Heavy chain CDR1 | 60 | 7 | 66 | 7 | 72 | 7 | 78 | 7 |
| Heavy chain CDR2 | 61 | 8 | 67 | 8 | 73 | 8 | 79 | 8 |
| Heavy chain CDR3 | 62 | 9 | 68 | 9 | 74 | 9 | 80 | 9 |
| Light chain CDR1 | 63 | 10 | 69 | 10 | 75 | 10 | 81 | 10 |
| Light chain CDR2 | 64 | 11 | 70 | 11 | 76 | 11 | 82 | 11 |
| Light chain CDR3 | 65 | 12 | 71 | 12 | 77 | 12 | 83 | 12 |

|  | Anti-IgM (1)/HLA-DR (2) bispecific antibody | | Anti-IgM (1)/CD38 bispecific antibody | | Anti-IgM (1)/CD81 bispecific antibody | |
|---|---|---|---|---|---|---|
| Heavy chain CDR1 | 1 | 84 | 1 | 90 | 1 | 96 |
| Heavy chain CDR2 | 2 | 85 | 2 | 91 | 2 | 97 |
| Heavy chain CDR3 | 3 | 86 | 3 | 92 | 3 | 98 |
| Light chain CDR1 | 4 | 87 | 4 | 93 | 4 | 99 |
| Light chain CDR2 | 5 | 88 | 5 | 94 | 5 | 100 |
| Light chain CDR3 | 6 | 89 | 6 | 95 | 6 | 101 |

Each number represents SEQ ID NO.

acid sequence having an identity of 85% or more with the amino acid sequence selected from the group consisting of SEQ ID NOs: 11, 17, 23, 28, 34, 40, 46, 88, 94, and 100; or an amino acid sequence having deletion, substitution or addition of one to several amino acids in the amino acid sequence selected from the group consisting of SEQ ID NOs: 11, 17, 23, 28, 34, 40, 46, 88, 94, and 100, and (l) the light chain CDR3 consisting of an amino acid sequence selected from the group consisting of SEQ ID NOs: 12, 18, 24, 29, 35, 41, 47, 89, 95, and 101; an amino acid sequence having an identity of 85% or more with the amino acid sequence selected from the group consisting of SEQ ID NOs: 12, 18, 24, 29, 35, 41, 47, 89, 95, and 101; or an amino acid sequence having deletion, substitution or addition of one to several amino acids in the amino acid In the above (a) to (1), the identity of the amino acid sequence is 85% or more, preferably 90% or more, more preferably 95% or more, and even more preferably 98% or more. The number of amino acids deleted, substituted or added in the amino acid sequence described above is preferably 1 to 10, more preferably 1 to 5, and even more preferably 1 to 3. The CDR consisting of the amino acid sequence having an identity of 85% or more with the amino acid sequence set forth in any of SEQ ID NOs: 1 to 53 and 60 to 101 or the amino acid sequence consisting of FDY, or the CDR consisting of the amino acid sequence having deletion, substitution or addition of one to several amino acids in the amino acid sequence set forth in any of SEQ ID NOs: 1 to 53 and 60 to 101 or the amino acid sequence consisting of FDY may be prepared by a known method such as site-directed mutagenesis, random mutagenesis, a chain shuffling method, and a CDR walking method.

The identity of the amino acid sequence, when aligning two amino acid sequences, refers to the percentage of the number of positions at which the identical amino acid residues are present in the both sequences with respect to the number of amino acid residues in the sequence of full-length. For example, the identity of the amino acid sequences can be calculated by using a homology analysis (Search homology) program in accordance with Lipman-Pearson method (Lipman, D. J. and Pearson, W. R., Science, 227 (4693): 1435-1441, 1985) with a genetic information processing software GENETYX and defining a parameter Unit Size to compare as 2.

The "amino acid" is used in its broadest sense to include not only natural amino acids but also non-natural amino acids such as amino acid variants and derivatives. Those skilled in the art, in view of this broad definition, can consider, as an amino acid in the present specification, the following compounds: natural proteinogenic L-amino acids; D-amino acids; chemically modified amino acids such as amino acid variants and derivatives; natural non-proteinogenic amino acids such as norleucine, A-alanine, and ornithine; and chemically synthesized compounds having properties which are known in the art to be characteristic of an amino acid. Examples of the non-natural amino acids include α-methyl amino acids such as α-methyl alanine; D-amino acids; histidine-like amino acids such as 2-amino-histidine, β-hydroxy-histidine, homo-histidine, α-fluoromethyl-histidine and α-methyl-histidine; amino acids having an extra methylene in the side chain ("homo" amino acids); and amino acids in which a carboxylic acid functional group in the side chain is substituted by a sulfonic acid group such as cysteic acid.

The bispecific antibody of the present invention also includes an antibody to which a modification such as glycosylation is made. Examples of such a modified antibody include an antibody in which one or more N-linked oligosaccharides are linked to the Fc region, and N-acetylglucosamine in the reducing terminal of the N-linked oligosaccharide is not fucosylated. The N-acetylglucosamine in the reducing terminal of the N-linked oligosaccharide may be fucosylated, but it is known that ADCC significantly increases when not fucosylated compared to when fucosylated. Furthermore, the bispecific antibody of the present invention also includes an altered antibody such as an IgG1/IgG3 chimeric antibody in which CH2 and CH3 regions of IgG1 are replaced with CH2 and CH3 regions of IgG3, respectively. It is known that this antibody has stronger complement binding ability than IgG1 and IgG3, and has high CDC. The improvement of the cytotoxic activity allows to reduce dose and adverse effects when using the antibody as a medicament, and also may allow to reduce costs of medical treatment.

The immunoglobulin class of the bispecific antibody of the present invention is not particularly limited, and the bispecific antibody of the present invention may be any immunoglobulin class selected from the group consisting of IgG, IgM, IgA, IgE, IgD, and IgY. However, in view of the easiness of purification or the like, it is preferred that the immunoglobulin class is IgG. Furthermore, the bispecific antibody of the present invention includes any isotype of the antibody (e.g., IgG1, IgG2, IgG3, and IgG4).

The bispecific antibody of the present invention may be a non-human animal antibody, a chimeric antibody, a humanized antibody or a human antibody. Examples of the non-human animal antibody include a monkey, ape, mouse, rat, rabbit or goat antibody, and of these, a mouse antibody is preferable.

Herein, the "chimeric antibody" refers to an antibody formed by genetically engineering the constant region of an antibody from non-human animal which specifically binds to an antigen so as to have the same constant region as a human antibody. It is preferably a chimeric antibody made by ligating a variable region of a mouse antibody to a constant region of a human antibody. Furthermore, the "humanized antibody" refers to an antibody formed by genetically engineering the primary structure other than heavy chain and light chain CDRs of an antibody from non-human animal which specifically binds to an antigen so as to have a corresponding primary structure of a human antibody. Furthermore, the "human antibody" refers to an antibody which is an expression product of an antibody gene fully derived from human.

The antibody which provides the first specificity or second specificity to the bispecific antibody of the present invention may be a known antibody or may be produced by any method well known in the art.

In the case of the antibody being a polyclonal antibody, the antibody is obtained by injecting an immunogen and optionally injecting an adjuvant several times into an animal body such as a mouse body in a suitable route such as subcutaneous or intraperitoneal route, to yield antibodies in the animal body; isolating antisera containing the yielded antibodies from the immunized animal; and screening the antisera for the presence of an antibody having the desired specificity using a method well known in the art such as ELISA, Western blot, or radioimmunoassay. Examples of the immunogen include IgM, a B cell surface antigen protein, a partial peptide thereof, and a cell stably expressing them.

In the case of the antibody being a monoclonal antibody, the antibody can be obtained from a population of substantially homogeneous antibodies using a hybridoma method which was first described by Kohler, G. and Milstein, C., Nature, 256 (5517): 495-497, 1975. Specifically, the monoclonal antibody can be obtained by collecting spleen cells from the immunized animal, fusing the spleen cells with myeloma cells to prepare hybridoma cells producing monoclonal antibodies. From the prepared hybridoma cells, a hybridoma cell which produces antibodies recognizing a protein of interest may be selected by a method well known in the art such as ELISA, Western blot, or radioimmunoassay. The hybridoma secreting the desired antibody is cloned, and cultured under a suitable condition, and then the soluble antibody is collected and may be purified using a method well known in the art such as ion-exchange column or affinity chromatography. Alternatively, the monoclonal antibody can be made by a recombinant DNA method (U.S. Pat. No. 4,816,567).

The nucleic acid encoding the antibody or each region such as a variable region comprised therein can be obtained and the nucleotide sequence thereof can be determined by a method known to those skilled in the art. For example, the nucleic acid can be obtained by hybridization or polymerase chain reaction (PCR), using oligonucleotide probes or primers capable of binding specifically to genes encoding the heavy chain and light chain described in literatures. The hybridoma cell producing the monoclonal antibody described above can be used as a source of DNA in these methods. The "nucleic acid" is not particularly limited by the chemical structure and acquisition route thereof, and examples of the nucleic acid include gDNA, cDNA, a chemically synthesized DNA and mRNA.

The isolated DNA is introduced into an expression vector. Then, by transfecting a suitable host cell with the obtained expression vector, the monoclonal antibody or a region comprised therein can be expressed in the recombinant host cell.

Here, the "expression vector" refers to a fragment of DNA (usually double-stranded DNA), and the DNA can comprise a fragment of foreign DNA inserted therein. The foreign DNA is defined as a heterologous DNA, which is a DNA not found in the host cell to be transfected in nature. The vector is employed to introduce a foreign or heterologous DNA into a suitable host cell. Once the vector enters the host cell, the vector is able to replicate independently from the DNA of the host chromosome, and several copies of the vector and the foreign DNA inserted therein may be generated. Furthermore, the vector may comprise elements essential to allowing translation of foreign DNA into a polypeptide. Therefore, it is possible to quickly biosynthesize many molecules of the polypeptide encoded by the foreign DNA.

Such a vector represents a DNA construct comprising an appropriate regulatory sequence and a DNA sequence operatively linked thereto (i.e., they are linked to be able to express a protein encoded by the foreign DNA), so that a protein encoded by the DNA sequence is expressed in a suitable host. Examples of the regulatory sequence include a promoter for transcription, an optional operator sequence to regulate such transcription, a sequence encoding a suitable mRNA ribosome binding site, an enhancer, a polyadenylation sequence, and a sequence which regulates termination of transcription or translation. Furthermore, the vector can comprise various sequences known to those skilled in the art, for example, a restriction enzyme cleavage site, a marker gene (selection gene) such as a drug resistance gene, a signal sequence, a leader sequence, or the like, as necessary. One skilled in the art can appropriately select and use these various sequences or elements depending on the conditions such as the type of foreign DNA, a host cell to be used and culture medium.

The vector can be in any form such as a plasmid, a phage particle or a simple insert to the host genome. The vector may be one which, once introduced into a suitable host by transformation, is able to replicate and function independently from the genome of the host. Alternatively, the vector may be one which is integrated into the genome of the host.

PCR reaction can be performed by a known method in the art or a substantially the same or an altered method of the known method. For example, PCR reaction can be performed in accordance with the method described in Saiki, R. K., et al., Science, 230(4732): 1350-1354, 1985; Saiki, R. K., et al., Science, 239(4839): 487-491, 1988; Erlich, H. A., ed., PCR Technology, Stockton Press, New York, N.Y., 1989; Glover, D. M. and Hames, B. D., ed., DNA Cloning, 2nd edition, Vol. 1, The Practical Approach Series, IRL Press, Oxford, U K, 1995; Innis, M. A., et al., ed., PCR Protocols, Academic Press, New York, N.Y., 1990; McPherson, M. J., et al., ed., PCR, IRL Press, Oxford, U K, 1991; Frohman M. A., et al., Proc. Natl. Acad. Sci. USA, 85(23), 8998-9002, 1988 or the like, or an altered method thereof. Furthermore, a PCR method can be performed using a commercially available kit suitable therefor, and performed in accordance with the instruction provided by a kit manufacturer or kit distributor.

Hybridization can be performed referring to Grossman, L., et al., ed., Methods in Enzymology, Vol. 29, Nucleic Acids and Protein Synthesis, Part E, Academic Press, New York, N.Y., 1974 or the like. Sequencing of nucleic acids such as DNA can be performed referring to, for example, Sanger, F., et al., Proc. Natl. Acad. Sci. USA, 74(12):5463-5467, 1977 or the like. Furthermore, the general recombinant DNA technique can be performed referring to Sambrook, J., et al., ed., Molecular Cloning, 2nd edition, Cold Spring Harbor Laboratory Press, Cold Spring Harbor, N.Y., 1989., and, Glover, D. M. and Hames, B. D., ed., DNA Cloning, 2nd edition., Vol. 1 to 4, The Practical Approach Series, IRL Press, Oxford, U K, 1995 or the like.

Nucleic acids encoding the thus-obtained antibody or each region comprised therein can be altered appropriately so as to encode a desired peptide or amino acids, depending on the purpose, by means known to those skilled in the art. Such means to genetically alter or modify DNA is reviewed in McPherson, M. J., ed., Mutagenesis, IRL Press, Oxford, U K, 1991. Examples of the means include a position designated mutagenesis method (site-directed mutagenesis method), a cassette mutagenesis method and a PCR mutagenesis method.

Herein, the "alternation" of the nucleic acid refers to an insertion, deletion or substitution of a base in at least one codon encoding an amino acid residue in the obtained original nucleic acid. For example, there is a method of altering the amino acid sequence constituting the polypeptide itself by substituting a codon encoding the original amino acid residue with a codon encoding another amino acid residue. Furthermore, there is a method of altering the nucleic acid without changing the amino acid itself so that a codon suitable for the host cell (optimal codon) is used. By altering to the optimal codon in this way, it is possible to provide an improvement in expression efficiency of a polypeptide in a host cell.

As the host cell, any cell known to those skilled in the art can be used. Examples of a typical host cell include a prokaryotic cell such as Escherichia coli (E. coli), and an eukaryotic cell such as a mammalian cell, e.g., a Chinese hamster ovary cell (CHO cell) and a human-derived cell, a yeast or an insect cell.

Antibody molecules obtained by expression or the like in such a host cell are generally recovered as secreted polypeptides from the culture medium. When they are expressed as polypeptides without a secretory signal, they can be recovered from a lysate of the host cell.

Purification of the antibody molecules can be performed by appropriately combining any method known to those skilled in the art. For example, the purification can be made suitably by centrifugation, hydroxyapatite chromatography, gel electrophoresis, dialysis, fractionation on an ion-exchange column, ethanol precipitation, reverse phase HPLC, chromatography on silica, heparin sepharose chromatography, anion or cation resin chromatography (such as polyaspartic acid column), chromatofocusing, SDS-PAGE, ammonium sulfate precipitation, and affinity chromatography.

The antibody which provides a first specificity or a second specificity to the bispecific antibody of the present invention may be a chimeric antibody consisting of heavy chain and light chain variable regions of a non-human animal antibody such as a mouse antibody, and heavy chain and light chain constant regions of a human antibody. The antibody can be obtained, for example, by ligating a DNA encoding the variable region of a mouse antibody to a DNA encoding the constant region of a human antibody, integrating the resultant to an expression vector, and introducing the obtained vector into a host to produce an antibody.

Alternatively, the antibody may be a humanized antibody which is obtained by grafting CDRs of heavy and light chain of a non-human animal antibody, e.g., a mouse antibody, into CDRs of a human antibody. The humanized antibody is also referred to as a reshaped human antibody. General gene recombination techniques for obtaining the humanized antibody are known. Specifically, a humanized antibody is obtained by synthesizing, by a PCR method, a DNA sequence which is designed to connect CDRs of a mouse antibody and a framework region (FR) of a human antibody from several oligonucleotides each prepared to have an overlap portion at the end. The obtained DNA is ligated to a DNA encoding a human antibody constant region, and then the resultant is integrated into an expression vector, and the obtained vector is introduced into a host to produce a humanized antibody (EP 239 400, WO96/02576). The FR of a human antibody to be ligated via the CDRs is selected so that the CDRs form a favorable antigen-binding site. If necessary, the amino acids of the FR of the variable region of the antibody may be replaced so that the CDRs of the reshaped human antibody form an appropriate antigen-binding site (Sato, K. et al., Cancer Res., 53(4), 851-056, 1993).

Alternatively, the antibody may be a human antibody. The human antibody can be obtained, for example, by sensitizing a human lymphocyte with an antigen of interest or a cell expressing the antigen of interest in vitro, fusing the sensitized lymphocyte with a human myeloma cell, and screening for a desired human antibody having a binding activity to the antigen of interest (JP—B-H01-59878). It is also possible to obtain a desired human antibody by immunizing a transgenic animal having all repertoires of human antibody genes with an antigen of interest (WO93/12227, WO92/03918, WO94/02602, WO94/25585, WO96/34096, WO96/33735). Furthermore, it is also known a technique for obtaining a human antibody by panning using a human antibody library. For example, a variable region of a human antibody can be expressed as a single chain antibody (scFv) on the surface of a phage by a phage display method, and a phage that binds to an antigen can be selected. By analyzing a gene of the selected phage, a DNA sequence encoding the variable region of the human antibody that binds to the antigen can be determined. When the DNA sequence of the scFv that binds to the antigen is determined, it is possible to prepare an appropriate expression vector into which the determined sequence is integrated to thereby obtain a human antibody. These methods are already well known, and references can be made to WO92/01047, WO92/20791, WO93/06213, WO93/11236, WO93/19172, WO95/01438, WO95/15388. Furthermore, it is possible to produce a human antibody with a high affinity (in the nM order) by a chain shuffling method (Marks, J. D., et al., Bio/Technol., 10(7): 779-783, 1992). As a method for constructing a very large phage library, there are known methods such as a combinatorial infection and in vivo recombination (Waterhouse, P., et al., Nuc. Acids Res., 21(9): 2265-2266, 1993).

The combination of an antibody which provides the first specificity and an antibody which provides the second specificity to the bispecific antibody of the present invention may be any combination of a non-human animal antibody, a chimeric antibody, a humanized antibody and a human antibody.

The bispecific antibody of the present invention can be prepared in accordance with various methods known in the art. Examples of the method for producing the IgG-like bispecific antibody include a quadroma method comprising fusing two different hybridomas each producing a monoclonal antibody, and purifying an antibody of interest from the produced antibodies (for example, Milestein, C. and Cuello, A. C., Nature, 305 (5934): 537-540, 1983); a chemical synthesis method comprising reducing the disulfide bond in the hinge region of two different antibodies, then chemically treating the reduced antibodies to prevent allogeneic reassociation, and binding the two antibodies by a crosslinking agent to obtain a desired bispecific antibody (Nitta, T., et al, Lancet, 335 (8686): 368-371, 1990); and a genetic recombination method comprising introducing a heavy chain gene and a light chain gene of an antibody having the first specificity and a heavy chain gene and a light chain gene of an antibody having the second specificity into a cell, and co-expressing these genes to obtain an antibody of interest. In the genetic recombination method, by performing a transfection of a suitable host cell collectively with four vectors each comprising only one gene or two vectors each comprising heavy chain and light chain genes, it is possible to express the bispecific antibody in the recombinant host cell. The production, purification or the like of the bispecific antibody may be carried out according to the above-described production, purification or the like of antibodies.

However, in the quadroma method or the method of co-expressing four genes, in addition to the antibody having a structure of interest in which the heavy and light chains derived from an antibody having the first specificity for IgM are associated and the heavy and light chains derived from an antibody having the second specificity for a B cell surface antigen are associated, and these heavy chains are associated each other, other antibodies such as an antibody in which the heavy and light chains from different origins are associated, and an antibody in which the heavy chains from the same origin are associated are produced, resulting in a total of 10 different antibodies. In this case, a complicated operation for purification is necessary in order to obtain the antibody of interest, and the produced amount of the antibody of interest is not enough.

Thus, in the production method of the bispecific antibody, a technique to facilitate purification can be applied. As such a technique, it is known a method of purifying the antibody of interest using a Protein A column (WO98/050431). The method utilizes properties that, when heavy and light chains from mouse and rat coexist, the association between those from different origins does not occur, and IgG2 heavy chain derived from the mouse binds to Protein A while IgG2 derived from the rat hardly binds to Protein A. Alternatively, a method for efficiently purifying an antibody of interest which utilizes the difference in Protein A binding ability between IgG1 and IgG3 is also available.

It is also possible to apply a technique to promote a heterogeneous association between heavy chains derived from different origins. As such a technique, for example, there is a known method of promoting a heterogeneous association between heavy chains by replacing an amino acid of CH3 region of one heavy chain with a large amino acid (knob mutation) and replacing a corresponding amino acid of CH3 region of the other heavy chain with a sterically complementary small amino acid (hole mutation) (Ridgway, J. B., et al., Protein Eng., 9(7): 617-621, 1996). There is also a known method of introducing a charge mutation in the interface of CH3 regions of the heavy chains for promoting heterogeneous association between the heavy chains while inhibiting homogeneous association by the charge repulsion (Gunasekaran, K., et al., J. Biol. Chem., 285(25): 19637-19646, 2010). Furthermore, there is also a known method of promoting heterogeneous association between heavy chains by combining β-strand parts of CH3 regions of IgG and IgA each other (Davis, J. H., et al., Protein Eng. Des. Sel., 23 (4): 195-202, 2010).

It is also possible to apply a technique to avoid an association between heavy and light chains derived from different origins. As such a technique, there is a known method of selecting a light chain capable of being associated in common with heavy chains from different origins by a phage display method (Merchant, A. M., et al., Nat. Biotechnol., 16(7):677-681, 1998). There is also a known method of promoting an association of heavy and light chains from the same origin by replacing a heavy chain CH1 region with a light chain CL region derived from the same origin (Schaefer, W., et al., Proc. Natl. Acad. Sci. USA, 108(27):11187-11192, 2011). There is also a known method of producing a bispecific antibody by expressing two different antibody components each comprising one heavy chain and one light chain in two different host cells separately, followed by purification, and assembling them in vitro (Jackman, J., et al., J. Biol. Chem. 285(7):20850-20859, 2010). Furthermore, there is also a known method of efficiently producing an antibody having a specific combination of heavy and light chains by introducing a non-natural disulfide bond between the heavy and light chains (WO2014/069647).

These known techniques may be used alone or may be used in combination of two or more techniques. Furthermore, these known techniques may be applied separately to two different heavy chains.

In the production of the low molecular bispecific antibody of the present invention, a single chain Fv (scFv) in which the heavy chain variable region (VH) and the light chain variable region (VL) are linked by a linker, is often used as the basic unit. Arrangement of the VL and VH in the scFv may be one in which VL, linker and VH are arranged in this order from the N-terminus (VL-Linker-VH construct), or one in which VH, linker and VL are arranged in this order from the N-terminus (VH-Linker-VL construct). By co-expressing two scFvs, it is possible to obtain a bispecific antibody known as a diabody (Holliger, P., et al., Proc. Natl. Acad. Sci. USA, 90(14):6444-6448, 1993). The low molecular bispecific antibody in the form other than diabody can also be prepared in accordance with the methods known in the art.

The bispecific antibody of the present invention binds to membrane-bound IgM present on the surface of B cells, has a high binding activity with the B cells, and as shown in Examples described below, the bispecific antibody exhibits an excellent cell growth inhibition activity against the B cells, even in the presence of a large amount of soluble IgM, by arresting the cell cycle of the B cells which express IgM on the surface. Furthermore, the bispecific antibody of the present invention exhibits an excellent apoptosis inducing effect on the B cells as shown in Examples described later. It is known that an anti-IgM antibody induces apoptosis against B cell tumor cell lines. However, unexpectedly, the apoptosis inducing effect of the bispecific antibody of the present invention has a significantly stronger than each apoptosis inducing effect of the anti-IgM antibody which provides the first specificity to the bispecific antibody and the anti-B cell surface antigen antibody which provides the second specificity to the bispecific antibody. In addition, the bispecific antibody of the present invention has reduced adverse effects.

In the present invention, the binding activity of the antibody with an antigen can be determined by using a known method such as ELISA, a flow cytometry method, and a surface plasmon resonance (SPR) method. With ELISA, the measurement may be performed, for example, by immobilizing an antigen to a plate, adding the bispecific antibody of the present invention to the plate to react with the antigen, subjecting the resultant to reaction with a secondary antibody such as an anti-IgG antibody labeled with an enzyme such as horseradish peroxidase (HRP), and measuring absorbance with addition of a chromogenic substrate (e.g., TMB chromogenic substrate). When using the flow cytometry method, the measurement may be performed, for example, by binding the bispecific antibody of the present invention to an unlabeled target of evaluation (e.g., a biological sample of an individual, an organ, a tissue, a cell, or a fragment thereof), subjecting the resultant to reaction with a fluorochrome-conjugated secondary antibody or directly labelling the bispecific antibody of the present invention with a fluorescent dye (e.g., Alexa Fluor 647), and detecting the fluorescence by a flow cytometer. When using the SPR method, it is possible to measure the binding activity of the antibody and the antigen in more detail. For example, the measurement may be performed using a BIAcore system by immobilizing an antigen on a sensor chip, supplying a solution comprising the bispecific antibody of the present invention to the surface of the sensor chip for a fixed time, subsequently supplying a buffer, and monitoring the association and dissociation between the bispecific antibody of the present invention and the antigen to calculate an association rate constant ($k_a$), a dissociation rate constant ($k_d$), and a dissociation constant ($K_D = k_d/k_a$). $K_D$ is an index of the affinity. The smaller the $K_D$, the stronger the affinity of the antibody to the antigen. Alternatively, the affinity can be represented by an association constant ($K_A = 1/K_D$).

It is preferred that the bispecific antibody of the present invention binds to a B cell at $K_D$ of, for example, $10^{-6}$ M or less, $10^{-7}$ M or less, $10^{-8}$ M or less, $10^{-9}$ or less, $10^{-10}$ M or less, or $10^{-11}$ M or less. In the present invention, the "cell cycle arrest" means that the progression of the cell cycle is stopped at G1 phase. The cell cycle can be analyzed in accordance with a conventional method, for example, by measuring the DNA content of the cell by a flow cytometer.

In the present invention, the "cell growth inhibition activity" means that, by administering the bispecific antibody of the present invention to B cells that express IgM on the cell surface, the growth of the B cells is inhibited. More specifically, the cell growth inhibition activity is calculated by Equation (1) in Example 4 described below.

In the present invention, the "apoptosis inducing effect" means an effect on a cell to induce a cell death which is positively caused by the cell itself. When the apoptosis is induced, the cell shrinks, the aggregation of nucleus and the fragmentation of DNA occurs, and ultimately the cell becomes an apoptotic body which is phagocytosed by macrophages or the like. The apoptosis inducing effect can be evaluated in accordance with a conventional method, for example, by detecting a structural change in cell membrane, an aggregation of nucleus, a fragmentation of DNA, or a caspase activity.

As described above, the bispecific antibody of the present invention has a high binding ability to the membrane-bound IgM present on the surface of B cells, and exhibits an excellent cell growth inhibition activity against the B cells. Accordingly, the bispecific antibody of the present invention is useful as an agent for preventing or treating a B cell-related disease. Examples of the B cell-related disease include an autoimmune disease, an inflammatory disease, an allergic disease, a graft versus host disease, and a B cell tumor. Examples of the autoimmune disease include multiple sclerosis, rheumatoid arthritis, systemic lupus erythematosus, psoriasis, dermatitis, systemic scleroderma or sclerosis, symptoms associated with inflammatory bowel disease, Crohn's disease, ulcerative colitis, respiratory distress syndrome, adult respiratory distress syndrome (ARDS), dermatitis, meningitis, encephalitis, uveitis, colitis, glomerulonephritis, a condition due to allergies, eczema, asthma, pathologies and chronic inflammatory response associated with infiltration of T cells, atherosclerosis, leukocyte adhesion deficiency, diabetes mellitus, Raynaud's syndrome, autoimmune thyroiditis, allergic encephalomyelitis, Sjogren's syndrome, juvenile onset diabetes, an immune response associated with acute and delayed hypertension mediated by T lymphocytes and cytokines, tuberculosis, sarcoidosis, polymyositis, granulomatosis, vasculitis, pernicious anemia (Addison's disease), a disease associated with the extravasation leukocytes, central nervous system (CNS) inflammatory disease, multiple organ injury syndrome, hemolytic anemia, myasthenia gravis, antigen-antibody complex mediated disease, anti-glomerular basement membrane disease, anti-phospholipid syndrome, allergic neuritis, Graves' disease, Lambert-Eaton myasthenic syndrome, pemphigoid, pemphigus, autoimmune polyglandular endocrine disorder, Reiter's disease, stiff-man syndrome, Behcet's syndrome, giant cell arteritis, immune complex nephritis, IgA nephropathy, IgM polyneuropathy, chronic fatigue syndrome, idiopathic thrombocytopenic purpura (ITP) and autoimmune thrombocytopenia. Examples of the inflammatory disease include type 2 diabetes and periodontal disease. Examples of the allergic disease include hemolytic anemia due to incompatible blood transfusion, autoimmune hemolytic anemia, drug-induced hemolytic anemia, idiopathic thrombocytopenic purpura, granulocytopenia, Goodpasture syndrome, serum sickness, hypersensitivity pneumonitis, allergic bronchopulmonary aspergillosis, multiple sclerosis, rheumatoid arthritis, and glomerulonephritis. Examples of the B cell tumor include a progenitor B cell tumor and a mature B cell tumor. Examples of the progenitor B cell tumor include B cell lymphoblastic leukemia/lymphoma. Examples of the mature B cell tumor include chronic lymphocytic leukemia/small lymphocytic lymphoma, monoclonal B cell lymphocytosis, B cell prolymphocytic leukemia, splenic marginal zone lymphoma, hairy cell leukemia, splenic B cell lymphoma/leukemia, lymphoplasmacytic lymphoma, monoclonal gammopathy (MGUS), heavy chain disease, γ heavy chain disease, α heavy chain disease, IgM type MGUS, IgG/IgA type MGUS, plasmacytoma, solitary plasmacytoma of bone, extraosseous plasmacytoma, monoclonal immunoglobulin deposition disease, mucosa-associated lymphoid tissue type extra nodal marginal zone lymphoma (MALT lymphoma), nodal marginal zone lymphoma, follicular lymphoma, pediatric follicular lymphoma, large B cell lymphoma with IRF4 translocation, primary cutaneous follicle center lymphoma, mantle cell lymphoma, diffuse large B cell lymphoma (DLBCL), T cell/histiocyte-rich large B cell lymphoma, primary CNS DLBCL, primary cutaneous DLBCL, EBV-positive DLBCL, EBV-positive mucocutaneous ulcer, DLBCL associated with chronic inflammation, lymphomatoid granulomatosis, mediastinal (thymic) large B cell lymphoma, intravascular large B cell lymphoma, ALK-positive large B cell lymphoma, plasmablastsic lymphoma, primary effusion lymphoma, HHV8 positive DLBCL, Burkitt lymphoma, Burkitt-like lymphoma with 11q aberration, high-grade B cell lymphoma with MYC and BCL2 and/or BCL6 rearrangement, high-grade B cell lymphoma, and B cell lymphoma, unclassifiable, with features intermediate between DLBCL and classical Hodgkin lymphoma. Of these, the B cell-related disease is preferably a mature B cell tumor, more preferably chronic lymphocytic leukemia/small lymphocytic lymphoma, mantle cell lymphoma, follicular lymphoma, DLBCL and plasmacytoma, even more preferably chronic lymphocytic leukemia/small lymphocytic lymphoma and DLBCL.

A pharmaceutical composition comprising the bispecific antibody of the present invention can be formulated with a pharmaceutically acceptable carrier well known in the art, by mixing, dissolving, emulsifying, encapsulating, lyophilizing, or the like.

For oral administration, the bispecific antibody of the present invention can be formulated into a dosage form such as a liquid in which an effective amount of the bispecific antibody is dissolved in a diluent such as water or physiological saline; a capsule, a granule, a powder or a tablet in which an effective amount of the bispecific antibody is comprised as solid or granules; a suspension in which an effective amount of the bispecific antibody is suspended in a suitable dispersion medium; or an emulsion in which a solution prepared by dissolving an effective amount of the bispecific antibody is dispersed and emulsified in an appropriate dispersion medium.

For parenteral administration, the bispecific antibody of the present invention can be formulated into a dosage form such as a solution for injection, a suspension, an emulsion, a cream, an ointment, an inhalant, or a suppository, with a pharmaceutically acceptable solvent, an excipient, a binder, a stabilizer, or a dispersant, or the like. For the formulation for injection, the bispecific antibody of the present invention can be dissolved in an aqueous solution, preferably in a physiologically compatible buffer such as Hank's solution, Ringer's solution, or a physiological saline buffer. Furthermore, the pharmaceutical composition of the present invention can take a form of a suspension, a solution, or an emulsion in an oily or aqueous vehicle. Alternatively, the bispecific antibody of the present invention may be formulated in the form of a powder, and then prepared before use in an aqueous solution or suspension with sterile water or the like. For administration by inhalation, the bispecific antibody of the present invention can be pulverized and formulated into a powder mixture with a suitable base such as lactose or starch. A suppository formulation can be prepared by mixing the bispecific antibody of the present invention with a conventional suppository base such as cacao butter. Furthermore, the pharmaceutical composition of the present invention can be enclosed in a polymer matrix or the like to be formulated into a sustained release formulation.

Of these dosage forms, an injectable formulation is preferred. The injectable formulation is preferably administered parenterally such as intravenously, transdermally, intradermally, intraperitoneally, or intramuscularly.

The dose of the bispecific antibody as an active ingredient may be appropriately set in accordance with a symptom of a patient, a route of administration, a body weight or age, or the like, but, for example, it is preferably 0.001 to 1000 mg/kg, and more preferably 0.01 to 100 mg/kg per day for an adult.

The pharmaceutical composition of the present invention can comprise, in addition to the bispecific antibody of the present invention, a component useful for treatment of a B cell-related disease, preferably for treatment of a B cell tumor, such as a chemotherapeutic agent or another antibody drug.

EXAMPLES

Next, the present invention is explained in more detail by way of examples, but the technical scope of the present invention is not limited to these examples.

Example 1 Construction of Expression Vector (1) Construction of expression vector for humanized anti-IgM antibody (1)

The genes of heavy chain and light chain variable regions of the humanized anti-IgM antibody (1) were obtained with reference to a known mouse anti-IgM antibody (GenBank entry: L17037.1) by replacing the mouse framework region (FR) with a nucleotide sequence encoding corresponding human FR by a conventional method. In Table 2, the amino acid sequences of the used heavy chain complementarity determining regions (CDRs) are set forth in SEQ ID NOs: 1 to 3, and the amino acid sequences of the light chain CDRs are set forth in SEQ ID NOs: 4 to 6. The CDRs were in compliance with the Kabat definition.

TABLE 2

|                  | Amino acid sequence | SEQ ID NO: |
|------------------|---------------------|------------|
| Heavy chain CDR1 | TYWVN               | 1          |
| Heavy chain CDR2 | RIDPYDSETLYNQKFKD   | 2          |
| Heavy chain CDR3 | ETYDYPFAY           | 3          |
| Light chain CDR1 | KSSQSLLQSSNQKNYLA   | 4          |
| Light chain CDR2 | FASTRES             | 5          |
| Light chain CDR3 | QQHYSTPFT           | 6          |

To an upstream part of each of the obtained heavy chain and light chain variable region gene fragments, a known extracellular secretion signal sequence (Haisma, H. J., et al., Blood, 92 (1): 184-190, 1998) was ligated. Furthermore, to facilitate the cloning, a restriction enzyme KpnI recognition sequence was ligated to an upstream part of the secretion signal sequence of the heavy chain; and a restriction enzyme NheI recognition sequence was ligated to the 3' end of the variable region so as not to mutate amino acids of the junction of the variable region and the constant region. Similarly, a restriction enzyme Hind III recognition sequence was ligated to an upstream part of the secretion signal sequence of the light chain, and also a restriction enzyme BsiWI recognition sequence was ligated to the 3' end of the variable region. The designed genes of the heavy chain and light chain variable regions were synthesized by a PCR method, and the PCR product was cloned into a cloning vector such as p3T. After the cloning, the nucleotide sequences of the obtained clones were examined to select a clone having the same nucleotide sequence as the designed gene sequence.

Then, a humanized anti-IgM antibody (1) expression vector was constructed as follows. From each of the cloning vectors to which the heavy chain and light chain variable region gene fragments were inserted, a gene fragment was obtained with specific restriction enzymes. Each of the obtained gene fragment was sequentially ligated to an antibody expression vector carrying the human κ light chain constant region gene and the human IgG1 heavy chain constant region gene described in Example 1 of WO2014/069647. The ligated vector expresses a neomycin resistance gene or hygromycin resistance gene, and a humanized anti-human IgM antibody (1) gene in animal cells.

(2) Construction of Human Anti-HLA-DR Antibody (1) Expression Vector

The genes of the heavy chain and light chain variable regions of a human anti-HLA-DR antibody (1) were synthesized by a PCR method using PCR primers designed based on the antibody variable region nucleotide sequence described in Example 12 of JP-A-2005-325133. After cloning the obtained PCR product into a cloning vector such as p3T, a clone having the same sequence as the above-described gene sequence was selected. In Table 3, the amino acid sequences for the heavy chain CDRs of the antibody used are set forth in SEQ ID NOs: 7 to 9, and the amino acid sequences of the light chain CDRs are set forth in SEQ ID NOs: 10 to 12.

TABLE 3

|                  | Amino acid sequence  | SEQ ID NO: |
|------------------|----------------------|------------|
| Heavy chain CDR1 | SNSASWN              | 7          |
| Heavy chain CDR2 | RTYYRSKWYNDYAVSVKS   | 8          |
| Heavy chain CDR3 | ENFYGSETCHKKYYCYGMDV | 9          |
| Light chain CDR1 | RASQGISSALA          | 10         |
| Light chain CDR2 | DASSLES              | 11         |
| Light chain CDR3 | QQFNSFPLT            | 12         |

To an upstream part of each of the obtained heavy chain and light chain variable region gene fragments, the same extracellular secretion signal sequence as in Example 1 (1) was ligated. Furthermore, restriction enzyme recognition sequences were ligated to an upstream part of the secretion signal sequence and the 3' end of the variable region. In the same manner as in Example 1(1), after selecting a clone having the same nucleotide sequence as the gene sequence of interest, the heavy chain and light chain variable region gene fragments were cut out with specific restriction enzymes, and sequentially ligated to an antibody expression vector carrying the human κ light chain constant region gene and the human IgG1 heavy chain constant region gene described in Example 1 of WO2014/069647. The ligated vector expresses a neomycin resistance gene or puromycin resistance gene, and a human anti-HLA-DR antibody (1) gene in animal cells.

(3) Construction of Chimeric Anti-CD20 Antibody (1) Expression Vector

The genes of the heavy chain and light chain variable regions of a chimeric anti-CD20 antibody (1) were synthesized by a PCR method using PCR primers designed based on the antibody variable region nucleotide sequence described in Example II of JP-A-H08-503468. After cloning the PCR product into a cloning vector such as p3T, a clone having the same sequence as the above-described gene sequence was selected. In Table 4, the amino acid sequences of the heavy chain CDRs are set forth in SEQ ID NOs: 13 to 15, and the amino acid sequences of the light chain CDRs are set forth in SEQ ID NOs: 16 to 18.

TABLE 4

| | Amino acid sequence | SEQ ID NO: |
|---|---|---|
| Heavy chain CDR1 | SYNMH | 13 |
| Heavy chain CDR2 | AIYPGNGDTSYNQKFKG | 14 |
| Heavy chain CDR3 | STYYGGDWYFNV | 15 |
| Light chain CDR1 | RASSSVSYIH | 16 |
| Light chain CDR2 | ATSNLAS | 17 |
| Light chain CDR3 | QQWTSNPPT | 18 |

To the 5' and 3' ends of the heavy chain and light chain variable region gene fragments comprising a secretion signal sequence described in Example IIA of JP-A-H08-503468, restriction enzyme recognition sequences were ligated in accordance with Example 1(1). In the same manner as in Example 1(1), after selecting a clone having the same nucleotide sequence as the gene sequence of interest, the heavy chain and light chain variable region gene fragments were cut out with specific restriction enzymes, and sequentially ligated to an antibody expression vector carrying the human κ light chain constant region gene and the human IgG1 heavy chain constant region gene described in Example 1 of WO2014/069647. The ligated vector expresses a neomycin resistance gene and a chimeric anti-CD20 antibody (1) gene in animal cells.

(4) Construction of Chimeric Anti-CD20 Antibody (2) Expression Vector

According to a conventional method, a mouse anti-CD20 antibody-producing hybridoma was established by immunizing BALB/c mice with Ramos cells (CRL-1596, American Type Culture Collection: ATCC). The Ramos cells are a cell line derived from human Burkitt's lymphoma and express CD20, IgM, and CD37 on the cell surface. The Ramos cells were cultured under the condition of 37C, 5% $CO_2$ using Ramos cell growth medium. The Ramos cell growth medium was RPMI 1640 (Life Technologies) containing 10% fetal bovine serum (FBS, Life Technologies), 1% penicillin-streptomycin solution (penicillin final concentration: 100 units/mL, streptomycin final concentration: 0.1 mg/mL, Sigma-Aldrich). By synthesizing cDNA from the total RNA of the established hybridoma, variable region genes of the antibody were cloned. In Table 5, the amino acid sequences of the heavy chain CDRs of the obtained antibody are set forth in SEQ ID NOs: 19 to 21, and the amino acid sequences of the light chain CDRs are set forth in SEQ ID NOs: 22 to 24.

TABLE 5

| | Amino acid sequence | SEQ ID NO: |
|---|---|---|
| Heavy chain CDR1 | SYNMH | 19 |
| Heavy chain CDR2 | AIYPGNGDTSYNQKFKG | 20 |
| Heavy chain CDR3 | AYYGSSYEWYFDV | 21 |

TABLE 5-continued

| | Amino acid sequence | SEQ ID NO: |
|---|---|---|
| Light chain CDR1 | RASSSVRSMH | 22 |
| Light chain CDR2 | ATSNLAS | 23 |
| Light chain CDR3 | QQWSSNPPT | 24 |

To an upstream part of each of the obtained heavy chain and light chain variable region gene fragments, the same extracellular secretion signal sequence as in Example 1(1) was ligated. Furthermore, restriction enzyme recognition sequences were ligated to an upstream part of the secretion signal sequence and the 3' end of the variable region. In the same manner as in Example 1(1), after selecting a clone having the same nucleotide sequence as the gene sequence of interest, the heavy chain and light chain variable region gene fragments were cut out with specific restriction enzymes, and sequentially ligated to an antibody expression vector carrying the human κ light chain constant region gene and the human IgG1 heavy chain constant region gene described in Example 1 of WO2014/069647. The ligated vector expresses a neomycin resistance gene and a chimeric anti-CD20 antibody gene (2) in animal cells.

(5) Construction of Chimeric Anti-CD32b Antibody Expression Vector

The genes of the heavy chain and light chain variable regions of a chimeric anti-CD32b antibody were obtained with reference to the nucleotide sequence of the antibody variable region described in Example 1.0 of US2006/0073142 A1. In Table 6, the amino acid sequences of the heavy chain CDRs are set forth in SEQ ID NOs: 25 to 26, and the amino acid sequences of the light chain CDRs are set forth in SEQ ID NOs: 27 to 29. It should be noted that the amino acid sequence of the heavy chain CDR3 is FDY.

TABLE 6

| | Amino acid sequence | SEQ ID NO: |
|---|---|---|
| Heavy chain CDR1 | DAWMD | 25 |
| Heavy chain CDR2 | EIRSKPNNHATYYAESVKG | 26 |
| Heavy chain CDR3 | FDY | |
| Light chain CDR1 | RASQEISGYLS | 27 |
| Light chain CDR2 | AASALDS | 28 |
| Light chain CDR3 | LQYVSYPLT | 29 |

To an upstream part of each of the obtained heavy chain and light chain variable region gene fragments, the same extracellular secretion signal sequence as in Example 1(1) was ligated. Furthermore, restriction enzyme recognition sequences were ligated to an upstream part of the secretion signal sequence and the 3' end of the variable region. In the same manner as in Example 1(1), after selecting a clone having the same nucleotide sequence as the gene sequence of interest, the heavy chain and light chain variable region gene fragments were cut out with specific restriction enzymes, and sequentially ligated to an antibody expression vector carrying the human κ light chain constant region gene and the human IgG1 heavy chain constant region gene described in Example 1 of WO2014/069647. The ligated vector expresses a neomycin resistance gene and a chimeric anti-CD32b antibody gene in animal cells.

(6) Construction of Chimeric Anti-CD37 Antibody Expression Vector

According to a conventional method, a mouse anti-CD37 antibody-producing hybridoma was established by immunizing BALB/c mice with Ramos cells. By synthesizing cDNA from the total RNA of the established hybridoma, variable region genes of the antibody were cloned. In Table 7, the amino acid sequences of the heavy chain CDRs of the cloned antibody are set forth in SEQ ID NOs: 30 to 32, and the amino acid sequences of the light chain CDRs are set forth in SEQ ID NOs: 33 to 35.

TABLE 7

|  | Amino acid sequence | SEQ ID NO: |
| --- | --- | --- |
| Heavy chain CDR1 | RYSVH | 30 |
| Heavy chain CDR2 | MIWGGGITDYNSALKS | 31 |
| Heavy chain CDR3 | PWGSSGPFAY | 32 |
| Light chain CDR1 | RASGNIHNYLA | 33 |
| Light chain CDR2 | NAKTLAD | 34 |
| Light chain CDR3 | QHFWTTPLT | 35 |

To an upstream part of each of the obtained heavy chain and light chain variable region gene fragments, the same extracellular secretion signal sequence as in Example 1(1) was ligated. Furthermore, restriction enzyme recognition sequences were ligated to an upstream part of the secretion signal sequence and the 3' end of the variable region. In the same manner as in Example 1(1), after selecting a clone having the same nucleotide sequence as the gene sequence of interest, the heavy chain and light chain variable region gene fragments were cut out with specific restriction enzymes, and sequentially ligated to an antibody expression vector carrying the human κ light chain constant region gene and the human IgG1 heavy chain constant region gene described in Example 1 of WO2014/069647. The ligated vector expresses a neomycin resistance gene and a chimeric anti-CD37 antibody gene in animal cells.

(7) Construction of Humanized Anti-CD52 Antibody Expression Vector

The genes of the heavy chain and light chain variable regions of a humanized anti-CD52 antibody were obtained with reference to the nucleotide sequence of the antibody variable region described in Example 1 of JP-A-H02-503514. In Table 8, the amino acid sequences of the heavy chain CDRs are set forth in SEQ ID NOs: 36 to 38, and the amino acid sequences of the light chain CDRs are set forth in SEQ ID NOs: 39 to 41.

TABLE 8

|  | Amino acid sequence | SEQ ID NO: |
| --- | --- | --- |
| Heavy chain CDR1 | DFYMN | 36 |
| Heavy chain CDR2 | FIRDKAKGYTTEYNPSVKG | 37 |

TABLE 8-continued

|  | Amino acid sequence | SEQ ID NO: |
| --- | --- | --- |
| Heavy chain CDR3 | EGHTAAPFDY | 38 |
| Light chain CDR1 | KASQNIDKYLN | 39 |
| Light chain CDR2 | NTNNLQT | 40 |
| Light chain CDR3 | LQHISRPRT | 41 |

To an upstream part of each of the obtained heavy chain and light chain variable region gene fragments, the same extracellular secretion signal sequence as in Example 1(1) was ligated. Furthermore, restriction enzyme recognition sequences were ligated to an upstream part of the secretion signal sequence and the 3' end of the variable region. In the same manner as in Example 1(1), after selecting a clone having the same nucleotide sequence as the gene sequence of interest, the heavy chain and light chain variable region gene fragments were cut out with specific restriction enzymes, and sequentially ligated to an antibody expression vector carrying the human κ light chain constant region gene and the human IgG1 heavy chain constant region gene described in Example 1 of WO2014/069647. The ligated vector expresses a neomycin resistance gene and a humanized anti-CD52 antibody gene in animal cells.

(8) Construction of Humanized Anti-BAFF Receptor Antibody Expression Vector

The heavy chain and light chain variable region genes of a humanized anti-BAFF receptor antibody are obtained. To an upstream part of each of the obtained heavy chain and light chain variable region gene fragments, the same extracellular secretion signal sequence as in Example 1(1) is ligated. Furthermore, restriction enzyme recognition sequences are ligated to an upstream part of the secretion signal sequence and the 3' end of the variable region. In the same manner as in Example 1(1), after selecting a clone having the same nucleotide sequence as the gene sequence of interest, the heavy chain and light chain variable region gene fragments are cut out with specific restriction enzymes, and sequentially ligated to an antibody expression vector carrying the human κ light chain constant region gene and the human IgG1 heavy chain constant region gene described in Example 1 of WO2014/069647. The ligated vector expresses a neomycin resistance gene and a humanized anti-BAFF receptor antibody gene in animal cells.

(9) Construction of Chimeric Anti-BCMA Antibody Expression Vector

The genes of the heavy chain and light chain variable regions of a chimeric anti-BCMA antibody were obtained with reference to the amino acid sequence of the variable region of C12A3.2 described in JP-B-6061469. In Table 9, the amino acid sequences of the heavy chain CDRs are set forth in SEQ ID NOs: 42 to 44 and the amino acid sequences of the light chain CDRs are set forth in SEQ ID NOs: 45 to 47.

TABLE 9

|  | Amino acid sequence | SEQ ID NO: |
| --- | --- | --- |
| Heavy chain CDR1 | HYSMN | 42 |
| Heavy chain CDR2 | RINTESGVPIYADDFKG | 43 |

TABLE 9-continued

|  | Amino acid sequence | SEQ ID NO: |
|---|---|---|
| Heavy chain CDR3 | DYLYSLDF | 44 |
| Light chain CDR1 | RASESVTILGSHLIY | 45 |
| Light chain CDR2 | LASNVQT | 46 |
| Light chain CDR3 | LQSRTIPRT | 47 |

To an upstream part of each of the obtained heavy chain and light chain variable region gene fragments, the same extracellular secretion signal sequence as in Example 1(1) is ligated. Furthermore, restriction enzyme recognition sequences are ligated to an upstream part of the secretion signal sequence and the 3' end of the variable region. In the same manner as in Example 1(1), after selecting a clone having the same nucleotide sequence as the gene sequence of interest, the heavy chain and light chain variable region gene fragments were cut out with specific restriction enzymes, and sequentially ligated to an antibody expression vector carrying the human κ light chain constant region gene and the human IgG1 heavy chain constant region gene described in Example 1 of WO2014/069647. The ligated vector expresses a neomycin resistance gene and a chimeric anti-BCMA antibody gene in animal cells.

(10) Construction of Chimeric Anti-TACI Antibody Expression Vector

The genes of the heavy chain and light chain variable regions of chimeric anti-TACI antibody are obtained. To an upstream part of each of the obtained heavy chain and light chain variable region gene fragments, the same extracellular secretion signal sequence as in Example 1(1) is ligated. Furthermore, restriction enzyme recognition sequences are ligated to an upstream part of the secretion signal sequence and the 3' end of the variable region. In the same manner as in Example 1(1), after selecting a clone having the same nucleotide sequence as the gene sequence of interest, the heavy chain and light chain variable region gene fragments are cut out with specific restriction enzymes, and sequentially ligated to an antibody expression vector carrying the human κ light chain constant region gene and the human IgG1 heavy chain constant region gene described in Example 1 of WO2014/069647. The ligated vector expresses a neomycin resistance gene and a chimeric anti-TACI antibody gene in animal cells.

(11) Construction of Chimeric Anti-IgM Antibody Expression Vector

According to a conventional method, a mouse anti-IgM antibody-producing hybridoma was established by immunizing BALB/c mice with WKAH/Hkm rat B cells. By synthesizing cDNA from the total RNA of the established hybridoma, variable region genes of the antibody were cloned. In Table 10, the amino acid sequences of the heavy chain CDRs of the obtained antibody are set forth in SEQ ID NOs: 48 to 50, and the amino acid sequences of the light chain CDRs are set forth in SEQ ID NOs: 51 to 53.

TABLE 10

|  | Amino acid sequence | SEQ ID NO: |
|---|---|---|
| Heavy chain CDR1 | NYGMN | 48 |
| Heavy chain CDR2 | WINTYSGEPTYADDFKG | 49 |

TABLE 10-continued

|  | Amino acid sequence | SEQ ID NO: |
|---|---|---|
| Heavy chain CDR3 | ETTIFDY | 50 |
| Light chain CDR1 | RTSDNIYSYLA | 51 |
| Light chain CDR2 | NTQTLAK | 52 |
| Light chain CDR3 | QHHYNTPYT | 53 |

To the 5' and 3' ends of the heavy chain and light chain variable region gene fragments comprising a secretion signal sequence derived from a mouse anti-IgM antibody, restriction enzyme recognition sequences were ligated according to Example 1(1). After selecting a clone having the same nucleotide sequence as the gene sequence of interest, the heavy chain and light chain variable region gene fragments were cut out with specific restriction enzymes, and sequentially ligated to an antibody expression vector carrying the human κ light chain constant region gene and the human IgG1 heavy chain constant region gene described in Example 1 of WO2014/069647. The ligated vector expresses a neomycin resistance gene and a chimeric anti-IgM antibody gene in animal cells.

(12) Construction of Humanized Anti-EGFR Antibody (Negative Control) Expression Vector The genes of the heavy chain and light chain variable regions of a humanized anti-EGFR antibody (negative control) were obtained with reference to the nucleotide sequence of the antibody variable region described in Example 4 of U.S. Pat. No. 5,558,864. In Table 11, the amino acid sequences of the heavy chain CDRs are set forth in SEQ ID NOs: 54 to 56, and the amino acid sequences of the light chain CDRs are set forth in SEQ ID NOs: 57 to 59.

TABLE 11

|  | Amino acid sequence | SEQ ID NO: |
|---|---|---|
| Heavy chain CDR1 | SHWMH | 54 |
| Heavy chain CDR2 | EFNPSNGRTNYNEKFKS | 55 |
| Heavy chain CDR3 | RDYDYDGRYFDY | 56 |
| Light chain CDR1 | SASSSVTYMY | 57 |
| Light chain CDR2 | DTSNLAS | 58 |
| Light chain CDR3 | QQWSSHIFT | 59 |

To an upstream part of each of the obtained heavy chain and light chain variable region gene fragments, the same extracellular secretion signal sequence as in Example 1(1) was ligated. Furthermore, restriction enzyme recognition sequences were ligated to an upstream part of the secretion signal sequence and the 3' end of the variable region. In the same manner as in Example 1(1), after selecting a clone having the same nucleotide sequence as the gene sequence of interest, the heavy chain and light chain variable region gene fragments were cut out with specific restriction enzymes, and sequentially ligated to an antibody expression vector carrying the human κ light chain constant region gene and the human IgG1 heavy chain constant region gene described in Example 1 of WO2014/069647. The ligated vector expresses a neomycin resistance gene and a humanized anti-EGFR antibody gene in animal cells.

(13) Construction of Chimeric Anti-IgM Antibody Expression Vectors

According to a conventional method, four mouse anti-IgM antibody-producing hybridomas were established by immunizing BALB/c mice with human IgM and monkey IgM. By synthesizing cDNA from the total RNA of the established hybridoma, variable region genes of the antibody were cloned. In Table 12, the amino acid sequences of the heavy chain CDRs of the cloned anti-IgM antibody (2) are set forth in SEQ ID NOs: 60 to 62, and the amino acid sequences of the light chain CDRs are set forth in SEQ ID NOs: 63 to 65. In Table 13, the amino acid sequences of the heavy chain CDRs of the cloned anti-IgM antibody (3) are set forth in SEQ ID NOs: 66 to 68, and the amino acid sequences of the light chain CDRs are set forth in SEQ ID NOs: 69 to 71. In Table 14, the amino acid sequences of the heavy chain CDRs of the cloned anti-IgM antibody (4) are set forth in SEQ ID NOs: 72 to 74, and the amino acid sequences of the light chain CDRs are set forth in SEQ ID NOs: 75 to 77. In Table 15, the amino acid sequences of the heavy chain CDRs of the cloned anti-IgM antibody (5) are set forth in SEQ ID NOs: 78 to 80, and the amino acid sequences of the light chain CDRs are set forth in SEQ ID NOs: 81 to 83.

TABLE 12

|  | Amino acid sequence | SEQ ID NO: |
|---|---|---|
| Heavy chain CDR1 | SFGMH | 60 |
| Heavy chain CDR2 | YISSGSNTIYYADTVKG | 61 |
| Heavy chain CDR3 | WTGRAMDY | 62 |
| Light chain CDR1 | KASQDVGTAVG | 63 |
| Light chain CDR2 | WASTRHT | 64 |
| Light chain CDR3 | QQYSSYLYT | 65 |

TABLE 13

|  | Amino acid sequence | SEQ ID NO: |
|---|---|---|
| Heavy chain CDR1 | SYWIE | 66 |
| Heavy chain CDR2 | EILPGSGSTNYNEKFKG | 67 |
| Heavy chain CDR3 | QIGYYGLYYGMDY | 68 |
| Light chain CDR1 | SASSSINYMH | 69 |
| Light chain CDR2 | GTSNLAS | 70 |
| Light chain CDR3 | QQRSSYPLT | 71 |

TABLE 14

|  | Amino acid sequence | SEQ ID NO: |
|---|---|---|
| Heavy chain CDR1 | SFGMH | 72 |
| Heavy chain CDR2 | YISSGSNTIYYADTVKG | 73 |
| Heavy chain CDR3 | WTGRAMDY | 74 |
| Light chain CDR1 | KASQDVGTAVA | 75 |
| Light chain CDR2 | WASTRHI | 76 |
| Light chain CDR3 | HQYSSYLYT | 77 |

TABLE 15

|  | Amino acid sequence | SEQ ID NO: |
|---|---|---|
| Heavy chain CDR1 | SYVMH | 78 |
| Heavy chain CDR2 | YINPYNDDTKYNENFKG | 79 |
| Heavy chain CDR3 | VWSYYSAMDY | 80 |
| Light chain CDR1 | RSSQSVLYSSNQKNYLA | 81 |
| Light chain CDR2 | WASIRES | 82 |
| Light chain CDR3 | HQYLSSWT | 83 |

To the obtained secretion signal sequence, an upstream part of each of the heavy chain and light chain variable region gene fragments and the 3' end of the variable region, restriction enzyme recognition sequences were ligated. In the same manner as in Example 1(1), after selecting a clone having the same nucleotide sequence as the gene sequence of interest, the heavy chain and light chain variable region gene fragments were cut out with specific restriction enzymes, and sequentially ligated to an antibody expression vector carrying the human κ light chain constant region gene and the human IgG1 heavy chain constant region gene described in Example 1 of WO2014/069647. The ligated vector expresses a neomycin resistance gene, and a chimeric anti-human IgM antibody (2) gene, or a chimeric anti-human IgM antibody (3) gene, or a chimeric anti-human IgM antibody (4) gene or a chimeric anti-human IgM antibody (5) in animal cells.

(14) Construction of Chimeric Anti-HLA-DR Antibody (2) Expression Vector

The genes of the heavy chain and light chain variable regions of a chimeric anti-HLA-DR antibody (2) were synthesized by a PCR method using PCR primers designed based on the antibody variable region nucleotide sequence described in FIGS. 1 and 2 of U.S. Pat. No. 7,612,180. After cloning the PCR product into a cloning vector such as p3T, a clone having a sequence identical to the described gene sequence was selected. In Table 16, the amino acid sequences of the heavy chain CDRs of the antibody used are set forth in SEQ ID NOs: 84 to 86, and the amino acid sequences of the light chain CDRs are set forth in SEQ ID NOs: 87 to 89.

TABLE 16

|  | Amino acid sequence | SEQ ID NO: |
| --- | --- | --- |
| Heavy chain CDR1 | NYGMN | 84 |
| Heavy chain CDR2 | WINTYTREPTYADDFKG | 85 |
| Heavy chain CDR3 | DITAVVPTGFDY | 86 |
| Light chain CDR1 | RASENIYSNLA | 87 |
| Light chain CDR2 | AASNLAD | 88 |
| Light chain CDR3 | QHFWTTPWA | 89 |

To an upstream part of each of the obtained heavy chain and light chain variable region gene fragments, the same extracellular secretion signal sequence as in Example 1(1) was ligated. Furthermore, restriction enzyme recognition sequences were ligated to an upstream part of the secretion signal sequence and the 3' end of the variable region. In the same manner as in Example 1(1), after selecting a clone having the same nucleotide sequence as the gene sequence of interest, the heavy chain and light chain variable region gene fragments were cut out with specific restriction enzymes, and sequentially ligated to an antibody expression vector carrying the human κ light chain constant region gene and the human IgG1 heavy chain constant region gene described in Example 1 of WO2014/069647. The ligated vector expresses a neomycin resistance gene or puromycin resistance gene, and a chimeric anti-HLA-DR antibody (2) gene in animal cells.

(15) Construction of Humanized Anti-CD38 Antibody Expression Vector

The genes of the heavy chain and light chain variable regions of a humanized anti-CD38 antibody were obtained with reference to the nucleotide sequence of the antibody variable region described in WO2012/092612. In Table 17, the amino acid sequences of the heavy chain CDRs are set forth in SEQ ID NOs: 90 to 92, and the amino acid sequences of the light chain CDRs are set forth in SEQ ID NOs: 93 to 95.

TABLE 17

|  | Amino acid sequence | SEQ ID NO: |
| --- | --- | --- |
| Heavy chain CDR1 | DYGMS | 90 |
| Heavy chain CDR2 | DISWNGGKTHYVDSVKG | 91 |
| Heavy chain CDR3 | GSLFHDSSGFYFGH | 92 |
| Light chain CDR1 | SGSSSNIGDNYVS | 93 |
| Light chain CDR2 | RDSQRPS | 94 |
| Light chain CDR3 | QSYDSSLSGSV | 95 |

To an upstream part of each of the obtained heavy chain and light chain variable region gene fragments, the same extracellular secretion signal sequence as in Example 1(1) was ligated. Furthermore, restriction enzyme recognition sequences were ligated to an upstream part of the secretion signal sequence and the 3' end of the variable region. In the same manner as in Example 1(1), after selecting a clone having the same nucleotide sequence as the gene sequence of interest, the heavy chain and light chain variable region gene fragments were cut out with specific restriction enzymes, and sequentially ligated to an antibody expression vector carrying the human γ light chain constant region gene and the human IgG1 heavy chain constant region gene described in Example 1 of WO2014/069647. The ligated vector expresses a neomycin resistance gene and a humanized anti-CD38 antibody gene in animal cells.

(16) Construction of Humanized Anti-CD81 Antibody Expression Vector

The genes of the heavy chain and light chain variable regions of a humanized anti-CD81 antibody were obtained with reference to the nucleotide sequence of the antibody variable region described in WO2012/077649. In Table 18, the amino acid sequences of the heavy chain CDRs are set forth in SEQ ID NOs: 96 to 98, and the amino acid sequences of the light chain CDRs are set forth in SEQ ID NOs: 99 to 101.

TABLE 18

|  | Amino acid sequence | SEQ ID NO: |
| --- | --- | --- |
| Heavy chain CDR1 | SNYMS | 96 |
| Heavy chain CDR2 | YISSSSTYTDYADSVKGRF | 97 |
| Heavy chain CDR3 | YSYGRDNFDY | 98 |
| Light chain CDR1 | TGSTSNIGAGYDTH | 99 |
| Light chain CDR2 | GNSNRPS | 100 |
| Light chain CDR3 | QSYDTNLSVWV | 101 |

To an upstream part of each of the obtained heavy chain and light chain variable region gene fragments, the same extracellular secretion signal sequence as in Example 1(1) was ligated. Furthermore, restriction enzyme recognition sequences were ligated to an upstream part of the secretion signal sequence and the 3' end of the variable region. In the same manner as in Example 1(1), after selecting a clone having the same nucleotide sequence as the gene sequence of interest, the heavy chain and light chain variable region gene fragments were cut out with specific restriction enzymes, and sequentially ligated to an antibody expression vector carrying the human λ light chain constant region gene and the human IgG1 heavy chain constant region gene described in Example 1 of WO2014/069647. The ligated vector expresses a neomycin resistance gene and a humanized anti-CD81 antibody gene in animal cells.

Example 2 Production of Antibody (1) Production of Monoclonal Antibody

The antibody expression vector prepared in Example 1 above were transfected into FreeStyle 293-F cells (Life Technologies) with 293fectin (Life Technologies), or into ExpiCHO cells (Life Ttechnologies) with ExpiFectamine (Life Technologies). In accordance with the instruction by the manufacturer, the resultant was cultured under the condition of 32 to 37° C., 5 to 8% $CO_2$ for 1 to 2 weeks, and then the culture supernatant was obtained. From the culture supernatant, monoclonal antibodies were purified using HiTrap Protein A column (GE Healthcare). The purified monoclonal antibodies were dialyzed against phosphate buffered saline (PBS, pH 7.0), and stored at 4° C. until use in the test.

(2) Production of Bispecific Antibody
(2-1) Production of Cys1m Type Bispecific Antibody The antibody expression vector prepared in Example 1 above was altered in accordance with WO2014/069647. Specifically, for purifying bispecific antibodies efficiently using the differences in protein A binding ability as index, the histidine at position 435 of the heavy chain of anti-IgM antibody (1) was substituted by an arginine (H435R) and the tyrosine at position 436 of the heavy chain of the antibody was substituted by a phenylalanine (Y436F), to thereby change the antibody from a human IgG1 type to human IgG3 type. Further, when the combination partner of the anti-IgM antibody (1) in preparing the bispecific antibodies is a chimeric anti-CD20 antibody (1), in order to disable a native disulfide bond between the light chain and heavy chain of anti-IgM antibody (1), the cysteine at position 214 of the light chain was substituted by a serine (C214S) and the cysteine at position 220 of the heavy chain was substituted by a serine (C220S), respectively, and in order to introduce a non-natural disulfide bond, the serine at position 162 of the light chain was substituted by a cysteine (S162C) and the phenylalanine at position 170 of the heavy chain was substituted by a cysteine (F170C), respectively. When the combination partner is other than chimeric anti-CD20 antibody (1), the same mutations as described above were added to the partner antibody. With these mutations, the antibody having a desired combination between light chain and heavy chain can be efficiently produced. The obtained altered anti-IgM antibody (1) expression vector and altered anti-B cell surface antigen antibody expression vector were transfected into FreeStyle 293-F cells or ExpiCHO cells. In accordance with the instruction by the manufacturer, the resultant was cultured under the condition of 32 to 37° C., 5% to 8% $CO_2$ for 1 to 2 weeks, and then the culture supernatant was obtained. After purification of the culture supernatant using a HiTrap Protein A column (GE Healthcare) or ProSep-vA High Capacity column (Merck Millipore), the bispecific antibodies were fractionated by a CEX chromatography. For fractionation, a strong cation exchange column PL-SCX (Agilent Technologies, Inc., particle size: 8 μm, pore size: 1000 Å) was used. As the mobile phase, mobile phase solution A (10 mM MES, pH 6.0) and mobile phase solution B (500 mM NaCl, 10 mM MES, pH 6.0) were used. The initial mobile phase (98% solution A, 2% solution B) was fed in five times or more the capacity of the column at a flow rate of 1 mL/min to equilibrate the column in advance, and the purified sample was injected to the equilibrated column (0 min) and allowed to bind to the column by electrical charge. After washing for 5 minutes with the initial mobile phase, the mixing ratio of solution B was gradually increased for 47.5 minutes with a linear gradient of 0.8% increase per minute so that the final mixing ratio of the solution B was 40%. Immediately thereafter, the mixing ratio of solution B was raised to 100%, and the column was washed. During this time, the absorbance at 280 nm was recorded, and a peak corresponding to a retention time of the bispecific antibody was fractionated. The obtained bispecific antibodies were dialyzed against PBS (pH 7.0), and stored at 4° C. until use in the test.

(2-2) Production of Knobs-into-Holes (KIH) Type Bispecific Antibody

As another embodiment of the bispecific antibody, the antibody expression vector prepared in Example 1 was altered in accordance with U.S. Pat. No. 5,731,168A and Marchant, A. M., et al., Nat. Biotechnol., 16 (7): 677-681, 1998. Specifically, the threonine at position 366 of the heavy chain of anti-IgM antibody (1) was substituted by a tryptophan (T366W), the tryptophan at position 366 of the heavy chain of an anti-B cell surface antigen antibody which is the combination partner of the anti-IgM antibody (1) was substituted by a serine (T366S), the leucine at position 368 of the heavy chain of the anti-B cell surface antigen antibody was substituted by an alanine (L368A), and the tyrosine at position 407 of the heavy chain of the anti-B cell surface antigen antibody was substituted by a valine (Y407V), respectively. With these mutations, the antibody having a desired combination between heavy chains can be efficiently produced. Furthermore, in order to purify the bispecific antibodies efficiently by employing the differences in protein A binding ability as index, the histidine at position 435 of the heavy chain of the anti-B cell surface antigen antibody was substituted by an arginine (H435R) and the tyrosine at position 436 of the heavy chain of the anti-B cell surface antigen antibody was substituted by a phenylalanine (Y436F), to thereby change the antibody from human IgG1 type to human IgG3 type. The obtained altered anti-IgM antibody (1) expression vector and altered anti-B cell surface antigen antibody expression vector were transfected into FreeStyle 293-F cells or ExpiCHO cells. In accordance with the instruction by the manufacturer, the resultant was cultured under the condition of 32 to 37° C., 5% to 8% $CO_2$ for 1 to 2 weeks, and then the culture supernatant was obtained. The culture supernatant of the cells to which the altered anti-IgM antibody (1) expression vector was introduced was purified using HiTrap Protein A column (GE Healthcare), and dialyzed against PBS (pH 7.0). The culture supernatant of the cells to which the altered anti-B cell surface antigen antibody expression vector was introduced was purified using HiTrap Protein G column (GE Healthcare), and dialyzed against PBS (pH 7.0). The obtained anti-IgM antibody (1) and the anti-B cell surface antigen antibody was mixed in 1:1, and to the mixture, 20 mM reduced glutathione (FUJIFILM Wako Pure Chemical Corporation) and 2 mM oxidized glutathione (FUJIFILM Wako Pure Chemical Corporation) at the final concentrations were added and reacted at 25° C. for 13 to 15 hours. After the reaction, antibodies were purified by HiTrap Protein A column, and further the bispecific antibody was fractionated by a size exclusion chromatography (TOSOH CORPORATION, TSKgel G3000SWXL). For mobile phase, 0.2 M $K_2HPO_4$ and 0.25 M KCl (pH 7.0) were used. The obtained bispecific antibodies were dialyzed against PBS (pH 7.0), and stored at 4° C. until use in the test.

(2-3) Production of Cys1m Type and KIH Type Bispecific Antibody

The antibody expression vector prepared in Example 1 above was altered in accordance with WO2014/069647. Specifically, for purifying bispecific antibodies efficiently using the differences in protein A binding ability as index, the histidine at position 435 of the heavy chain of the anti-B cell surface antigen antibody to be combined with the anti-IgM antibodies (2) to (5) was substituted by an arginine (H435R) and the tyrosine at position 436 of the heavy chain of the anti-B cell surface antigen antibody was substituted by a phenylalanine (Y436F), to thereby change the antibody from a human IgG1 type to human IgG3 type. In the anti-B cell surface antigen antibody which is a combination partner of the anti-IgM antibodies (2) to (5) in preparing the bispecific antibodies, in order to disable a native disulfide bond between the light chain and heavy chain, the cysteine at position 214 of the light chain was substituted by a serine (C214S) and the cysteine at position 220 of the heavy chain was substituted by a serine (C220S), respectively, and in order to introduce a non-natural disulfide bond, the serine at position 162 of the light chain was substituted by a cysteine (S162C) and the phenylalanine at position 170 of the heavy chain was substituted by a cysteine (F170C), respectively (Cys1m type). Furthermore, the antibody expression vector prepared in Example 1 above was altered in accordance with U.S. Pat. No. 5,731,168A and Marchant, A. M., et al., Nat. Biotechnol., 16(7): 677-681, 1998. Specifically, the threonine at position 366 of the heavy chain of anti-IgM antibodies (2) to (5) was substituted by a tryptophan (T366W), the tryptophan at position 366 of the heavy chain of anti-B cell surface antigen antibody which is the combination partner of the anti-IgM antibodies (2) to (5) was substituted by a serine (T366S), the leucine at position 368 of the heavy chain of the anti-B cell surface antigen antibody was substituted by an alanine (L368A), and the tyrosine at position 407 of the heavy chain of the anti-B cell surface antigen antibody was substituted by a valine (Y407V), respectively (KIH type). With these mutations, the antibody having a desired combination between light chain and heavy chain can be efficiently produced. The obtained altered anti-IgM antibodies (2) to (5) expression vectors and altered anti-B cell surface antigen antibody expression vector were transfected into FreeStyle 293-F cells or ExpiCHO cells. In accordance with the instruction by the manufacturer, the resultant was cultured under the condition of 32 to 37° C., 5% to 8% $CO_2$ for 1 to 2 weeks, and then the culture supernatant was obtained. After purification of the culture supernatant using a HiTrap Protein A column (GE Healthcare), the bispecific antibodies were fractionated by a CEX chromatography. For fractionation, a strong cation exchange column PL-SCX (Agilent Technologies, Inc., particle size: 8 µm, pore size: 1000 Å) was used. As the mobile phase, mobile phase solution A (10 mM MES, pH 6.0) and mobile phase solution B (500 mM NaCl, 10 mM MES, pH 6.0) were used. The initial mobile phase (98% solution A, 2% solution B) was fed in five times or more the capacity of the column at a flow rate of 1 mL/min to equilibrate the column in advance, and the purified sample was injected to the equilibrated column (0 min) and allowed to bind to the column by electrical charge. After washing for 5 minutes with the initial mobile phase, the mixing ratio of solution B was gradually increased for 47.5 minutes with a linear gradient of 0.8% increase per minute so that the final mixing ratio of the solution B was 40%. Immediately thereafter, the mixing ratio of solution B was raised to 100%, and the column was washed. During this time, the absorbance at 280 nm was recorded, and a peak corresponding to a retention time of the bispecific antibody was fractionated. The obtained bispecific antibodies were dialyzed against PBS (pH 7.0), and stored at 4° C. until use in the test.

Example 3 Analysis of Antigen-Binding Capacity of Bispecific Antibody (1) Measurement of the Numbers of IgM Molecules and HLA-DR Molecules on HH Cell Membrane Surface HH cells were used to confirm that the produced anti-IgM (1)/HLA-DR (1) bispecific antibody has binding ability to HLA-DR and IgM. First, the numbers of molecules of HLA-DR and IgM present on the HH cell membrane surface were examined. It is considered that the HH cells (CRL-2105, ATCC) do not express IgM since the HH cells are a cell line derived from human T cell lymphoma, whereas it is known that the HH cells express HLA-DR on the cell membrane surface. The HH cells were cultured under the condition of 37° C., 5l $CO_2$ using RPMI 1640 containing 10% FBS and 1% penicillin-streptomycin solution.

The numbers of molecules of HLA-DR and IgM were measured using a QIF kit (Dako). Specifically, 50 µL of mouse anti-HLA-DR antibody or mouse anti-IgM antibody (20 µg/mL) was added to a 96-well plate seeded with HH cells (2×10s cells/well) in advance, and allowed to react on ice for 1 hour. Then, the resultant was washed twice with 200 µL of PBS containing 5% FBS (5% FBS/PBS). Next, FITC-labeled anti-mouse IgG antibody in the kit was diluted 50-fold with 5% FBS/PBS, and the diluted antibody was added by 100 µL to each well. After reaction on ice for 45 minutes, the resultant was washed twice with 200 µL of 5% FBS/PBS, and HH cells were fixed with 1% formaldehyde (KANTO CHEMICAL CO., INC) diluted in PBS. Fluorescence derived from the fixed HH cells were measured by a flow cytometer (FC500MPL, Beckman Coulter, Inc.) and an analysis software Cytomics MXP cytometer (Beckman Coulter, Inc.). During the time, in accordance with the attached instructions, a calibration curve was prepared using the setup beads and calibration beads included in the kit, and the numbers of molecules of HLA-DR and IgM on the HH cell membrane surface were calculated. The results are shown in FIG. 1. The vertical axis in the figure shows the number of molecules per cell.

As the results of the test, the number of molecules of IgM on the cell membrane surface was calculated as $-0.1 \times 10^5$ molecules/cell, and the number of molecules of HLA-DR was calculated as $4.4 \times 10^5$ molecules/cell. From the results of this test using the HH cells derived from human T cells, it was confirmed that HH cells express HLA-DR on the cell membrane and do not express IgM.

(2) Binding of Anti-IgM/HLA-DR Bispecific Antibody to IgM and HLA-DR

Simultaneous binding of the anti-IgM (1)/HLA-DR (1) bispecific antibody to IgM and HLA-DR was confirmed using soluble IgM and HH cells. As shown in experiments of Example 3(1), HH cells express HLA-DR on the cell membrane surface, but do not express IgM.

Therefore, when the fluorescently labeled soluble IgM and a bispecific antibody are reacted with HH cells, the HH cells would be fluorescently labeled if the bispecific antibody is a heterodimer. Using this test system, it was examined whether or not the produced bispecific antibody binds simultaneously to IgM and HLA-DR.

With LYNX RAPID RPE ANTIBODY CONJUGATION KIT (Bio-Rad Laboratories, Inc), soluble IgM (AbD Serotec) was PE-labeled in accordance with the attached instructions. The anti-IgM (1)/HLA-DR (1) bispecific antibody, anti-HLA-DR antibody (1) or anti-IgM antibody (1) was diluted at common ratio 3 from 20 µg/mL, and then each antibody was mixed with 2 µg/mL of the PE-labeled soluble IgM at a volume ratio of 1:1, and allowed to stand for 30 minutes at room temperature. After the reaction, the mixed solution was added to a 96-well plate seeded with HH cells ($2 \times 10^5$ cells/well) in advance, and allowed to react on ice for 1 hour. Subsequently, each well was washed three times with 200 µL of 5% FBS/PBS, then cells were fixed with a 1% formaldehyde solution diluted with PBS. Fluorescence from the PE labels attached to fixed cells was measured by a flow cytometer, and analyzed by Cytomics MXP cytometer. The results are shown in FIG. 2. The vertical axis in the figure shows the mean fluorescence intensity (MFI), and the horizontal axis shows the antibody concentration.

The anti-HLA-DR antibody (1) binds to HH cells but not to soluble IgM, so the fluorescence was not detected. Furthermore, the anti-IgM antibody (1) binds to soluble IgM but not to HH cells, so the HH cells were not labeled with PE and the fluorescence was not detected. If the prepared anti-IgM (1)/HLA-DR (1) bispecific antibody forms a hetero body of interest, the bispecific antibody binds to both the PE-labeled soluble IgM and HH cells, thus the resultant PE-labeled HH cells would be detected. To confirm this, the anti-IgM (1)/HLA-DR (1) bispecific antibody was sequentially reacted with the PE-labeled soluble IgM and HH cells. As a result, the PE-labeled HH cells were detected. Moreover, the binding curves of Cys1m type bispecific antibody and KIH type bispecific antibody were similar. Thus it has been shown that there is no difference in binding due to the difference in the production method. In addition, although the data is not shown, no fluorescence was detected in any of the cases in which HH cells was used alone, HH cells were treated only with soluble IgM, or HH cells were treated only with the anti-IgM (1)/HLA-DR (1) bispecific antibody.

From these results, it has been shown that both Cys1m type and KIH type anti-IgM (1)/HLA-DR (1) bispecific antibodies prepared are a heterodimer of interest, and each of them has a property of simultaneously binding to IgM and HLA-DR.

Example 4 Cell Growth Inhibition Activity of Bispecific Antibody (1) Bispecific Antibody Combining Anti-IgM Antibody and Anti-HLA-DR Antibody
(1-1) Growth Inhibition Activity Against JeKo-1 Cells 1

The changes due to increase of the soluble IgM concentration in growth inhibition activities of the anti-IgM antibody (1), the anti-HLA-DR antibody (1), the anti-IgM (1)/HLA-DR (1) bispecific antibody and the anti-EGFR antibody as a negative control against JeKo-1 cells were investigated. The JeKo-1 cells (RL-3006, ATCC) are a cell line derived from human mantle cell lymphoma, which expresses IgM, the HLA-DR and CD20 on the cell surface. The JeKo-1 cells were cultured under the condition of 37° C., 5% $CO_2$ using JeKo-1 cell growth medium. The JeKo-1 cell growth medium was RPMI 1640 containing 20% FBS and 1% penicillin-streptomycin solution. To investigate the growth inhibition activity, soluble IgM which was diluted in the JeKo-1 cell growth medium at common ratio 3 from 40 µg/mL and each antibody (1200 ng/mL) were mixed at a volume ratio of 1:1, and allowed to stand for 30 minutes at room temperature. To a 96-well plate to which the JeKo-1 cells suspended in medium were seeded ($2 \times 10^4$ cells/well) in advance, the above-described mixed solution was added at the volume ratio of 1:1, and the resultant was cultured for 72 hours under the condition of 37° C., 5% $CO_2$. A group of no antibody addition and a group of 100% cell death with 1% Tween80 were also prepared. To each well, 10 µL of Cell Counting Kit-8 (DOJINDO LABORATORIES) were added, and color reaction was carried out in the condition of 37° C., 5% $CO_2$ for 3 hours. Then, the absorbance at 450 nm was measured using a microplate reader (iMark, Bio-Rad Laboratories, Inc), and the cell growth inhibition activity (%) was calculated according to the following formula (1).

$$\text{Growth inhibition activity (\%)} = 100 - \left( \frac{OD_{addition}^{antibody} - OD_{100\% \text{ cell death}}}{OD_{addition}^{no \ antibody} - OD_{100\% \text{ cell death}}} \times 100 \right) \quad (1)$$

The results are shown in FIG. 3. The vertical axis in the figure shows the growth inhibition activity, and the horizontal axis shows the concentration of soluble IgM added to the medium.

The growth inhibition activity of the anti-IgM antibody (1) decreased, as the soluble IgM concentration increased. In contrast, the anti-IgM (1)/HLA-DR (1) bispecific antibody retained the growth inhibition activity even when the soluble IgM concentration increased. Furthermore, the growth inhibition activities of the Cys1m type bispecific antibody and the KIH type bispecific antibody were comparable, thus it has been shown that there is no difference in activity due to the difference in the production method.

(1-2) Growth Inhibition Activity Against JeKo-1 Cells 2

According to Example 4(1-1), the changes due to increase of the soluble IgM concentration in growth inhibition activities of the anti-IgM antibody (1), the anti-HLA-DR antibody (1), a combination use of the anti-IgM antibody (1) and the anti-HLA-DR antibody (1), the anti-IgM (1)/HLA-DR (1) bispecific antibody and the negative control antibody against JeKo-1 cells were investigated. The antibody concentration was set to 300 ng/mL. When used in combination, anti-IgM antibody (1) and anti-HLA-DR antibody (1) were added at 300 ng/mL respectively (total 600 ng/mL). The results are shown in FIG. 4. The vertical axis in the figure shows the growth inhibition activity, and the horizontal axis shows the concentration of soluble IgM added to the medium.

When the combination of anti-IgM antibody (1) and anti-HLA-DR antibody (1) was used, similarly to the result of the anti-IgM antibody (1) alone, the growth inhibition activity decreased, as the soluble IgM concentration increased. In contrast, the anti-IgM (1)/HLA-DR (1) bispecific antibody retained the growth inhibition activity even when the soluble IgM concentration increased.

From the above, it has been shown that anti-IgM (1)/HLA-DR (1) bispecific antibody has superior growth inhibition activity than the combination use of both parent antibodies.

(1-3) Growth Inhibition Activity Against B104 Cells

According to Example 4(1-1), the changes due to increase of the soluble IgM concentration in the growth inhibition activities of the anti-IgM antibody (1), the anti-HLA-DR antibody (1), the anti-IgM (1)/HLA-DR (1) bispecific antibody and the negative control antibody (100 ng/mL) against B104 cells instead of JeKo-1 cells were investigated. The B104 cells (JCRB0117, JCRB cell bank) are a cell line derived from human B cell tumor, which expresses IgM, HLA-DR, CD20, CD38 and CD52 on the cell surface. The B104 cells were cultured under the condition of 37° C., 5% $CO_2$ using B104 cell growth medium. The B104 cell growth medium was RPMI 1640 containing a 20% FBS and 1% penicillin-streptomycin solution. For dilution of the soluble IgM, the B104 cell growth medium was used. The results of the test are shown in FIG. 5. The vertical axis in the figure shows the growth inhibition activity, and the horizontal axis shows the concentration of soluble IgM added to the medium.

The growth inhibition activity of the anti-IgM antibody (1) decreased, as the soluble IgM concentration increased. In contrast, the anti-IgM (1)/HLA-DR (1) bispecific antibody retained the growth inhibition activity even when the soluble IgM concentration increased. In addition, the growth inhibition activities of the Cys1m type bispecific antibody and the KIH type bispecific antibody were comparable, thus it has been shown that there is no difference in activity due to the difference in the production method.

The similar results of growth inhibition activities of anti-IgM (1)/HLA-DR (1) bispecific antibody in the presence of soluble IgM were obtained in two different cells of JeKo-1 cells and B104 cells. Thus, it has been considered that the growth inhibition activity of the anti-IgM (1)/HLA- DR (1) bispecific antibody can be exhibited against a cell, even in the presence of soluble IgM, as long as the cell expresses both IgM and HLA-DR.

(1-4) Growth Inhibition Activity Against B104 Cells

According to Example 4(1-1), the changes due to increase of the soluble IgM concentration in the growth inhibition activities of the anti-IgM antibody (2), the anti-HLA-DR antibody (1), the anti-IgM (2)/HLA-DR (1) bispecific antibody and the negative control antibody against B104 cells were investigated. The antibody concentration was 500 ng/mL. The results are shown in FIG. 20. The vertical axis in the figure shows the growth inhibition activity, and the horizontal axis shows the concentration of soluble IgM added to the medium.

The growth inhibition activity of the anti-IgM antibody (2) decreased, as the soluble IgM concentration increased. In contrast, the anti-IgM (2)/HLA-DR (1) bispecific antibody retained the growth inhibition activity even when the soluble IgM concentration increased.

(1-5) Growth Inhibition Activity Against JeKo-1 Cells

According to Example 4(1-1), the changes due to increase of the soluble IgM concentration in the growth inhibition activities of the anti-IgM antibody (3), the anti-HLA-DR antibody (1), the anti-IgM (3)/HLA-DR (1) bispecific antibody and the negative control antibody against JeKo-1 cells were investigated. The antibody concentration was 500 ng/mL. The results are shown in FIG. 21. The vertical axis in the figure shows the growth inhibition activity, and the horizontal axis shows the concentration of soluble IgM added to the medium.

The growth inhibition activity of the anti-IgM antibody (3) decreased, as the soluble IgM concentration increased. In contrast, the anti-IgM (3)/HLA-DR (1) bispecific antibody retained the growth inhibition activity even when the soluble IgM concentration increased.

(1-6) Growth Inhibition Activity Against B104 Cells

According to Example 4(1-1), the changes due to increase of the soluble IgM concentration in the growth inhibition activities of the anti-IgM antibody (4), the anti-HLA-DR antibody (1), the anti-IgM (4)/HLA-DR (1) bispecific antibody and the negative control antibody against B104 cells were investigated. The antibody concentration was 500 ng/mL. The results are shown in FIG. 22. The vertical axis in the figure shows the growth inhibition activity, and the horizontal axis shows the concentration of soluble IgM added to the medium.

The growth inhibition activity of the anti-IgM antibody (4) decreased, as the soluble IgM concentration increased. In contrast, the anti-IgM (4)/HLA-DR (1) bispecific antibody retained the growth inhibition activity even when the soluble IgM concentration increased.

(1-7) Growth Inhibition Activity Against B104 Cells

According to Example 4(1-1), the changes due to increase of the soluble IgM concentration in the growth inhibition activities of the anti-IgM antibody (5), the anti-HLA-DR antibody (1), the anti-IgM (5)/HLA-DR (1) bispecific antibody and the negative control antibody against B104 cells were investigated. The antibody concentration was 500 ng/mL. The results are shown in FIG. 23. The vertical axis in the figure shows the growth inhibition activity, and the horizontal axis shows the concentration of soluble IgM added to the medium.

The growth inhibition activity of the anti-IgM antibody (5) decreased, as the soluble IgM concentration increased. In contrast, the anti-IgM (5)/HLA-DR (1) bispecific antibody retained the growth inhibition activity even when the soluble IgM concentration increased.

The similar results were obtained regardless of the clones of the anti-IgM antibody combined with the anti-B cell surface antigen antibody. Thus, it has been shown that the anti-IgM/B cell surface antigen bispecific antibody has growth inhibition activity in the presence of soluble IgM in any clone of the anti-IgM antibody.

(1-8) Growth Inhibition Activity Against B104 Cells

According to Example 4(1-1), the changes due to increase of the soluble IgM concentration in the growth inhibition activities of the anti-IgM antibody (1), the anti-HLA-DR antibody (2), the anti-IgM (1)/HLA-DR (2) bispecific antibody and the negative control antibody against B104 cells were investigated. The antibody concentration was 500 ng/mL. The results are shown in FIG. 24. The vertical axis in the figure shows the growth inhibition activity, and the horizontal axis shows the concentration of soluble IgM added to the medium.

The growth inhibition activity of the anti-IgM antibody (1) decreased, as the soluble IgM concentration increased. In contrast, the anti-IgM (1)/HLA-DR (2) bispecific antibody retained the growth inhibition activity even when the soluble IgM concentration increased.

The similar results were obtained regardless of the clones of the anti-HLA-DR antibody combined with the anti-B cell surface antigen antibody. Thus, it has been shown that the anti-IgM/HLA-DR bispecific antibody has growth inhibition activity in the presence of soluble IgM in any clone of the anti-HLA-DR antibody.

(1-9) Growth Inhibition Activity Against JeKo-1 Cells in the Presence of Human Serum The growth inhibition activities of the anti-IgM antibody (1), the anti-HLA-DR antibody (1), the anti-IgM (1)/HLA-DR (1) bispecific antibody and the negative control antibody against JeKo-1 cells were investigated in the presence of human serum. Specifically, human serum collected from healthy volunteers was inactivated by a treatment of 56° C. for 30 minutes. Furthermore, the antibodies were prepared to be 10-fold at the final concentration (100 μg/mL) with PBS. For the measurement of the viability, RealTime-Glo MT Cell Viability Assay (Promega Corporation) was used. In the test, human serum and the antibody were mixed so as to form a 90% human serum/10% antibody solution (the final concentration of the antibody was 10 μg/mL). For a no human serum addition group, 90% JeKo-1 cell growth medium/10% antibody solution was prepared. To a 96-well plate to which the JeKo-1 cells were seeded ($1.5 \times 10^4$ cells/well) in advance, the mixed solution was added, and furthermore, 10 μL of the reaction solution was added in accordance with the instruction. After the resultant was cultured under the condition of 37° C., 5% $CO_2$ for 48 hours, the luminescence was measured using a microplate reader (GloMax Discover, GM3000, Promega Corporation) and the cell viability (%) was quantified according to the following formula (2).

$$\text{Viability (\%)} = \frac{OD_{antibody\ addition}}{OD_{no\ antibody\ addition}} \times 100 \qquad (2)$$

The significant difference test was performed by Student's t-test. The results are shown in FIG. 6. The vertical axis in the figure shows the cell viability.

In the condition of "serum (−)", the anti-IgM antibody (1) showed a growth inhibition activity against B cell tumor cells, while in the condition of "serum (+)", the anti-IgM antibody (1) lost the growth inhibition activity against B cell tumor cells. In contrast, the anti-IgM (1)/HLA-DR (1)

bispecific antibody showed the growth inhibition activity regardless of the presence or absence of serum. Furthermore, the growth inhibition activities of the Cys1m type bispecific antibody and the KIH type bispecific antibody were comparable, thus it has been shown that there is no difference in activity due to the difference in the production method.

From the above, it has been shown that anti-IgM antibody loses the growth inhibition activity in the presence of human serum, while the anti-IgM/HLA-DR bispecific antibody retains the activity even in the presence of serum.

This test was carried out using sera from two human donors, and comparable results were obtained between inactivated sera from each of the donors, thus no difference due to donors was observed.

(2) Bispecific Antibody Combining Anti-IgM Antibody and Anti-CD20 Antibody (2-1) Growth Inhibition Activity Against JeKo-1 Cells 1

According to Example 4(1-1), the changes due to increase of the soluble IgM concentration in the growth inhibition activities of the anti-IgM antibody (1), the anti-CD20 antibody (1), the anti-IgM (1)/CD20 (1) bispecific antibody and the negative control antibody (300 ng/mL) against Jeko-1 cells were investigated. The results are shown in FIG. 7. The vertical axis in the figure shows the growth inhibition activity, and the horizontal axis shows the concentration of soluble IgM added to the medium.

The growth inhibition activity of the anti-IgM antibody (1) decreased, as the soluble IgM concentration increased. In contrast, the anti-IgM (1)/CD20 (1) bispecific antibody retained the growth inhibition activity even when the soluble IgM concentration increased. Furthermore, the growth inhibition activities of the Cys1m type bispecific antibody and the KIH type bispecific antibody were comparable, thus it has been shown that there is no difference in activity due to the difference in the production method.

(2-2) Growth Inhibition Activity Against JeKo-1 Cells 2

The study of the bispecific antibody combining the anti-CD20 antibody (2) was carried out. The anti-CD20 antibody (2) is different from the anti-CD20 antibody (1) used in the Example 4(2-1) in the originated clone. According to Example 4(1-1), the changes due to increase of the soluble IgM concentration in the growth inhibition activities of the anti-IgM antibody (1), the anti-CD20 antibody (2), the anti-IgM (1)/CD20 (2) bispecific antibody and the negative control antibody (1,000 ng/mL) against Jeko-1 cells were investigated. The results are shown in FIG. 8. The vertical axis in the figure shows the growth inhibition activity, and the horizontal axis shows the concentration of soluble IgM added to the medium.

The growth inhibition activity of the anti-IgM antibody (1) decreased, as the soluble IgM concentration increased. In contrast, the anti-IgM (1)/CD20 (2) bispecific antibody retained the growth inhibition activity even when the soluble IgM concentration increased.

Similar results were obtained even when the anti-CD20 antibody combined with anti-IgM antibody is an anti-CD20 antibody (1) or an anti-CD20 antibody (2). Thus, it has been shown that the anti-IgM/CD20 bispecific antibody has growth inhibition activity in the presence of soluble IgM in any clone of the anti-CD20 antibody.

(2-3) Growth Inhibition Activity Against B104 Cells

According to Example 4(1-1), the changes due to increase of the soluble IgM concentration in the growth inhibition activities of the anti-IgM antibody (1), anti-CD20 antibody (1), anti-IgM (1)/CD20 (1) bispecific antibody and the negative control antibody (1,000 ng/mL) against B104 cells were investigated. For the culture of the B104 cells and the dilution of soluble IgM, the B104 cell growth medium was used. The results are shown in FIG. 9. The vertical axis in the figure shows the growth inhibition activity, and the horizontal axis shows the concentration of soluble IgM added to the medium.

The growth inhibition activity of the anti-IgM antibody (1) decreased, as the soluble IgM concentration increased. In contrast, the anti-IgM (1)/CD20 (1) bispecific antibody retained the growth inhibition activity even when the soluble IgM concentration increased. In addition, the growth inhibition activities of the Cys1m type bispecific antibody and the KIH type bispecific antibody were comparable, thus it has been shown that there is no difference in activity due to the difference in the production method.

The similar results of the growth inhibition activities of the anti-IgM (1)/CD20 (1) bispecific antibody in the presence of soluble IgM were obtained in two different cells of JeKo-1 cells and B104 cells. Thus, it has been shown that the growth inhibition activity of the anti-IgM/CD20 bispecific antibody can be exhibited against a cell, even in the presence of soluble IgM, as long as the cell expresses both IgM and CD20 antigen on the cell membrane surface.

(2-4) Growth Inhibition Activity Against JeKo-1 Cells in the Presence of Human Serum According to Example 4(1-9), the growth inhibition activities of the anti-IgM antibody (1), the anti-CD20 antibody (1), the anti-IgM (1)/CD20 (1) bispecific antibody and the negative control antibody (1 µg/mL) against JeKo-1 cells were investigated in the presence of human serum. The results are shown in FIG. 10. The significant difference test was performed by Student's t-test. The vertical axis in the figure shows viability.

In the condition of "serum (−)", the anti-IgM antibody (1) showed a growth inhibition activity against B cell tumor cells, while in the condition of "serum (+)", the anti-IgM antibody (1) lost the growth inhibition activity against the B cell tumor cells. In contrast, the anti-IgM (1)/CD20 (1) bispecific antibody showed the growth inhibition activity regardless of the presence or absence of serum. In addition, the growth inhibition activities of the Cys1m type bispecific antibody and the KIH type bispecific antibody were comparable, thus it has been shown that there is no difference in activity due to the difference in the production method.

From the above, it has been shown that the anti-IgM antibody loses the growth inhibition activity in the presence of human serum, while the anti-IgM/CD20 bispecific antibody retains the activity even in the presence of serum.

This test was carried out using sera from two human donors, and comparable results were obtained between inactivated sera from each of the donors, thus no difference due to donors was observed.

(3) Bispecific Antibody Combining Anti-IgM Antibody and Anti-CD32b Antibody (3-1) Growth Inhibition Activity Against JeKo-1 Cells According to Example 4(1-1), the changes due to increase of the soluble IgM concentration in the growth inhibition activities of anti-IgM antibody (1), the anti-CD32b antibody, the anti-IgM (1)/CD32b antibody and the negative control antibody (300 ng/mL) against JeKo-1 cells were investigated.

The obtained results of the growth inhibition activities of the anti-IgM antibody (1) and the anti-IgM (1)/CD32b antibody showed similar tendency to the results of Example 4(1-1).

(4) Bispecific Antibody Combining Anti-IgM Antibody and Anti-CD37 Antibody

(4-1) Growth Inhibition Activity Against Ramos Cells

According to Example 4(1-1), the changes due to increase of the soluble IgM concentration in the growth inhibition activities of the anti-IgM antibody (1), the anti-CD37 antibody, the anti-IgM (1)/CD37 bispecific antibody and the negative control antibody (1,000 ng/mL) against Ramos cells were investigated. The Ramos cells express IgM and CD37 on the cell surface. For the culture of the Ramos cells and the dilution of soluble IgM, the Ramos cell growth medium was used.

The obtained results of the growth inhibition activities of anti-IgM antibody (1) and anti-IgM (1)/CD37 antibody showed similar tendency to the results of Example 4(1-1).

(5) Bispecific Antibody Combining Anti-IgM Antibody and Anti-CD52 Antibody

(5-1) Growth Inhibition Activity Against B104 Cells

According to Example 4(1-1), the changes due to increase of the soluble IgM concentration in the growth inhibition activities of the anti-IgM antibody (1), the anti-CD52 antibody, the anti-IgM (1)/CD52 bispecific antibody and the negative control antibody (1,000 ng/mL) against B104 cells were investigated. For the culture of the B104 cells and the dilution of soluble IgM, the B104 cell growth medium was used. The results are shown in FIG. 11. The vertical axis in the figure shows the growth inhibition activity, and the horizontal axis shows the concentration of soluble IgM added to the medium.

The growth inhibition activity of the anti-IgM antibody (1) decreased, as the soluble IgM concentration increased. In contrast, the anti-IgM (1)/CD52 bispecific antibody retained the growth inhibition activity even when the soluble IgM concentration increased.

From the results of Examples 4(1) to (5), it has been suggested that the anti-IgM/B cell surface antigen antibody of the present invention shows the cell growth inhibition activity against B cells in the presence of soluble IgM regardless of the kind of the B cell surface antigen.

(6) Bispecific Antibody Combining Anti-IgM Antibody and Anti-BAFF Receptor Antibody

(6-1) Growth Inhibition Activity Against JeKo-1 Cells or B104 Cells

According to Example 4(1-1), the changes due to increase of the soluble IgM concentration in the growth inhibition activities of the anti-IgM antibody, the anti-BAFF receptor antibody, the anti-IgM/BAFF receptor bispecific antibody and the negative control antibody against JeKo-1 cells or B104 cells are investigated. For the culture of the cells and the dilution of soluble IgM, the growth medium for the relevant cells is used.

(7) Bispecific Antibody Combining Anti-IgM Antibody and Anti-BCMA Antibody

(7-1) Growth Inhibition Activity Against Ramos Cells or B104 Cells

According to Example 4(1-1), the changes due to increase of the soluble IgM concentration in the growth inhibition activities of the anti-IgM antibody, the anti-BCMA antibody, the anti-IgM/BCMA bispecific antibody and the negative control antibody against Ramos cells or B104 cells are investigated. For the culture of the cells and the dilution of soluble IgM, the growth medium for the relevant cells is used.

(8) Bispecific Antibody Combining Anti-IgM Antibody and Anti-TACI Antibody

(8-1) Growth Inhibition Activity Against JeKo-1 Cells or B104 Cells

According to Example 4(1-1), the changes due to increase of the soluble IgM concentration in the growth inhibition activities of the anti-IgM antibody, the anti-TACI antibody, the anti-IgM/TACI bispecific antibody and the negative control antibody against JeKo-1 cells or B104 cells are investigated. For the culture of the cells and the dilution of soluble IgM, the growth medium for the relevant cells is used.

(9) Bispecific Antibody Combining Anti-IgM Antibody and Anti-CD38 Antibody

(9-1) Growth Inhibition Activity Against B104 Cells

According to Example 4(1-1), the changes due to increase of the soluble IgM concentration in the growth inhibition activities of the anti-IgM antibody (1), the anti-CD38 antibody, the anti-IgM (1)/CD38 bispecific antibody and the negative control antibody (500 ng/mL) against B104 cells were investigated. For the culture of the B104 cells and the dilution of soluble IgM, the B104 cell growth medium was used. The results are shown in FIG. 25. The vertical axis in the figure shows the growth inhibition activity, and the horizontal axis shows the concentration of soluble IgM added to the medium.

The growth inhibition activity of the anti-IgM antibody (1) decreased, as the soluble IgM concentration increased. In contrast, the anti-IgM (1)/CD38 bispecific antibody retained the growth inhibition activity even when the soluble IgM concentration increased.

(10) Bispecific Antibody Combining Anti-IgM Antibody and Anti-CD81 Antibody

(10-1) Growth Inhibition Activity Against JeKo-1 Cells

According to Example 4(1-1), the changes due to increase of the soluble IgM concentration in the growth inhibition activities of the anti-IgM antibody (1), the anti-CD81 antibody, the anti-IgM (1)/CD81 bispecific antibody and a negative control antibody (500 ng/mL) against JeKo-1 cells were investigated. For the culture of the JeKo-1 cells and the dilution of soluble IgM here, the JeKo-1 cell growth medium was used. The results are shown in FIG. 26. The vertical axis in the figure shows the growth inhibition activity, and the horizontal axis shows the concentration of soluble IgM added to the medium.

The growth inhibition activity of the anti-IgM antibody (1) decreased, as the soluble IgM concentration increased. In contrast, the anti-IgM (1)/CD81 bispecific antibody retained the growth inhibition activity even when the soluble IgM concentration increased.

Furthermore, from the results of Examples 4(9) and (10), it has been suggested that the anti-IgM/B cell surface antigen antibody of the present invention shows the cell growth inhibition activity against B cells in the presence of soluble IgM regardless of the kind of the B cell surface antigen.

Example 5 Apoptosis Inducing Effect of Bispecific Antibody on Ramos Cells

(1) Apoptosis Inducing Effect of Bispecific Antibody Combining Anti-IgM Antibody and Anti-HLA-DR Antibody on Ramos Cells Apoptosis inducing effects of the anti-IgM antibody (1), the anti-HLA-DR antibody (1), the anti-IgM (1)/HLA-DR (1) bispecific antibody and the negative control antibody (1,000 ng/mL) on Ramos cells were investigated. Ramos cells suspended in medium in advance were seeded to a 6-well plate (3.6×10$^5$ cells/well), and cultured under the condition of 37° C., 5% $CO_2$ for 3 hours. Each solution of the anti-IgM antibody (1), the anti-HLA-DR antibody (1), the anti-IgM (1)/HLA-DR (1) bispecific antibody or the negative control antibody prepared to be 1 mg/ml in PBS was added to each well to be 1,000 ng/ml at the final concentration, and cultured under the condition of 37° C., 5% $CO_2$ for further 24 hours. Cells collected by centrifugation were suspended in PBS containing 1% glutaraldehyde, and incubated under the condition of 4° C. for 16 hours. Again, after collecting the cells by centrifugation, they were suspended in 40 µL of PBS.

After mixing 10 µL of the cell suspension and 2 µL of 1 mM Hoechst 33342 (DOJINDO LABORATORIES), the mixture was observed under a fluorescence microscope. The cells in which the chromosome structures were aggregated or fragmented were determined as apoptotic cells. Ten fields of view were selected randomly, and the total cell number and the number of apoptotic cells in the fields were counted.

The results are shown in FIG. 27. The significant differences were determined by Student's t-test. The vertical axis in the figure shows the percentage of apoptotic cells.

The percentage of apoptotic cells of the anti-IgM antibody (1) and the anti-HLA-DR antibody (1) were 6.0% and 4.2%, respectively, and the percentage of apoptotic cells of the vehicle and the negative antibody were 3.8% and 4.3%, respectively. The bispecific antibody showed the percentage of apoptotic cells of 11.0%, which was significantly higher than any of those of other antibodies.

(2) Apoptosis Inducing Effect of Bispecific Antibody Combining Anti-IgM Antibody (1) and Anti-CD20 (2) Antibody on Ramos Cells According to Example 5(1), the percentage of apoptotic cells was investigated using the bispecific antibody combining the anti-IgM antibody (1) and the anti-CD20 antibody (2), in place of the bispecific antibody combining the anti-IgM antibody (1) and the anti-HLA-DR antibody (1).

The results are shown in FIG. 28. The vertical axis in the figure shows the percentage of apoptotic cells.

The percentage of apoptotic cells of the anti-IgM antibody (1) and the anti-CD20 antibody (2) were 8.7% and 7.9%, respectively, and the percentage of apoptotic cells of the vehicle and the negative antibody were 3.5% and 4.1%, respectively. In contrast, the bispecific antibody showed the percentage of apoptotic cells of 22.4%, which was significantly higher than any of those of the other antibodies.

(3) Apoptosis inducing effect of bispecific antibody combining anti-IgM antibody and anti-CD38 antibody on Ramos cells According to Example 5(1), the percentage of apoptotic cells was investigated using the bispecific antibody combining the anti-IgM antibody (1) and the anti-CD38 antibody, in place of the bispecific antibody combining the anti-IgM antibody (1) and the anti-HLA-A-DR: antibody.

The results are shown in FIG. 29. The vertical axis in the figure shows the percentage of apoptotic cells in the total cells.

The percentage of apoptotic cells of the anti-IgM antibody (1) and the anti-CD38 antibody were 4.3% and 1.4%, respectively, and the percentage of apoptotic cells of the vehicle and the negative antibody were 1.3% and 1.1%, respectively. In contrast, the bispecific antibody showed the percentage of apoptotic cells of 16.4%, which was significantly higher than any of those of the other antibodies.

Example 6 Cell Cycle Arrest Effect of Bispecific Antibody Combining Anti-IgM Antibody and Anti-HLA-DR Antibody (1) Cell Cycle Arrest Effect on JeKo-1 Cells in the Presence of Soluble IgM The effects of the anti-IgM antibody (1), the anti-HLA-DR antibody (1) and the anti-IgM (1)/HLA-DR (1) bispecific antibody on JeKo-1 cell cycle were investigated in the presence of soluble IgM. Specifically, each antibody prepared in the JeKo-1 cell growth medium (400 ng/mL) and soluble IgM (40 µg/mL) were mixed at a volume ratio of 1:1. The mixture was allowed to stand at room temperature for 30 minutes. Thereafter, the JeKo-1 cells suspended in the medium in advance were seeded in 6-well plates (3×10$^5$ cells/well), and to each well, the mixture was added so that the concentration of each antibody was 100 ng/mL and the concentration of soluble IgM was 10 µg/mL, and the resultant was cultured under the condition of 37° C., 5% $CO_2$ for 24 hours. For the negative control, PBS was added instead of the antibody solution. After culturing, the cells were fixed with 70% ethanol/PBS, and staining of DNA was performed with propidium iodide (Sigma-Aldrich), and then cell cycle analysis was performed by a flow cytometer and an analysis software Cytomics MXP cytometer. The results are shown in FIG. 12. The vertical axis of each slide shows the number of cells, and the horizontal axis shows the DNA content per cell.

The anti-HLA-DR antibody (1) did not affect the cell cycle of JeKo-1 cells regardless of the presence of soluble IgM. The anti-IgM antibody (1) arrested the cell cycle in the absence of soluble IgM, but the cell cycle arrest effect was disappeared by the addition of soluble IgM. In contrast, the anti-IgM (1)/HLA-DR (1) bispecific antibody arrested the cell cycle at G1 phase regardless of the presence of soluble IgM. In addition, the cell cycle arrest effects of the Cys1m type bispecific antibody and the KIH type bispecific antibody were comparable, thus it has been shown that there is no difference in activity due to the difference in the production method.

From this result, it has been revealed that the cell cycle can be arrested even in the presence of soluble IgM by a bispecific antibody combining the anti-IgM antibody and an antibody against B cell surface antigen.

(2) Cell Cycle Arrest Effect on JeKo-1 Cells in the Presence of Human Serum

According to Example 6(1), but in the presence of human serum in place of the soluble IgM, the effects of the anti-IgM antibody (1), the anti-HLA-DR antibody (1) and the anti-IgM (1)/HLA-DR (1) bispecific antibody (1 g/mL) on the cell cycle of JeKo-1 cells were investigated. Specifically, the human serum and the antibody were mixed so as to form a 90% human serum/10% antibody solution (the final concentration of the antibody was 1 µg/mL), and the mixture was added to JeKo-1 cells. For a no human serum addition group, 90% JeKo-1 cell growth medium/10% antibody solution was prepared. For the negative control, PBS was added instead of the antibody solution. The results are shown in FIG. 13. The vertical axis of each graph shows the number of cells and the horizontal axis shows the DNA content per cell.

The anti-HLA-DR antibody (1) did not affect the cell cycle of JeKo-1 cells regardless of the presence of human serum. The anti-IgM antibody (1) arrested the cell cycle in the absence of human serum, but the cell cycle arrest effect was disappeared by the addition of human serum. In contrast, anti-IgM (1)/HLA-DR (1) bispecific antibody arrested the cell cycle at G1 phase regardless of the presence of human serum. In addition, the cell cycle arrest effects of the Cys1m type bispecific antibody and the KIH type bispecific antibody were comparable, thus it has been shown that there is no difference in activity due to the difference in the production method.

From this result, it has been revealed that the cell cycle can be arrested even in the presence of human serum by a bispecific antibody combining the anti-IgM antibody and an antibody against B cell surface antigen.

This test was carried out using sera from two human donors, and comparable results were obtained between inactivated sera from each of the donors, thus no difference due to donors was observed.

Example 7 Administration Study of Bispecific Antibody Combining Anti-IgM Antibody and Anti-HLA-DR Antibody to Rats (1) B Cell Reducing Effect of Antibody Administration to Rats It is known that the anti-HLA-DR antibody (1) binds to B cells of WKAH/Hkm rats. Then, the effect of the anti-IgM/HLA-DR (1) bispecific antibody on the rats was studied.

The anti-IgM antibody (1, 3, 10, 30 mg/kg), the anti-HLA-DR antibody (1) (0.1, 0.3, 1 mg/kg) and the anti-IgM/HLA-DR (1) bispecific antibody (0.1, 0.3, 1, 3, 10, 30 mg/kg) were administered to WKAH/Hkm rats via the tail vein. At five hours after administration, blood was collected from the rat tail vein. Blood was reacted with PE-labeled anti-rat CD45RA antibody (BD Pharmingen), and then a hemolysis treatment was performed with OptiLyse C (Beckman Coulter). Subsequently, the number of B cells in the blood was measured by a flow cytometer and an analysis software Cytomics MXP cytometer. The number of B cells in peripheral blood of an individual treated with PBS instead of the antibody was decided as 100%, and the variation of the number of B cells in peripheral blood after administration of each antibody was calculated.

The effect of administration of the anti-IgM/HLA-DR (1) bispecific antibody on B cells in the rat in vivo is shown in FIG. 14. Although the anti-IgM antibody did not reduce the number of B cells unless administered in the dose of 10 mg/kg or more, the anti-IgM/HLA-DR (1) bispecific antibody reduced the number of B cells even in the 0.3 mg/kg administration group. In the individuals to which the anti-HLA-DR antibody (1) was administered at 0.3 mg/kg or more, behavior abnormalities such as passive behavior or recumbency were observed. Furthermore, in the individuals to which the anti-HLA-DR antibody (1) was administered at 1 mg/kg, serious adverse effects were found and thus blood sampling became impossible. In addition, when the anti-HLA-DR antibody (1) was administered at the dose less than the above, sufficient effect of reducing B cells was not observed. From the results above, it has been shown that, even at low concentrations where the activity of the anti-IgM antibody cannot be exerted in the rat in vivo, a bispecific antibody combining the anti-IgM antibody and other antibody against B cell surface antigen can reduce the number of B cells. It has also been shown that, although the anti-B cell antigen antibody causes serious adverse effects even at low concentration in the rat in vivo, a bispecific antibody combining the anti-IgM antibody and the anti-B cell antigen antibody can suppress adverse effects and reduce the number of B cells.

Example 8 Administration Study of Bispecific Antibody Combining Anti-IgM Antibody and Anti-HLA-DR Antibody to Monkeys (1) B Cell Reducing Effect of Antibody Administration to Cynomolgus Monkey The anti-IgM (1)/HLA-DR (1) bispecific antibody was administered to cynomolgus monkeys, and the efficacy thereof was evaluated. The anti-IgM (1)/HLA-DR (1) bispecific antibody was administered into the cephalic vein of one female cynomolgus monkey. Administration was performed at doses of the anti-IgM (1)/HLA-DR (1) bispecific antibody respectively corresponding to 1, 3, 10, 20 mg/kg in this order from low dose, once every two days for four times in total. Blood was collected from the femoral vein, just before the first administration, and 24 hours after each administration. To the collected blood, APC-labeled anti-CD20 antibody (BioLegend, Inc) or Alexa Fluor 488-labeled anti-CD3 antibody (BD Biosciences) was reacted. Then, the numbers of B cells and T cells were measured by a flow cytometer (FACS Calibur, BD Biosciences) and an analysis software CellQuest Pro (Version 6.0, BD Biosciences). The number of red blood cells and platelets were measured using a general hematology testing apparatus (Siemens Healthcare Diagnostics Manufacturing Ltd). The number of blood cells in the peripheral blood before administration was defined as 100%, and the number of blood cells in the peripheral blood after each administration was calculated. Furthermore, the symptoms of monkey were observed throughout the dosing period, and after the test, the presence or absence of abnormal findings was observed.

The results are shown in FIGS. 15 to 19. By the administration of the anti-IgM (1)/HLA-DR (1) bispecific antibody at 1 mg/kg dose, the number of B cells in peripheral blood was reduced to about 50%. The effect was enhanced in a concentration-dependent manner, and at 20 mg/kg dose, the number of B cells in peripheral blood was eliminated to about 2% of the concentration before administration (FIG. 15). Furthermore, in a hematoxylin-eosin staining of axillary lymph nodes prepared after antibody administration, the proportion of lymphocytes in the lymph nodes was significantly reduced, and the atrophy of lymphoid follicles and the loss of germinal center were observed. In contrast, regarding T cells which express HLA-DR on the cell membrane surface as like B cells, the decrease depending on the antibody administration was not observed (FIG. 16). In addition, regarding red blood cells and platelets which do not express HLA-DR on the cell membrane surface, the decrease depending on the antibody administration was also not observed (FIGS. 17 and 18). Furthermore, the body temperature didn't change after the antibody administration, and stayed almost constant (FIG. 19). No abnormal conditions likely due to the antibody administration were observed in the monkey. Furthermore, no abnormal findings were found at autopsy.

These results show that the anti-IgM (1)/HLA-DR (1) bispecific antibody leads to depletion of peripheral blood B cells in the cynomolgus monkey in vivo irrespective of the presence of soluble IgM in the blood. Thus, the result strongly suggests that the bispecific antibody is effective in treatment of not only a B cell tumor but also a B cell-related disease derived from normal B cells.

As for the anti-HLA-DR antibody (1), which is one of the parental antibody of the anti-IgM (1)/HLA-DR (1) bispecific antibody, adverse effects on rats were observed from 0.3 mg/kg, as shown in Example 6. Furthermore, a serious adverse effect on rats was observed at a dose of 1 mg/kg, suggesting a possibility of similar serious adverse effects in cynomolgus monkey. However, the results above show that, although the anti-B cell antigen antibody may cause serious adverse effects in the cynomolgus monkey in vivo, a bispecific antibody combining the anti-IgM antibody and the anti-B cell antigen antibody can suppress adverse effects and reduce the number of B cells, even it is used at high concentration.

From the results of Examples 7 and 8, it has been shown that the anti-IgM/B cell surface antigen bispecific antibody has an excellent growth inhibition activity against B cells and also has a significant advantage in terms of suppressing adverse effects.

The invention claimed is:

1. A bispecific antibody, which binds to IgM and a B cell surface antigen CD22 and comprises a first antigen-binding site which binds to the IgM comprising CDRs consisting of SEQ ID NOs: 1-6, SEQ ID NOs: 48-53, SEQ ID NOs: 60-65, SEQ ID NOs: 66-71, SEQ ID NOs: 72-77, or SEQ ID NOs: 78-83.

2. The bispecific antibody according to claim 1, wherein the bispecific antibody comprises a second antigen-binding site which binds to the B cell surface antigen.

3. The bispecific antibody according to claim 1, wherein the B cell surface antigen is selected from the group consisting of HLA-DR, CD20, CD32b, CD37, CD38, CD52, CD81, a BAFF receptor, BCMA, and TACI.

4. The bispecific antibody according to claim 1, wherein the bispecific antibody is a chimeric antibody, a humanized antibody or a human antibody.

5. The bispecific antibody according to claim 1, wherein the bispecific antibody inhibits B cell growth.

6. A pharmaceutical composition, comprising the bispecific antibody according to claim 1.

7. An agent for treating a B cell-related disease, comprising the bispecific antibody according to claim 1 as an active ingredient.

8. The agent for treating a B cell-related disease according to claim 7, wherein the B cell-related disease is a B cell tumor.

9. A method for producing an agent for treating a B cell-related disease, comprising producing the bispecific antibody of claim 1 as an active ingredient.

10. The method according to claim 9, wherein the B cell-related disease is a B cell tumor.

11. The bispecific antibody according to claim 1, which is configured for use in treating a B cell-related disease.

12. The bispecific antibody according to claim 11, wherein the B cell-related disease is a B cell tumor.

13. A method for treating a B cell-related disease, comprising administering an effective amount of the bispecific antibody according to claim 1.

14. The method for treating a B cell-related disease according to claim 13, wherein the B cell-related disease is a B cell tumor.

15. The bispecific antibody according to claim 1, which comprises:
   (a) CDRs consisting of SEQ ID NOs: 1-12;
   (b) CDRs consisting of SEQ ID NOs: 1-6 and 13-18;
   (c) CDRs consisting of SEQ ID NOs: 1-6 and 19-24;
   (d) CDRs consisting of SEQ ID NOs: 1-6, 25-26, FDY, and SEQ ID NOs: 27-29;
   (e) CDRs consisting of SEQ ID NOs: 1-6 and 30-35;
   (f) CDRs consisting of SEQ ID NOs: 1-6 and 36-41;
   (g) CDRs consisting of SEQ ID NOs: 1-6 and 42-47;
   (h) CDRs consisting of SEQ ID NOs: 48-53 and 7-12;
   (i) CDRs consisting of SEQ ID NOs: 60-65 and 7-12;

(j) CDRs consisting of SEQ ID NOs: 66-71 and 7-12;
(k) CDRs consisting of SEQ ID NOs: 72-77 and 7-12;
(l) CDRs consisting of SEQ ID NOs: 78-83 and 7-12;
(m) CDRs consisting of SEQ ID NOs: 1-6 and 84-89;
(n) CDRs consisting of SEQ ID NOs: 1-6 and 90-95; or
(o) CDRs consisting of SEQ ID NOs: 1-6 and 96-101.

\* \* \* \* \*

SEQUENCE LISTING

```
<160> NUMBER OF SEQ ID NOS: 101

<210> SEQ ID NO 1
<211> LENGTH: 5
<212> TYPE: PRT
<213> ORGANISM: Mus musculus
<220> FEATURE:
<221> NAME/KEY: MISC_FEATURE
<223> OTHER INFORMATION: Anti-IgM Ab (1) heavy chain CDR1

<400> SEQUENCE: 1

Thr Tyr Trp Val Asn
1               5

<210> SEQ ID NO 2
<211> LENGTH: 17
<212> TYPE: PRT
<213> ORGANISM: Mus musculus
<220> FEATURE:
<221> NAME/KEY: MISC_FEATURE
<223> OTHER INFORMATION: Anti-IgM Ab (1) heavy chain CDR2

<400> SEQUENCE: 2

Arg Ile Asp Pro Tyr Asp Ser Glu Thr Leu Tyr Asn Gln Lys Phe Lys
1               5                   10                  15

Asp

<210> SEQ ID NO 3
<211> LENGTH: 9
<212> TYPE: PRT
<213> ORGANISM: Mus musculus
<220> FEATURE:
<221> NAME/KEY: MISC_FEATURE
<223> OTHER INFORMATION: Anti-IgM Ab (1) heavy chain CDR3

<400> SEQUENCE: 3

Glu Thr Tyr Asp Tyr Pro Phe Ala Tyr
1               5

<210> SEQ ID NO 4
<211> LENGTH: 17
<212> TYPE: PRT
<213> ORGANISM: Mus musculus
<220> FEATURE:
<221> NAME/KEY: MISC_FEATURE
<223> OTHER INFORMATION: Anti-IgM Ab (1) light chain CDR1

<400> SEQUENCE: 4

Lys Ser Ser Gln Ser Leu Leu Gln Ser Ser Asn Gln Lys Asn Tyr Leu
1               5                   10                  15

Ala

<210> SEQ ID NO 5
<211> LENGTH: 7
<212> TYPE: PRT
<213> ORGANISM: Mus musculus
```

```
<220> FEATURE:
<221> NAME/KEY: MISC_FEATURE
<223> OTHER INFORMATION: Anti-IgM Ab (1) light chain CDR2

<400> SEQUENCE: 5

Phe Ala Ser Thr Arg Glu Ser
1               5

<210> SEQ ID NO 6
<211> LENGTH: 9
<212> TYPE: PRT
<213> ORGANISM: Mus musculus
<220> FEATURE:
<221> NAME/KEY: MISC_FEATURE
<223> OTHER INFORMATION: Anti-IgM Ab (1) light chain CDR3

<400> SEQUENCE: 6

Gln Gln His Tyr Ser Thr Pro Phe Thr
1               5

<210> SEQ ID NO 7
<211> LENGTH: 7
<212> TYPE: PRT
<213> ORGANISM: Homo sapiens
<220> FEATURE:
<221> NAME/KEY: MISC_FEATURE
<223> OTHER INFORMATION: Anti-HLA-DR Ab (1) heavy chain CDR1

<400> SEQUENCE: 7

Ser Asn Ser Ala Ser Trp Asn
1               5

<210> SEQ ID NO 8
<211> LENGTH: 18
<212> TYPE: PRT
<213> ORGANISM: Homo sapiens
<220> FEATURE:
<221> NAME/KEY: MISC_FEATURE
<223> OTHER INFORMATION: Anti-HLA-DR Ab (1) heavy chain CDR2

<400> SEQUENCE: 8

Arg Thr Tyr Tyr Arg Ser Lys Trp Tyr Asn Asp Tyr Ala Val Ser Val
1               5                   10                  15

Lys Ser

<210> SEQ ID NO 9
<211> LENGTH: 20
<212> TYPE: PRT
<213> ORGANISM: Homo sapiens
<220> FEATURE:
<221> NAME/KEY: MISC_FEATURE
<223> OTHER INFORMATION: Anti-HLA-DR Ab (1) heavy chain CDR3

<400> SEQUENCE: 9

Glu Asn Phe Tyr Gly Ser Glu Thr Cys His Lys Lys Tyr Tyr Cys Tyr
1               5                   10                  15

Gly Met Asp Val
            20

<210> SEQ ID NO 10
<211> LENGTH: 11
<212> TYPE: PRT
<213> ORGANISM: Homo sapiens
<220> FEATURE:
<221> NAME/KEY: MISC_FEATURE
<223> OTHER INFORMATION: Anti-HLA-DR Ab (1) light chain CDR1
```

```
<400> SEQUENCE: 10

Arg Ala Ser Gln Gly Ile Ser Ser Ala Leu Ala
1               5                   10

<210> SEQ ID NO 11
<211> LENGTH: 7
<212> TYPE: PRT
<213> ORGANISM: Homo sapiens
<220> FEATURE:
<221> NAME/KEY: MISC_FEATURE
<223> OTHER INFORMATION: Anti-HLA-DR Ab (1) light chain CDR2

<400> SEQUENCE: 11

Asp Ala Ser Ser Leu Glu Ser
1               5

<210> SEQ ID NO 12
<211> LENGTH: 9
<212> TYPE: PRT
<213> ORGANISM: Homo sapiens
<220> FEATURE:
<221> NAME/KEY: MISC_FEATURE
<223> OTHER INFORMATION: Anti-HLA-DR Ab (1) light chain CDR3

<400> SEQUENCE: 12

Gln Gln Phe Asn Ser Phe Pro Leu Thr
1               5

<210> SEQ ID NO 13
<211> LENGTH: 5
<212> TYPE: PRT
<213> ORGANISM: Mus musculus
<220> FEATURE:
<221> NAME/KEY: MISC_FEATURE
<223> OTHER INFORMATION: Anti-CD20 Ab (1) heavy chain CDR1

<400> SEQUENCE: 13

Ser Tyr Asn Met His
1               5

<210> SEQ ID NO 14
<211> LENGTH: 17
<212> TYPE: PRT
<213> ORGANISM: Mus musculus
<220> FEATURE:
<221> NAME/KEY: MISC_FEATURE
<223> OTHER INFORMATION: Anti-CD20 Ab (1) heavy chain CDR2

<400> SEQUENCE: 14

Ala Ile Tyr Pro Gly Asn Gly Asp Thr Ser Tyr Asn Gln Lys Phe Lys
1               5                   10                  15

Gly

<210> SEQ ID NO 15
<211> LENGTH: 12
<212> TYPE: PRT
<213> ORGANISM: Mus musculus
<220> FEATURE:
<221> NAME/KEY: MISC_FEATURE
<223> OTHER INFORMATION: Anti-CD20 Ab (1) heavy chain CDR3

<400> SEQUENCE: 15

Ser Thr Tyr Tyr Gly Gly Asp Trp Tyr Phe Asn Val
1               5                   10

<210> SEQ ID NO 16
```

```
<211> LENGTH: 10
<212> TYPE: PRT
<213> ORGANISM: Mus musculus
<220> FEATURE:
<221> NAME/KEY: MISC_FEATURE
<223> OTHER INFORMATION: Anti-CD20 Ab (1) light chain CDR1

<400> SEQUENCE: 16

Arg Ala Ser Ser Ser Val Ser Tyr Ile His
1               5                   10

<210> SEQ ID NO 17
<211> LENGTH: 7
<212> TYPE: PRT
<213> ORGANISM: Mus musculus
<220> FEATURE:
<221> NAME/KEY: MISC_FEATURE
<223> OTHER INFORMATION: Anti-CD20 Ab (1) light chain CDR2

<400> SEQUENCE: 17

Ala Thr Ser Asn Leu Ala Ser
1               5

<210> SEQ ID NO 18
<211> LENGTH: 9
<212> TYPE: PRT
<213> ORGANISM: Mus musculus
<220> FEATURE:
<221> NAME/KEY: MISC_FEATURE
<223> OTHER INFORMATION: Anti-CD20 Ab (1) light chain CDR3

<400> SEQUENCE: 18

Gln Gln Trp Thr Ser Asn Pro Pro Thr
1               5

<210> SEQ ID NO 19
<211> LENGTH: 5
<212> TYPE: PRT
<213> ORGANISM: Mus musculus
<220> FEATURE:
<221> NAME/KEY: MISC_FEATURE
<223> OTHER INFORMATION: Anti-CD20 Ab (2) heavy chain CDR1

<400> SEQUENCE: 19

Ser Tyr Asn Met His
1               5

<210> SEQ ID NO 20
<211> LENGTH: 17
<212> TYPE: PRT
<213> ORGANISM: Mus musculus
<220> FEATURE:
<221> NAME/KEY: MISC_FEATURE
<223> OTHER INFORMATION: Anti-CD20 Ab (2) heavy chain CDR2

<400> SEQUENCE: 20

Ala Ile Tyr Pro Gly Asn Gly Asp Thr Ser Tyr Asn Gln Lys Phe Lys
1               5                   10                  15

Gly

<210> SEQ ID NO 21
<211> LENGTH: 13
<212> TYPE: PRT
<213> ORGANISM: Mus musculus
<220> FEATURE:
<221> NAME/KEY: MISC_FEATURE
<223> OTHER INFORMATION: Anti-CD20 Ab (2) heavy chain CDR3
```

```
<400> SEQUENCE: 21

Ala Tyr Tyr Gly Ser Ser Tyr Glu Trp Tyr Phe Asp Val
1               5                   10

<210> SEQ ID NO 22
<211> LENGTH: 10
<212> TYPE: PRT
<213> ORGANISM: Mus musculus
<220> FEATURE:
<221> NAME/KEY: MISC_FEATURE
<223> OTHER INFORMATION: Anti-CD20 Ab (2) light chain CDR1

<400> SEQUENCE: 22

Arg Ala Ser Ser Ser Val Arg Ser Met His
1               5                   10

<210> SEQ ID NO 23
<211> LENGTH: 7
<212> TYPE: PRT
<213> ORGANISM: Mus musculus
<220> FEATURE:
<221> NAME/KEY: MISC_FEATURE
<223> OTHER INFORMATION: Anti-CD20 Ab (2) light chain CDR2

<400> SEQUENCE: 23

Ala Thr Ser Asn Leu Ala Ser
1               5

<210> SEQ ID NO 24
<211> LENGTH: 9
<212> TYPE: PRT
<213> ORGANISM: Mus musculus
<220> FEATURE:
<221> NAME/KEY: MISC_FEATURE
<223> OTHER INFORMATION: Anti-CD20 Ab (2) light chain CDR3

<400> SEQUENCE: 24

Gln Gln Trp Ser Ser Asn Pro Pro Thr
1               5

<210> SEQ ID NO 25
<211> LENGTH: 5
<212> TYPE: PRT
<213> ORGANISM: Mus musculus
<220> FEATURE:
<221> NAME/KEY: MISC_FEATURE
<223> OTHER INFORMATION: Anti-CD32b Ab heavy chain CDR1

<400> SEQUENCE: 25

Asp Ala Trp Met Asp
1               5

<210> SEQ ID NO 26
<211> LENGTH: 19
<212> TYPE: PRT
<213> ORGANISM: Mus musculus
<220> FEATURE:
<221> NAME/KEY: MISC_FEATURE
<223> OTHER INFORMATION: Anti-CD32b Ab heavy chain CDR2

<400> SEQUENCE: 26

Glu Ile Arg Ser Lys Pro Asn Asn His Ala Thr Tyr Tyr Ala Glu Ser
1               5                   10                  15

Val Lys Gly

<210> SEQ ID NO 27
```

-continued

```
<211> LENGTH: 11
<212> TYPE: PRT
<213> ORGANISM: Mus musculus
<220> FEATURE:
<221> NAME/KEY: MISC_FEATURE
<223> OTHER INFORMATION: Anti-CD32b Ab light chain CDR1

<400> SEQUENCE: 27

Arg Ala Ser Gln Glu Ile Ser Gly Tyr Leu Ser
1               5                   10

<210> SEQ ID NO 28
<211> LENGTH: 7
<212> TYPE: PRT
<213> ORGANISM: Mus musculus
<220> FEATURE:
<221> NAME/KEY: MISC_FEATURE
<223> OTHER INFORMATION: Anti-CD32b Ab light chain CDR2

<400> SEQUENCE: 28

Ala Ala Ser Ala Leu Asp Ser
1               5

<210> SEQ ID NO 29
<211> LENGTH: 9
<212> TYPE: PRT
<213> ORGANISM: Mus musculus
<220> FEATURE:
<221> NAME/KEY: MISC_FEATURE
<223> OTHER INFORMATION: Anti-CD32b Ab light chain CDR3

<400> SEQUENCE: 29

Leu Gln Tyr Val Ser Tyr Pro Leu Thr
1               5

<210> SEQ ID NO 30
<211> LENGTH: 5
<212> TYPE: PRT
<213> ORGANISM: Mus musculus
<220> FEATURE:
<221> NAME/KEY: MISC_FEATURE
<223> OTHER INFORMATION: Anti-CD37 Ab heavy chain CDR1

<400> SEQUENCE: 30

Arg Tyr Ser Val His
1               5

<210> SEQ ID NO 31
<211> LENGTH: 16
<212> TYPE: PRT
<213> ORGANISM: Mus musculus
<220> FEATURE:
<221> NAME/KEY: MISC_FEATURE
<223> OTHER INFORMATION: Anti-CD37 Ab heavy chain CDR2

<400> SEQUENCE: 31

Met Ile Trp Gly Gly Gly Ile Thr Asp Tyr Asn Ser Ala Leu Lys Ser
1               5                   10                  15

<210> SEQ ID NO 32
<211> LENGTH: 10
<212> TYPE: PRT
<213> ORGANISM: Mus musculus
<220> FEATURE:
<221> NAME/KEY: MISC_FEATURE
<223> OTHER INFORMATION: Anti-CD37 Ab heavy chain CDR3

<400> SEQUENCE: 32
```

```
Pro Trp Gly Ser Ser Gly Pro Phe Ala Tyr
1               5                   10
```

<210> SEQ ID NO 33
<211> LENGTH: 11
<212> TYPE: PRT
<213> ORGANISM: Mus musculus
<220> FEATURE:
<221> NAME/KEY: MISC_FEATURE
<223> OTHER INFORMATION: Anti-CD37 Ab light chain CDR1

<400> SEQUENCE: 33

```
Arg Ala Ser Gly Asn Ile His Asn Tyr Leu Ala
1               5                   10
```

<210> SEQ ID NO 34
<211> LENGTH: 7
<212> TYPE: PRT
<213> ORGANISM: Mus musculus
<220> FEATURE:
<221> NAME/KEY: MISC_FEATURE
<223> OTHER INFORMATION: Anti-CD37 Ab light chain CDR2

<400> SEQUENCE: 34

```
Asn Ala Lys Thr Leu Ala Asp
1               5
```

<210> SEQ ID NO 35
<211> LENGTH: 9
<212> TYPE: PRT
<213> ORGANISM: Mus musculus
<220> FEATURE:
<221> NAME/KEY: MISC_FEATURE
<223> OTHER INFORMATION: Anti-CD37 Ab light chain CDR3

<400> SEQUENCE: 35

```
Gln His Phe Trp Thr Thr Pro Leu Thr
1               5
```

<210> SEQ ID NO 36
<211> LENGTH: 5
<212> TYPE: PRT
<213> ORGANISM: Rattus norvegicus
<220> FEATURE:
<221> NAME/KEY: MISC_FEATURE
<223> OTHER INFORMATION: Anti-CD52 Ab heavy chain CDR1

<400> SEQUENCE: 36

```
Asp Phe Tyr Met Asn
1               5
```

<210> SEQ ID NO 37
<211> LENGTH: 19
<212> TYPE: PRT
<213> ORGANISM: Rattus norvegicus
<220> FEATURE:
<221> NAME/KEY: MISC_FEATURE
<223> OTHER INFORMATION: Anti-CD52 Ab heavy chain CDR2

<400> SEQUENCE: 37

```
Phe Ile Arg Asp Lys Ala Lys Gly Tyr Thr Thr Glu Tyr Asn Pro Ser
1               5                   10                  15

Val Lys Gly
```

<210> SEQ ID NO 38
<211> LENGTH: 10
<212> TYPE: PRT

<213> ORGANISM: Rattus norvegicus
<220> FEATURE:
<221> NAME/KEY: MISC_FEATURE
<223> OTHER INFORMATION: Anti-CD52 Ab heavy chain CDR3

<400> SEQUENCE: 38

Glu Gly His Thr Ala Ala Pro Phe Asp Tyr
1               5                   10

<210> SEQ ID NO 39
<211> LENGTH: 11
<212> TYPE: PRT
<213> ORGANISM: Rattus norvegicus
<220> FEATURE:
<221> NAME/KEY: MISC_FEATURE
<223> OTHER INFORMATION: Anti-CD52 Ab light chain CDR1

<400> SEQUENCE: 39

Lys Ala Ser Gln Asn Ile Asp Lys Tyr Leu Asn
1               5                   10

<210> SEQ ID NO 40
<211> LENGTH: 7
<212> TYPE: PRT
<213> ORGANISM: Rattus norvegicus
<220> FEATURE:
<221> NAME/KEY: MISC_FEATURE
<223> OTHER INFORMATION: Anti-CD52 Ab light chain CDR2

<400> SEQUENCE: 40

Asn Thr Asn Asn Leu Gln Thr
1               5

<210> SEQ ID NO 41
<211> LENGTH: 9
<212> TYPE: PRT
<213> ORGANISM: Rattus norvegicus
<220> FEATURE:
<221> NAME/KEY: MISC_FEATURE
<223> OTHER INFORMATION: Anti-CD52 Ab light chain CDR3

<400> SEQUENCE: 41

Leu Gln His Ile Ser Arg Pro Arg Thr
1               5

<210> SEQ ID NO 42
<211> LENGTH: 5
<212> TYPE: PRT
<213> ORGANISM: Mus musculus
<220> FEATURE:
<221> NAME/KEY: MISC_FEATURE
<223> OTHER INFORMATION: Anti-BCMA Ab heavy chain CDR1

<400> SEQUENCE: 42

His Tyr Ser Met Asn
1               5

<210> SEQ ID NO 43
<211> LENGTH: 17
<212> TYPE: PRT
<213> ORGANISM: Mus musculus
<220> FEATURE:
<221> NAME/KEY: MISC_FEATURE
<223> OTHER INFORMATION: Anti-BCMA Ab heavy chain CDR2

<400> SEQUENCE: 43

Arg Ile Asn Thr Glu Ser Gly Val Pro Ile Tyr Ala Asp Asp Phe Lys
1               5                   10                  15

Gly

<210> SEQ ID NO 44
<211> LENGTH: 8
<212> TYPE: PRT
<213> ORGANISM: Mus musculus
<220> FEATURE:
<221> NAME/KEY: MISC_FEATURE
<223> OTHER INFORMATION: Anti-BCMA Ab heavy chain CDR3

<400> SEQUENCE: 44

Asp Tyr Leu Tyr Ser Leu Asp Phe
1               5

<210> SEQ ID NO 45
<211> LENGTH: 15
<212> TYPE: PRT
<213> ORGANISM: Mus musculus
<220> FEATURE:
<221> NAME/KEY: MISC_FEATURE
<223> OTHER INFORMATION: Anti-BCMA Ab light chain CDR1

<400> SEQUENCE: 45

Arg Ala Ser Glu Ser Val Thr Ile Leu Gly Ser His Leu Ile Tyr
1               5                   10                  15

<210> SEQ ID NO 46
<211> LENGTH: 7
<212> TYPE: PRT
<213> ORGANISM: Mus musculus
<220> FEATURE:
<221> NAME/KEY: MISC_FEATURE
<223> OTHER INFORMATION: Anti-BCMA Ab light chain CDR2

<400> SEQUENCE: 46

Leu Ala Ser Asn Val Gln Thr
1               5

<210> SEQ ID NO 47
<211> LENGTH: 9
<212> TYPE: PRT
<213> ORGANISM: Mus musculus
<220> FEATURE:
<221> NAME/KEY: MISC_FEATURE
<223> OTHER INFORMATION: Anti-BCMA Ab light chain CDR3

<400> SEQUENCE: 47

Leu Gln Ser Arg Thr Ile Pro Arg Thr
1               5

<210> SEQ ID NO 48
<211> LENGTH: 5
<212> TYPE: PRT
<213> ORGANISM: Mus musculus
<220> FEATURE:
<221> NAME/KEY: MISC_FEATURE
<223> OTHER INFORMATION: Anti-rat IgM Ab heavy chain CDR1

<400> SEQUENCE: 48

Asn Tyr Gly Met Asn
1               5

<210> SEQ ID NO 49
<211> LENGTH: 17
<212> TYPE: PRT
<213> ORGANISM: Mus musculus
<220> FEATURE:

```
<221> NAME/KEY: MISC_FEATURE
<223> OTHER INFORMATION: Anti-rat IgM Ab heavy chain CDR2

<400> SEQUENCE: 49

Trp Ile Asn Thr Tyr Ser Gly Glu Pro Thr Tyr Ala Asp Asp Phe Lys
1               5                   10                  15
Gly

<210> SEQ ID NO 50
<211> LENGTH: 7
<212> TYPE: PRT
<213> ORGANISM: Mus musculus
<220> FEATURE:
<221> NAME/KEY: MISC_FEATURE
<223> OTHER INFORMATION: Anti-rat IgM Ab heavy chain CDR3

<400> SEQUENCE: 50

Glu Thr Thr Ile Phe Asp Tyr
1               5

<210> SEQ ID NO 51
<211> LENGTH: 11
<212> TYPE: PRT
<213> ORGANISM: Mus musculus
<220> FEATURE:
<221> NAME/KEY: MISC_FEATURE
<223> OTHER INFORMATION: Anti-rat IgM Ab light chain CDR1

<400> SEQUENCE: 51

Arg Thr Ser Asp Asn Ile Tyr Ser Tyr Leu Ala
1               5                   10

<210> SEQ ID NO 52
<211> LENGTH: 7
<212> TYPE: PRT
<213> ORGANISM: Mus musculus
<220> FEATURE:
<221> NAME/KEY: MISC_FEATURE
<223> OTHER INFORMATION: Anti-rat IgM Ab light chain CDR2

<400> SEQUENCE: 52

Asn Thr Gln Thr Leu Ala Lys
1               5

<210> SEQ ID NO 53
<211> LENGTH: 9
<212> TYPE: PRT
<213> ORGANISM: Mus musculus
<220> FEATURE:
<221> NAME/KEY: MISC_FEATURE
<223> OTHER INFORMATION: Anti-rat IgM Ab light chain CDR3

<400> SEQUENCE: 53

Gln His His Tyr Asn Thr Pro Tyr Thr
1               5

<210> SEQ ID NO 54
<211> LENGTH: 5
<212> TYPE: PRT
<213> ORGANISM: Mus musculus
<220> FEATURE:
<221> NAME/KEY: MISC_FEATURE
<223> OTHER INFORMATION: Anti-EGFR Ab heavy chain CDR1

<400> SEQUENCE: 54

Ser His Trp Met His
1               5
```

```
<210> SEQ ID NO 55
<211> LENGTH: 17
<212> TYPE: PRT
<213> ORGANISM: Mus musculus
<220> FEATURE:
<221> NAME/KEY: MISC_FEATURE
<223> OTHER INFORMATION: Anti-EGFR Ab heavy chain CDR2

<400> SEQUENCE: 55

Glu Phe Asn Pro Ser Asn Gly Arg Thr Asn Tyr Asn Glu Lys Phe Lys
1               5                   10                  15

Ser

<210> SEQ ID NO 56
<211> LENGTH: 12
<212> TYPE: PRT
<213> ORGANISM: Mus musculus
<220> FEATURE:
<221> NAME/KEY: MISC_FEATURE
<223> OTHER INFORMATION: Anti-EGFR Ab heavy chain CDR3

<400> SEQUENCE: 56

Arg Asp Tyr Asp Tyr Asp Gly Arg Tyr Phe Asp Tyr
1               5                   10

<210> SEQ ID NO 57
<211> LENGTH: 10
<212> TYPE: PRT
<213> ORGANISM: Mus musculus
<220> FEATURE:
<221> NAME/KEY: MISC_FEATURE
<223> OTHER INFORMATION: Anti-EGFR Ab light chain CDR1

<400> SEQUENCE: 57

Ser Ala Ser Ser Ser Val Thr Tyr Met Tyr
1               5                   10

<210> SEQ ID NO 58
<211> LENGTH: 7
<212> TYPE: PRT
<213> ORGANISM: Mus musculus
<220> FEATURE:
<221> NAME/KEY: MISC_FEATURE
<223> OTHER INFORMATION: Anti-EGFR Ab light chain CDR2

<400> SEQUENCE: 58

Asp Thr Ser Asn Leu Ala Ser
1               5

<210> SEQ ID NO 59
<211> LENGTH: 9
<212> TYPE: PRT
<213> ORGANISM: Mus musculus
<220> FEATURE:
<221> NAME/KEY: MISC_FEATURE
<223> OTHER INFORMATION: Anti-EGFR Ab light chain CDR3

<400> SEQUENCE: 59

Gln Gln Trp Ser Ser His Ile Phe Thr
1               5

<210> SEQ ID NO 60
<211> LENGTH: 5
<212> TYPE: PRT
<213> ORGANISM: Mus musculus
<220> FEATURE:
```

```
<221> NAME/KEY: MISC_FEATURE
<223> OTHER INFORMATION: Anti-IgM Ab (2) heavy chain CDR1

<400> SEQUENCE: 60

Ser Phe Gly Met His
1               5

<210> SEQ ID NO 61
<211> LENGTH: 17
<212> TYPE: PRT
<213> ORGANISM: Mus musculus
<220> FEATURE:
<221> NAME/KEY: MISC_FEATURE
<223> OTHER INFORMATION: Anti-IgM Ab (2) heavy chain CDR2

<400> SEQUENCE: 61

Tyr Ile Ser Ser Gly Ser Asn Thr Ile Tyr Tyr Ala Asp Thr Val Lys
1               5                   10                  15

Gly

<210> SEQ ID NO 62
<211> LENGTH: 8
<212> TYPE: PRT
<213> ORGANISM: Mus musculus
<220> FEATURE:
<221> NAME/KEY: MISC_FEATURE
<223> OTHER INFORMATION: Anti-IgM Ab (2) heavy chain CDR3

<400> SEQUENCE: 62

Trp Thr Gly Arg Ala Met Asp Tyr
1               5

<210> SEQ ID NO 63
<211> LENGTH: 11
<212> TYPE: PRT
<213> ORGANISM: Mus musculus
<220> FEATURE:
<221> NAME/KEY: MISC_FEATURE
<223> OTHER INFORMATION: Anti-IgM Ab (2) light chain CDR1

<400> SEQUENCE: 63

Lys Ala Ser Gln Asp Val Gly Thr Ala Val Gly
1               5                   10

<210> SEQ ID NO 64
<211> LENGTH: 7
<212> TYPE: PRT
<213> ORGANISM: Mus musculus
<220> FEATURE:
<221> NAME/KEY: MISC_FEATURE
<223> OTHER INFORMATION: Anti-IgM Ab (2) light chain CDR2

<400> SEQUENCE: 64

Trp Ala Ser Thr Arg His Thr
1               5

<210> SEQ ID NO 65
<211> LENGTH: 9
<212> TYPE: PRT
<213> ORGANISM: Mus musculus
<220> FEATURE:
<221> NAME/KEY: MISC_FEATURE
<223> OTHER INFORMATION: Anti-IgM Ab (2) light chain CDR3

<400> SEQUENCE: 65

Gln Gln Tyr Ser Ser Tyr Leu Tyr Thr
1               5
```

```
<210> SEQ ID NO 66
<211> LENGTH: 5
<212> TYPE: PRT
<213> ORGANISM: Mus musculus
<220> FEATURE:
<221> NAME/KEY: MISC_FEATURE
<223> OTHER INFORMATION: Anti-IgM Ab (3) heavy chain CDR1

<400> SEQUENCE: 66

Ser Tyr Trp Ile Glu
1               5

<210> SEQ ID NO 67
<211> LENGTH: 17
<212> TYPE: PRT
<213> ORGANISM: Mus musculus
<220> FEATURE:
<221> NAME/KEY: MISC_FEATURE
<223> OTHER INFORMATION: Anti-IgM Ab (3) heavy chain CDR2

<400> SEQUENCE: 67

Glu Ile Leu Pro Gly Ser Gly Ser Thr Asn Tyr Asn Glu Lys Phe Lys
1               5                   10                  15

Gly

<210> SEQ ID NO 68
<211> LENGTH: 13
<212> TYPE: PRT
<213> ORGANISM: Mus musculus
<220> FEATURE:
<221> NAME/KEY: MISC_FEATURE
<223> OTHER INFORMATION: Anti-IgM Ab (3) heavy chain CDR3

<400> SEQUENCE: 68

Gln Ile Gly Tyr Tyr Gly Leu Tyr Tyr Gly Met Asp Tyr
1               5                   10

<210> SEQ ID NO 69
<211> LENGTH: 10
<212> TYPE: PRT
<213> ORGANISM: Mus musculus
<220> FEATURE:
<221> NAME/KEY: MISC_FEATURE
<223> OTHER INFORMATION: Anti-IgM Ab (3) light chain CDR1

<400> SEQUENCE: 69

Ser Ala Ser Ser Ser Ile Asn Tyr Met His
1               5                   10

<210> SEQ ID NO 70
<211> LENGTH: 7
<212> TYPE: PRT
<213> ORGANISM: Mus musculus
<220> FEATURE:
<221> NAME/KEY: MISC_FEATURE
<223> OTHER INFORMATION: Anti-IgM Ab (3) light chain CDR2

<400> SEQUENCE: 70

Gly Thr Ser Asn Leu Ala Ser
1               5

<210> SEQ ID NO 71
<211> LENGTH: 9
<212> TYPE: PRT
<213> ORGANISM: Mus musculus
<220> FEATURE:
```

```
<221> NAME/KEY: MISC_FEATURE
<223> OTHER INFORMATION: Anti-IgM Ab (3) light chain CDR3

<400> SEQUENCE: 71

Gln Gln Arg Ser Ser Tyr Pro Leu Thr
1               5

<210> SEQ ID NO 72
<211> LENGTH: 5
<212> TYPE: PRT
<213> ORGANISM: Mus musculus
<220> FEATURE:
<221> NAME/KEY: MISC_FEATURE
<223> OTHER INFORMATION: Anti-IgM Ab (4) heavy chain CDR1

<400> SEQUENCE: 72

Ser Phe Gly Met His
1               5

<210> SEQ ID NO 73
<211> LENGTH: 17
<212> TYPE: PRT
<213> ORGANISM: Mus musculus
<220> FEATURE:
<221> NAME/KEY: MISC_FEATURE
<223> OTHER INFORMATION: Anti-IgM Ab (4) heavy chain CDR2

<400> SEQUENCE: 73

Tyr Ile Ser Ser Gly Ser Asn Thr Ile Tyr Tyr Ala Asp Thr Val Lys
1               5                   10                  15

Gly

<210> SEQ ID NO 74
<211> LENGTH: 8
<212> TYPE: PRT
<213> ORGANISM: Mus musculus
<220> FEATURE:
<221> NAME/KEY: MISC_FEATURE
<223> OTHER INFORMATION: Anti-IgM Ab (4) heavy chain CDR3

<400> SEQUENCE: 74

Trp Thr Gly Arg Ala Met Asp Tyr
1               5

<210> SEQ ID NO 75
<211> LENGTH: 11
<212> TYPE: PRT
<213> ORGANISM: Mus musculus
<220> FEATURE:
<221> NAME/KEY: MISC_FEATURE
<223> OTHER INFORMATION: Anti-IgM Ab (4) light chain CDR1

<400> SEQUENCE: 75

Lys Ala Ser Gln Asp Val Gly Thr Ala Val Ala
1               5                   10

<210> SEQ ID NO 76
<211> LENGTH: 7
<212> TYPE: PRT
<213> ORGANISM: Mus musculus
<220> FEATURE:
<221> NAME/KEY: MISC_FEATURE
<223> OTHER INFORMATION: Anti-IgM Ab (4) light chain CDR2

<400> SEQUENCE: 76

Trp Ala Ser Thr Arg His Ile
1               5
```

```
<210> SEQ ID NO 77
<211> LENGTH: 9
<212> TYPE: PRT
<213> ORGANISM: Mus musculus
<220> FEATURE:
<221> NAME/KEY: MISC_FEATURE
<223> OTHER INFORMATION: Anti-IgM Ab (4) light chain CDR3

<400> SEQUENCE: 77

His Gln Tyr Ser Ser Tyr Leu Tyr Thr
1               5

<210> SEQ ID NO 78
<211> LENGTH: 5
<212> TYPE: PRT
<213> ORGANISM: Mus musculus
<220> FEATURE:
<221> NAME/KEY: MISC_FEATURE
<223> OTHER INFORMATION: Anti-IgM Ab (5) heavy chain CDR1

<400> SEQUENCE: 78

Ser Tyr Val Met His
1               5

<210> SEQ ID NO 79
<211> LENGTH: 17
<212> TYPE: PRT
<213> ORGANISM: Mus musculus
<220> FEATURE:
<221> NAME/KEY: MISC_FEATURE
<223> OTHER INFORMATION: Anti-IgM Ab (5) heavy chain CDR2

<400> SEQUENCE: 79

Tyr Ile Asn Pro Tyr Asn Asp Asp Thr Lys Tyr Asn Glu Asn Phe Lys
1               5                   10                  15

Gly

<210> SEQ ID NO 80
<211> LENGTH: 10
<212> TYPE: PRT
<213> ORGANISM: Mus musculus
<220> FEATURE:
<221> NAME/KEY: MISC_FEATURE
<223> OTHER INFORMATION: Anti-IgM Ab (5) heavy chain CDR3

<400> SEQUENCE: 80

Val Trp Ser Tyr Tyr Ser Ala Met Asp Tyr
1               5                   10

<210> SEQ ID NO 81
<211> LENGTH: 17
<212> TYPE: PRT
<213> ORGANISM: Mus musculus
<220> FEATURE:
<221> NAME/KEY: MISC_FEATURE
<223> OTHER INFORMATION: Anti-IgM Ab (5) light chain CDR1

<400> SEQUENCE: 81

Arg Ser Ser Gln Ser Val Leu Tyr Ser Ser Asn Gln Lys Asn Tyr Leu
1               5                   10                  15

Ala

<210> SEQ ID NO 82
<211> LENGTH: 7
<212> TYPE: PRT
```

<210> SEQ ID NO 82
<211> LENGTH: (not shown)
<212> TYPE: PRT
<213> ORGANISM: Mus musculus
<220> FEATURE:
<221> NAME/KEY: MISC_FEATURE
<223> OTHER INFORMATION: Anti-IgM Ab (5) light chain CDR2

<400> SEQUENCE: 82

Trp Ala Ser Ile Arg Glu Ser
1               5

<210> SEQ ID NO 83
<211> LENGTH: 8
<212> TYPE: PRT
<213> ORGANISM: Mus musculus
<220> FEATURE:
<221> NAME/KEY: MISC_FEATURE
<223> OTHER INFORMATION: Anti-IgM Ab (5) light chain CDR3

<400> SEQUENCE: 83

His Gln Tyr Leu Ser Ser Trp Thr
1               5

<210> SEQ ID NO 84
<211> LENGTH: 5
<212> TYPE: PRT
<213> ORGANISM: Mus musculus
<220> FEATURE:
<221> NAME/KEY: MISC_FEATURE
<223> OTHER INFORMATION: Anti-HLA-DR Ab (2) heavy chain CDR1

<400> SEQUENCE: 84

Asn Tyr Gly Met Asn
1               5

<210> SEQ ID NO 85
<211> LENGTH: 17
<212> TYPE: PRT
<213> ORGANISM: Mus musculus
<220> FEATURE:
<221> NAME/KEY: MISC_FEATURE
<223> OTHER INFORMATION: Anti-HLA-DR Ab (2) heavy chain CDR2

<400> SEQUENCE: 85

Trp Ile Asn Thr Tyr Thr Arg Glu Pro Thr Tyr Ala Asp Asp Phe Lys
1               5                   10                  15
Gly

<210> SEQ ID NO 86
<211> LENGTH: 12
<212> TYPE: PRT
<213> ORGANISM: Mus musculus
<220> FEATURE:
<221> NAME/KEY: MISC_FEATURE
<223> OTHER INFORMATION: Anti-HLA-DR Ab (2) heavy chain CDR3

<400> SEQUENCE: 86

Asp Ile Thr Ala Val Val Pro Thr Gly Phe Asp Tyr
1               5                   10

<210> SEQ ID NO 87
<211> LENGTH: 11
<212> TYPE: PRT
<213> ORGANISM: Mus musculus
<220> FEATURE:
<221> NAME/KEY: MISC_FEATURE
<223> OTHER INFORMATION: Anti-HLA-DR Ab (2) light chain CDR1

<400> SEQUENCE: 87

Arg Ala Ser Glu Asn Ile Tyr Ser Asn Leu Ala
1               5                   10

<210> SEQ ID NO 88
<211> LENGTH: 7
<212> TYPE: PRT
<213> ORGANISM: Mus musculus
<220> FEATURE:
<221> NAME/KEY: MISC_FEATURE
<223> OTHER INFORMATION: Anti-HLA-DR Ab (2) light chain CDR2

<400> SEQUENCE: 88

Ala Ala Ser Asn Leu Ala Asp
1               5

<210> SEQ ID NO 89
<211> LENGTH: 9
<212> TYPE: PRT
<213> ORGANISM: Mus musculus
<220> FEATURE:
<221> NAME/KEY: MISC_FEATURE
<223> OTHER INFORMATION: Anti-HLA-DR Ab (2) light chain CDR3

<400> SEQUENCE: 89

Gln His Phe Trp Thr Thr Pro Trp Ala
1               5

<210> SEQ ID NO 90
<211> LENGTH: 5
<212> TYPE: PRT
<213> ORGANISM: Mus musculus
<220> FEATURE:
<221> NAME/KEY: MISC_FEATURE
<223> OTHER INFORMATION: Anti-CD38 Ab heavy chain CDR1

<400> SEQUENCE: 90

Asp Tyr Gly Met Ser
1               5

<210> SEQ ID NO 91
<211> LENGTH: 17
<212> TYPE: PRT
<213> ORGANISM: Mus musculus
<220> FEATURE:
<221> NAME/KEY: MISC_FEATURE
<223> OTHER INFORMATION: Anti-CD38 Ab heavy chain CDR2

<400> SEQUENCE: 91

Asp Ile Ser Trp Asn Gly Gly Lys Thr His Tyr Val Asp Ser Val Lys
1               5                   10                  15

Gly

<210> SEQ ID NO 92
<211> LENGTH: 14
<212> TYPE: PRT
<213> ORGANISM: Mus musculus
<220> FEATURE:
<221> NAME/KEY: MISC_FEATURE
<223> OTHER INFORMATION: Anti-CD38 Ab heavy chain CDR3

<400> SEQUENCE: 92

Gly Ser Leu Phe His Asp Ser Ser Gly Phe Tyr Phe Gly His
1               5                   10

<210> SEQ ID NO 93
<211> LENGTH: 13
<212> TYPE: PRT

```
<213> ORGANISM: Mus musculus
<220> FEATURE:
<221> NAME/KEY: MISC_FEATURE
<223> OTHER INFORMATION: Anti-CD38 Ab light chain CDR1

<400> SEQUENCE: 93

Ser Gly Ser Ser Ser Asn Ile Gly Asp Asn Tyr Val Ser
1               5                   10

<210> SEQ ID NO 94
<211> LENGTH: 7
<212> TYPE: PRT
<213> ORGANISM: Mus musculus
<220> FEATURE:
<221> NAME/KEY: MISC_FEATURE
<223> OTHER INFORMATION: Anti-CD38 Ab light chain CDR2

<400> SEQUENCE: 94

Arg Asp Ser Gln Arg Pro Ser
1               5

<210> SEQ ID NO 95
<211> LENGTH: 11
<212> TYPE: PRT
<213> ORGANISM: Mus musculus
<220> FEATURE:
<221> NAME/KEY: MISC_FEATURE
<223> OTHER INFORMATION: Anti-CD38 Ab light chain CDR3

<400> SEQUENCE: 95

Gln Ser Tyr Asp Ser Ser Leu Ser Gly Ser Val
1               5                   10

<210> SEQ ID NO 96
<211> LENGTH: 5
<212> TYPE: PRT
<213> ORGANISM: Mus musculus
<220> FEATURE:
<221> NAME/KEY: MISC_FEATURE
<223> OTHER INFORMATION: Anti-CD81 Ab heavy chain CDR1

<400> SEQUENCE: 96

Ser Asn Tyr Met Ser
1               5

<210> SEQ ID NO 97
<211> LENGTH: 19
<212> TYPE: PRT
<213> ORGANISM: Mus musculus
<220> FEATURE:
<221> NAME/KEY: MISC_FEATURE
<223> OTHER INFORMATION: Anti-CD81 Ab heavy chain CDR2

<400> SEQUENCE: 97

Tyr Ile Ser Ser Ser Ser Thr Tyr Thr Asp Tyr Ala Asp Ser Val Lys
1               5                   10                  15

Gly Arg Phe

<210> SEQ ID NO 98
<211> LENGTH: 10
<212> TYPE: PRT
<213> ORGANISM: Mus musculus
<220> FEATURE:
<221> NAME/KEY: MISC_FEATURE
<223> OTHER INFORMATION: Anti-CD81 Ab heavy chain CDR3

<400> SEQUENCE: 98
```

```
Tyr Ser Tyr Gly Arg Asp Asn Phe Asp Tyr
1               5                   10

<210> SEQ ID NO 99
<211> LENGTH: 14
<212> TYPE: PRT
<213> ORGANISM: Mus musculus
<220> FEATURE:
<221> NAME/KEY: MISC_FEATURE
<223> OTHER INFORMATION: Anti-CD81 Ab light chain CDR1

<400> SEQUENCE: 99

Thr Gly Ser Thr Ser Asn Ile Gly Ala Gly Tyr Asp Thr His
1               5                   10

<210> SEQ ID NO 100
<211> LENGTH: 7
<212> TYPE: PRT
<213> ORGANISM: Mus musculus
<220> FEATURE:
<221> NAME/KEY: MISC_FEATURE
<223> OTHER INFORMATION: Anti-CD81 Ab light chain CDR2

<400> SEQUENCE: 100

Gly Asn Ser Asn Arg Pro Ser
1               5

<210> SEQ ID NO 101
<211> LENGTH: 11
<212> TYPE: PRT
<213> ORGANISM: Mus musculus
<220> FEATURE:
<221> NAME/KEY: MISC_FEATURE
<223> OTHER INFORMATION: Anti-CD81 Ab light chain CDR3

<400> SEQUENCE: 101

Gln Ser Tyr Asp Thr Asn Leu Ser Val Trp Val
1               5                   10
```